(12) United States Patent
Coffin

(10) Patent No.: US 10,570,377 B2
(45) Date of Patent: *Feb. 25, 2020

(54) ONCOLYTIC VIRUS STRAIN

(71) Applicant: REPLIMUNE LIMITED, Oxford (GB)

(72) Inventor: Robert Coffin, Oxford (GB)

(73) Assignee: Replimune Limited, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/068,826

(22) PCT Filed: Jan. 9, 2017

(86) PCT No.: PCT/GB2017/050037
§ 371 (c)(1),
(2) Date: Jul. 9, 2018

(87) PCT Pub. No.: WO2017/118865
PCT Pub. Date: Jul. 13, 2017

(65) Prior Publication Data
US 2019/0040366 A1 Feb. 7, 2019

(30) Foreign Application Priority Data

Jan. 8, 2016 (GB) .................................. 1600380.8
Jan. 8, 2016 (GB) .................................. 1600381.6
Jan. 8, 2016 (GB) .................................. 1600382.4

(51) Int. Cl.
| | |
|---|---|
| *C12N 7/00* | (2006.01) |
| *A61P 35/00* | (2006.01) |
| *A61K 35/763* | (2015.01) |
| *A61K 45/06* | (2006.01) |
| *C07K 14/005* | (2006.01) |
| *C07K 14/535* | (2006.01) |
| *A61K 39/395* | (2006.01) |
| *C07K 16/28* | (2006.01) |
| *A61K 35/00* | (2006.01) |
| *A61K 39/00* | (2006.01) |

(52) U.S. Cl.
CPC .............. *C12N 7/00* (2013.01); *A61K 35/763* (2013.01); *A61K 39/3955* (2013.01); *A61K 39/39558* (2013.01); *A61K 45/06* (2013.01); *A61P 35/00* (2018.01); *C07K 14/005* (2013.01); *C07K 14/535* (2013.01); *C07K 16/2818* (2013.01); *A61K 2039/505* (2013.01); *C12N 2710/16621* (2013.01); *C12N 2710/16622* (2013.01); *C12N 2710/16632* (2013.01); *C12N 2710/16633* (2013.01); *C12N 2710/16643* (2013.01); *C12N 2740/13022* (2013.01)

(58) Field of Classification Search
CPC ........ A61K 35/763; A61K 2039/55522; A61K 48/00; A61K 39/39558; C12N 2710/16021; C12N 2710/16643; C12N 2750/14343; C07K 14/535; C07K 2317/21

See application file for complete search history.

(56) References Cited

U.S. PATENT DOCUMENTS

| | | |
|---|---|---|
| 5,122,458 A | 6/1992 | Post et al. |
| 5,168,062 A | 12/1992 | Stinski |
| 5,288,641 A | 2/1994 | Roizman |
| 5,328,688 A | 7/1994 | Roizman |
| 5,385,839 A | 1/1995 | Stinski |
| 5,599,691 A | 2/1997 | Roizman |
| 5,602,007 A | 2/1997 | Dunn et al. |
| 5,698,531 A | 12/1997 | Nabel et al. |
| 5,824,318 A | 10/1998 | Mohr et al. |
| 5,846,707 A | 12/1998 | Roizman |
| 6,040,169 A | 3/2000 | Brown et al. |
| 6,071,692 A | 6/2000 | Roizman |
| 6,120,773 A | 9/2000 | Roizman |
| 6,172,047 B1 | 1/2001 | Roizman et al. |
| 6,297,219 B1 | 10/2001 | Nabel et al. |
| 6,340,673 B1 | 1/2002 | Roizman et al. |
| 6,423,528 B1 | 7/2002 | Brown et al. |
| 6,428,968 B1 | 8/2002 | Molnar-Kimber et al. |
| 6,649,157 B2 | 11/2003 | Coffey et al. |
| 6,770,274 B1 | 8/2004 | Martuza et al. |
| 7,063,835 B2 | 6/2006 | Coffin |

(Continued)

FOREIGN PATENT DOCUMENTS

| | | |
|---|---|---|
| WO | WO 97/12623 | 4/1997 |
| WO | WO01/535505 B2 * | 7/2001 |

(Continued)

OTHER PUBLICATIONS

Loskog, Angelica, "Immunostimulatory Gene Therapy Using Oncolytic Viruses as Vehicles," *Viruses*, 2015, 7:5780-5791.

(Continued)

*Primary Examiner* — Bao Q Li
(74) *Attorney, Agent, or Firm* — Norton Rose Fulbright US LLP

(57) ABSTRACT

The present invention relates to an oncolytic virus which is, or is derived from, a clinical isolate which has been selected by comparing the abilities of a panel of three or more clinical isolates of the same viral species to kill tumor cells of two or more tumor cell lines in vitro and selecting a clinical isolate which is capable of killing cells of two or more tumor cell lines more rapidly and/or at a lower dose in vitro than one or more of the other clinical isolates in the panel.

22 Claims, 33 Drawing Sheets

Specification includes a Sequence Listing.

(56) References Cited

U.S. PATENT DOCUMENTS

| | | | |
|---|---|---|---|
| 7,223,593 | B2 | 5/2007 | Coffin |
| 7,537,924 | B2 | 5/2009 | Coffin |
| 7,749,745 | B2 | 7/2010 | Johnson et al. |
| 7,981,669 | B2 | 7/2011 | Coffin et al. |
| 8,273,568 | B2 | 9/2012 | Martuza et al. |
| 8,277,818 | B2 | 10/2012 | Coffin |
| 8,361,978 | B2 | 1/2013 | Rabkin et al. |
| 8,470,577 | B2 | 6/2013 | Johnson et al. |
| 8,679,830 | B2 | 3/2014 | Coffin et al. |
| 8,680,068 | B2 | 3/2014 | Coffin |
| 8,703,120 | B2 | 4/2014 | Martuza et al. |
| 8,871,193 | B2 | 10/2014 | Johnson et al. |
| 8,986,672 | B2 | 3/2015 | Zhang et al. |
| 9,827,307 | B2 | 11/2017 | Rabkin et al. |
| 9,866,961 | B2 | 1/2018 | Beauchamp |
| 10,039,796 | B2 | 8/2018 | Zhang et al. |
| 10,301,600 | B2 † | 5/2019 | Coffin |
| 2003/0091537 | A1 | 5/2003 | Coffin |
| 2008/0014175 | A1 | 1/2008 | Hallahan et al. |
| 2010/0297072 | A1 | 11/2010 | DePinho |
| 2014/0154216 | A1 | 6/2014 | Coffin |
| 2014/0271677 | A1 | 9/2014 | Palese et al. |
| 2015/0232812 | A1 | 8/2015 | Coffin |

FOREIGN PATENT DOCUMENTS

| | | | |
|---|---|---|---|
| WO | WO01/535506 | A2 * | 7/2001 |
| WO | WO 2006/002394 | | 1/2006 |
| WO | 2007052029 | A1 † | 5/2007 |
| WO | WO 2007/123737 | | 11/2007 |
| WO | WO 2014/022138 | | 2/2014 |
| WO | WO 2014/036412 | | 3/2014 |
| WO | WO 2014/066532 | | 5/2014 |
| WO | WO 2015/077624 | | 5/2015 |
| WO | WO 2016/008976 | | 1/2016 |
| WO | WO 2017/118866 | | 7/2017 |

OTHER PUBLICATIONS

Office Action issued European Patent Application No. 1770385, dated May 21, 2019.

Chou et al., "Mapping of Herpes Simplex Virus-1 Neurovirulence to $\gamma_1 34.5$, a Gene Nonessential for Growth in Culture," *Science*, 1990, 250(4985):1262-1266.

Du et al., "Tumor-specific oncolytic adenoviruses expressing granulocyte macrophage colony-stimulating factor or anti-CTLA4 antibody for the treatment of cancers," *Cancer Gene Therapy*, 2014, 21(8):340-348.

Gangi et al., "The safety of talimogene laherparepvec for the treatment of advanced melanoma," *Expert Opinion on Drug Safety*, 2016, pp. 1-5.

Gibney et al., "Preliminary results from a phase 1/2 study of INCB024360 combined with ipilimumab (ipi) in patients (pts) with melanoma." 2014 ASCO Annual Meeting, No. 3010.

International Search Report and Written Opinion issued in International Patent Application No. PCT/GB2017/050037, dated Apr. 25, 2017.

Liu et al., "ICP34.5 deleted herpes simplex cirus with enhanced oncolytic, immune stimulating, and anti-tumour properties," *Gene Therapy*, 2003, 10(4):292-303.

Maclean et al., "Herpes simplex cirus type 1 deletion variants 1714 and 1716 pinpoint neurovirulence-related sequences in Glasgow strain 17 + between immediate early gene 1 and the 'a' sequence," *Journal of General Virology*, 1991, 72:631-639.

Piasecki et al., "Talilmogene laherparepvec increases the anti-tumor efficacy of the anti-PD-1 immune checkpoint blockade," AACR Annual Meeting Presentation Abstract, Apr. 19, 2015.

Reese, "Abstract IA24: New frontiers in oncolytic virus therapy," *Cancer Immunology Research*, 2016, 4(11):1A24-1A24.

Robinson et al., "Novel Immunocompetent Murine Tumor Model for Evaluation of Conditionally Replication-Competent (Oncolytic) Murine Adenoviral Vectors," *Journal of Virology*, 2009, 83(8):3450-3462.

Senzer et al., "Phase II Clinical Trial of a Granulocyte-Macrophage Colony-Stimulating Factor-Encoding, Second-Generation Oncolytic herpesvirus in Patients with Unresectable Metastatic Melanoma" *Journal of Clinical Oncology*, 2009, 27(34):5763-5771.

Simpson et al., "Combination of a Fusogenic Glycoprotein, Prodrug activation, and Oncolytic Herpes Simplex Virus for Enhanced Local Tumor Control," *Cancer Research*, 2006, 66(9):4835-4842.

Sokolowski et al., "Oncolytic virotherapy using herpes simplex virus: how far have we come?" *Oncolytic Virotherapy*, 2015, 4:207-219.

Yan et al., "Developing Novel Oncolytic Adenoviruses through Bioselection," *Journal of Virology*, 2003, 77(4):2640-2650.

Third Party Submission submitted in Related U.S. Appl. No. 16/068,816, dated Jul. 16, 2019.

Third Party Submission submitted in Related U.S. Appl. No. 16/068,823, dated Jul. 18, 2019.

Third Party Submission submitted in Related U.S. Appl. No. 16/068,830, dated Jul. 30, 2019.

Todo, Tomoki, Armed oncolytic herpes simplex viruses for brain tumor therapy, 208-213, Cell Adhesion * Migration 2:3, Jul./Aug./Sep. 2008.†

\* cited by examiner
† cited by third party

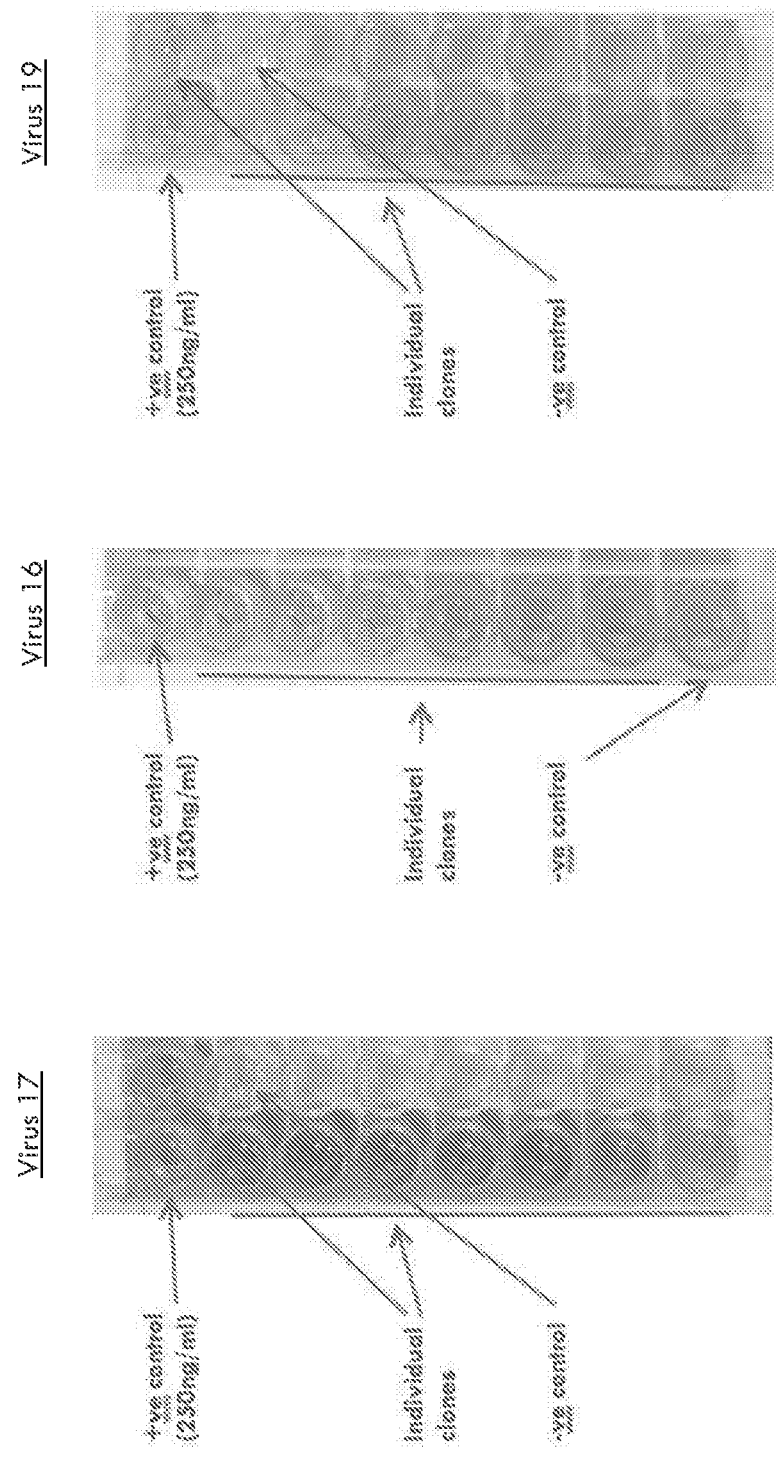

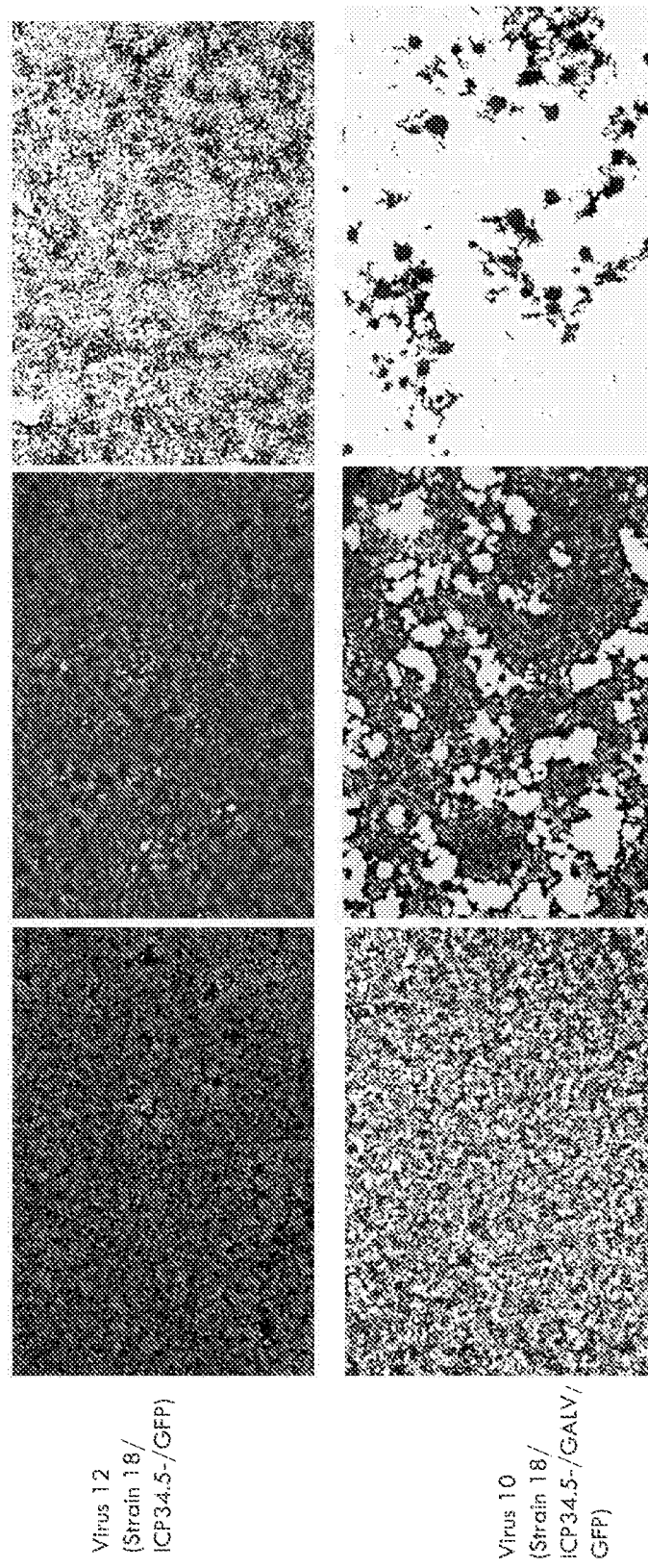

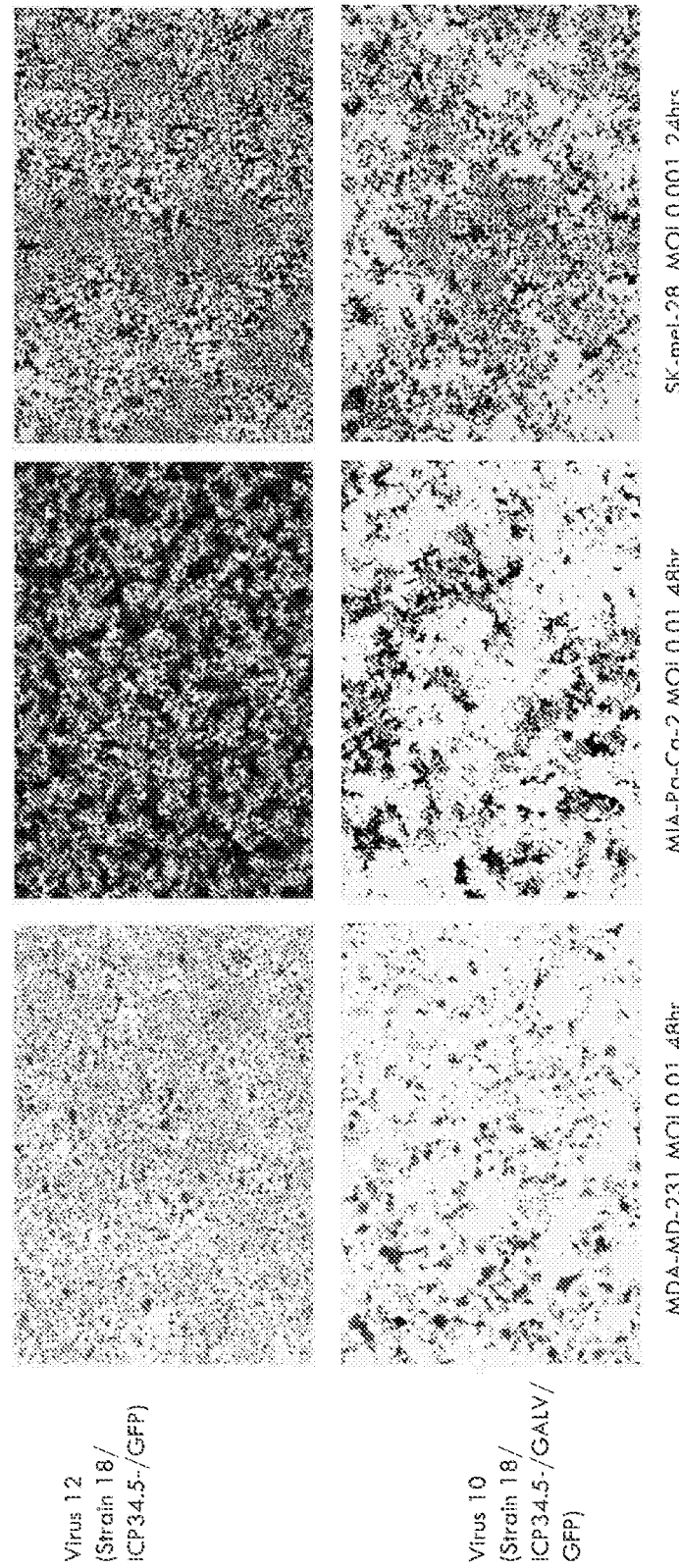

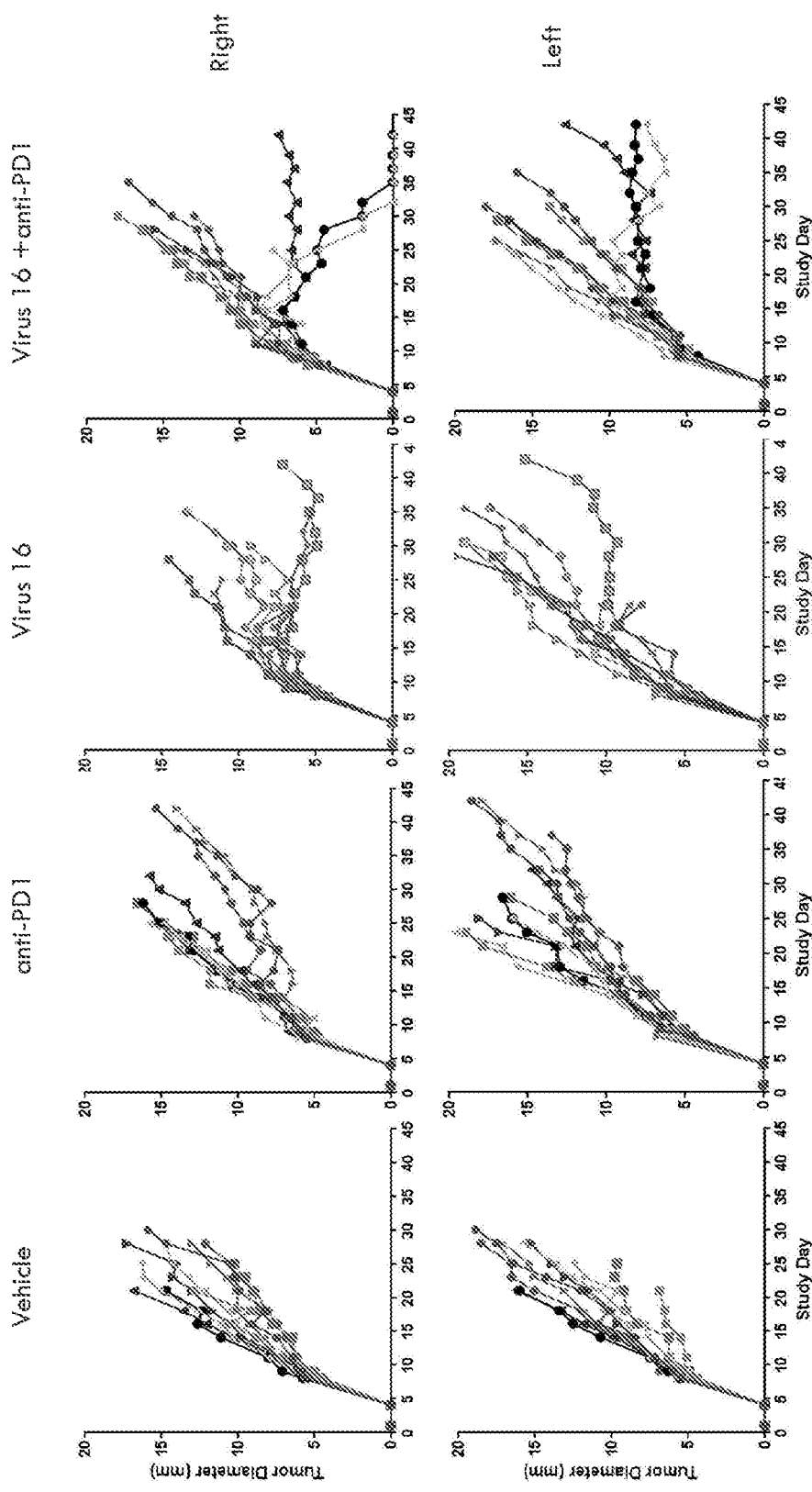

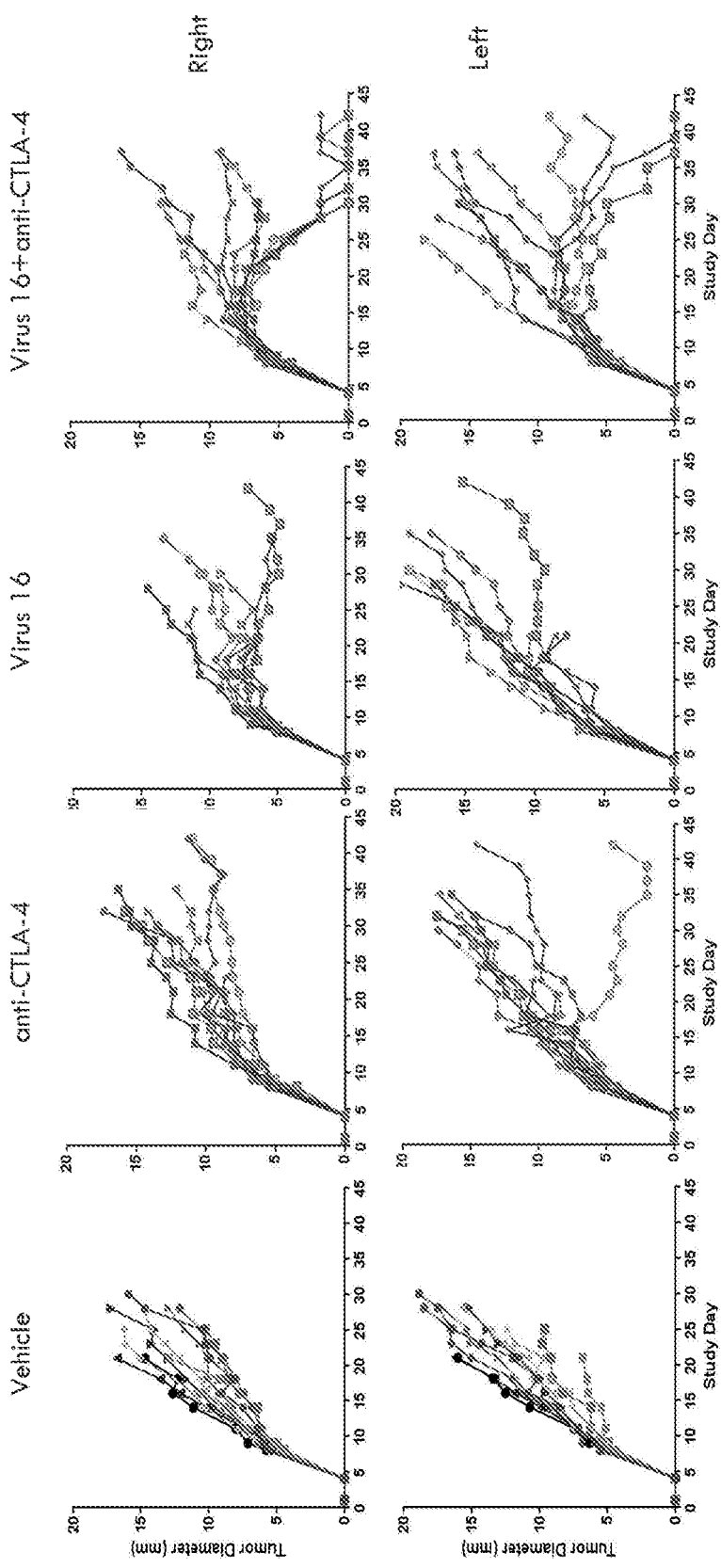

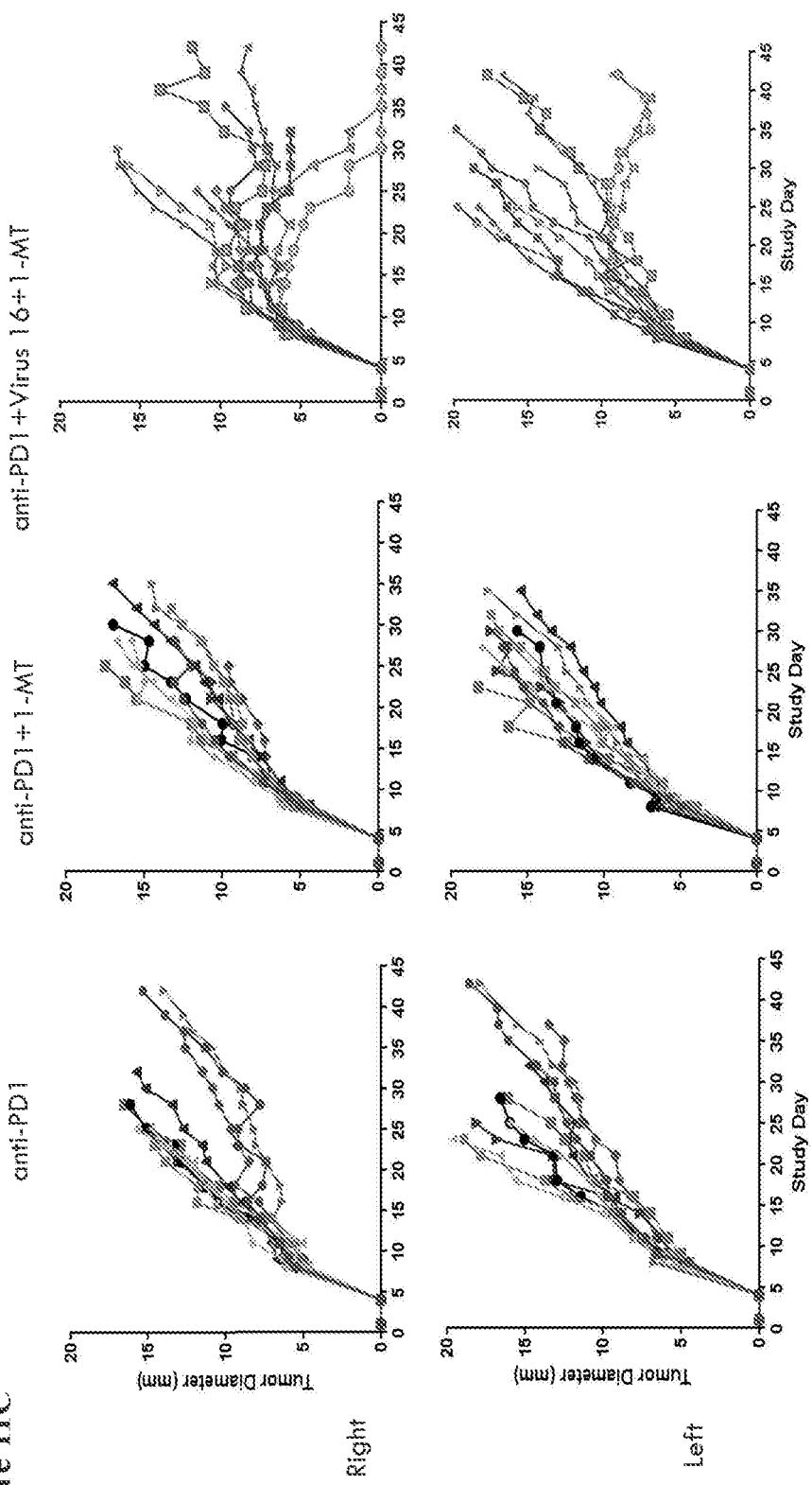

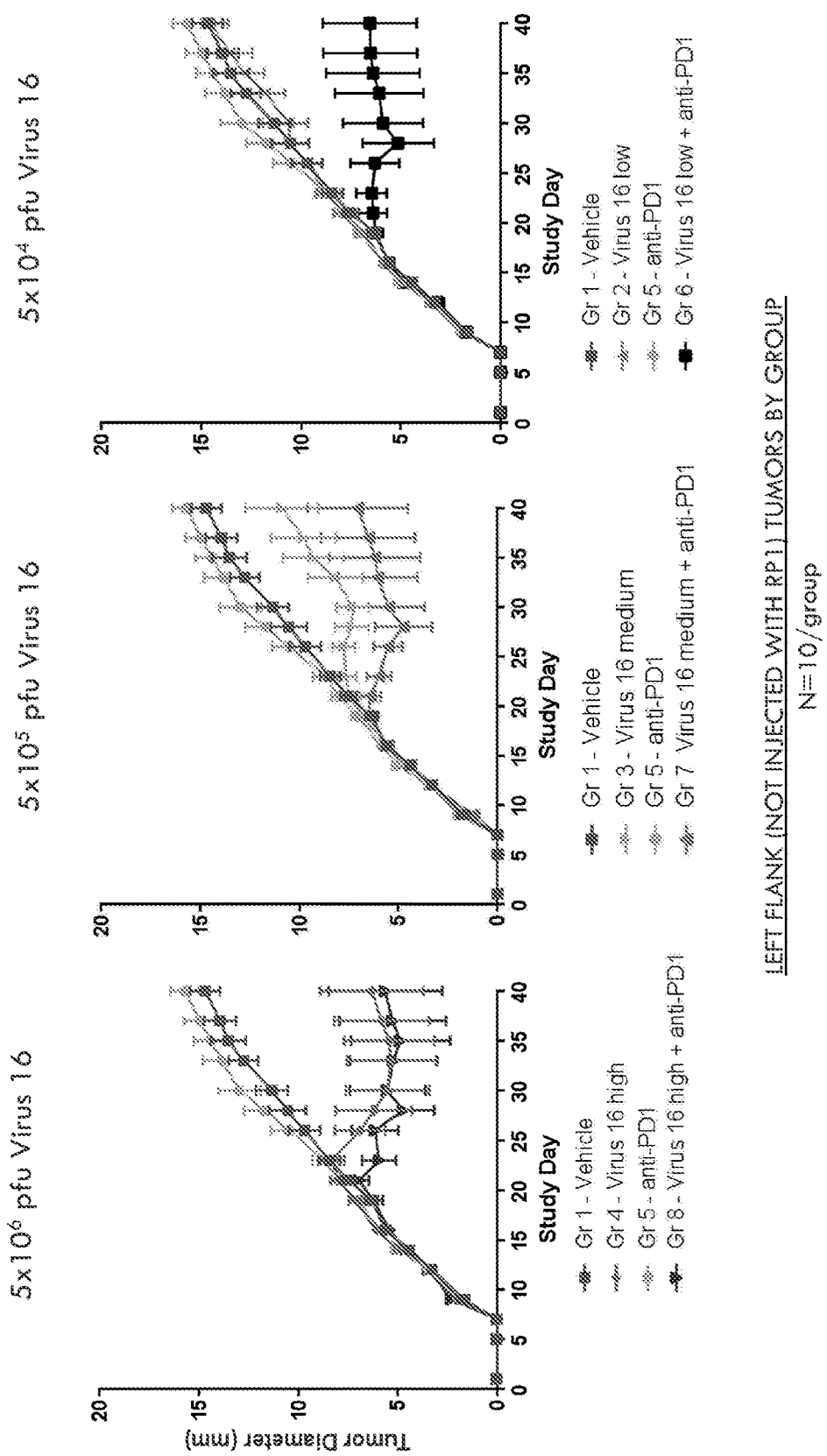

SEQUENCE LISTING

<160> NUMBER OF SEQ ID NOS: 45

<210> SEQ ID NO 1
<211> LENGTH: 426
<212> TYPE: DNA
<213> ORGANISM: Mus musculus

<400> SEQUENCE: 1

| | | | | | |
|---|---|---|---|---|---|
| atgtggctgc | agaatttact | tttcctgggc | attgtggtct | acagcctctc | agcacccacc | 60 |
| cgctcaccca | tcactgtcac | ccggccttgg | aagcatgtag | aggccatcaa | agaagccctg | 120 |
| aacctcctgg | atgacatgcc | tgtcacattg | aatgaagagg | tagaagtcgt | ctctaacgag | 180 |
| ttctccttca | agaagctaac | atgtgtgcag | acccgcctga | agatattcga | gcagggtcta | 240 |
| cggggcaatt | tcaccaaact | caagggcgcc | ttgaacatga | cagccagcta | ctaccagaca | 300 |
| tactgccccc | caactccgga | aacggactgt | gaaacacaag | ttaccaccta | tgcggatttc | 360 |
| atagacagcc | ttaaaacctt | tctgactgat | atcccctttg | aatgcaaaaa | accagtccaa | 420 |
| aaatga | | | | | | 426 |

<210> SEQ ID NO 2
<211> LENGTH: 426
<212> TYPE: DNA
<213> ORGANISM: Mus musculus

<400> SEQUENCE: 2

| | | | | | |
|---|---|---|---|---|---|
| atgtggctcc | agaacctcct | cttcctcggt | atcgtcgtgt | attcactctc | cgcacctact | 60 |
| cgctcaccta | tcactgtcac | cagaccctgg | aagcacgtgg | aggccatcaa | ggaggctctg | 120 |
| aacctgctgg | acgatatgcc | agtgaccctg | aacgaggagg | tggaggtggt | gagcaacgag | 180 |
| ttctccttta | agaagctgac | ctgcgtgcag | acaaggctga | agatcttcga | gcagggcctg | 240 |
| agaggaaact | ttaccaagct | gaagggcgcc | ctgaacatga | ccgcttctta | ctaccagaca | 300 |
| tactgccccc | ctacccccga | gacagactgt | gagacacagg | tgaccacata | cgccgacttc | 360 |
| attgatagcc | tgaaaacatt | cctgaccgac | attccatttg | agtgtaagaa | gcccgtccag | 420 |
| aagtaa | | | | | | 426 |

<210> SEQ ID NO 3
<211> LENGTH: 435
<212> TYPE: DNA
<213> ORGANISM: Homo sapiens

<400> SEQUENCE: 3

| | | | | | |
|---|---|---|---|---|---|
| atgtggctgc | agagcctgct | gctcttgggc | actgtggcct | gcagcatctc | tgcacccgcc | 60 |
| cgctcgccca | gccccagcac | gcagccctgg | gagcatgtga | atgccatcca | ggaggcccgg | 120 |
| cgtctcctga | acctgagtag | agacactgct | gctgagatga | atgaaacagt | agaagtcatc | 180 |
| tcagaaatgt | ttgacctcca | ggagccgacc | tgcctacaga | cccgcctgga | gctgtacaag | 240 |
| cagggcctgc | ggggcagcct | caccaagctc | aagggcccct | tgaccatgat | ggccagccac | 300 |
| tacaagcagc | actgccctcc | aaccccggaa | acttcctgtg | caacccagat | tatcacctttt | 360 |
| gaaagtttca | aagagaacct | gaaggacttt | ctgcttgtca | tcccctttga | ctgctgggag | 420 |
| ccagtccagg | agtga | | | | | 435 |

<210> SEQ ID NO 4
<211> LENGTH: 435
<212> TYPE: DNA
<213> ORGANISM: Homo sapiens

```
<400> SEQUENCE: 4
atgtggctgc agtccctgct gctgctgggc accgtcgcct gttctatttc cgcacccgca      60
aggtcaccaa gtccatctac tcagccttgg gagcacgtga acgcaatcca ggaggcacgg     120
cggctgctga acctgagccg ggacaccgcc gccgagatga cgagacagt ggaagtgatc      180 agcgagatgt tcgatctgca ggagcccacc tgcctgcaga caaggctgga gctgtacaag     240
cagggcctgc gcggctctct gaccaagctg aagggcccac tgacaatgat ggccagccac     300
tataagcagc actgcccccc tacccccgag acaagctgtg ccacccagat catcacattc     360
gagtccttta aggagaacct gaaggatttt ctgctggtca ttccatttga ttgttgggag     420
cccgtccagg agtaa                                                       435

<210> SEQ ID NO 5
<211> LENGTH: 141
<212> TYPE: PRT
<213> ORGANISM: Mus musculus

<400> SEQUENCE: 5

Met Trp Leu Gln Asn Leu Leu Phe Leu Gly Ile Val Val Tyr Ser Leu
1               5                   10                  15

Ser Ala Pro Thr Arg Ser Pro Ile Thr Val Thr Arg Pro Trp Lys His
                20                  25                  30

Val Glu Ala Ile Lys Glu Ala Leu Asn Leu Asp Asp Met Pro Val
            35                  40                  45

Thr Leu Asn Glu Glu Val Glu Val Val Ser Asn Glu Phe Ser Phe Lys
    50                  55                  60

Lys Leu Thr Cys Val Gln Thr Arg Leu Lys Ile Phe Glu Gln Gly Leu
65                  70                  75                  80

Arg Gly Asn Phe Thr Lys Leu Lys Gly Ala Leu Asn Met Thr Ala Ser
                85                  90                  95

Tyr Tyr Gln Thr Tyr Cys Pro Pro Thr Pro Glu Thr Asp Cys Glu Thr
            100                 105                 110

Gln Val Thr Thr Tyr Ala Asp Phe Ile Asp Ser Leu Lys Thr Phe Leu
        115                 120                 125

Thr Asp Ile Pro Phe Glu Cys Lys Lys Pro Val Gln Lys
    130                 135                 140

<210> SEQ ID NO 6
<211> LENGTH: 144
<212> TYPE: PRT
<213> ORGANISM: Homo sapiens

<400> SEQUENCE: 6

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95
```

```
Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 7
<211> LENGTH: 2010
<212> TYPE: DNA
<213> ORGANISM: Gibbon leukemia virus

<400> SEQUENCE: 7
```

| | | | | | |
|---|---|---|---|---|---|
| atggtattgc | tgcctgggtc | catgcttctc | acctcaaacc | tgcaccacct | tcggcaccag | 60 |
| atgagtcctg | ggagctggaa | aagactgatc | atcctcttaa | gctgcgtatt | cggcggcggc | 120 |
| gggacgagtc | tgcaaaataa | gaaccccac | cagcccatga | ccctcacttg | gcaggtactg | 180 |
| tcccaaactg | gagacgttgt | ctgggataca | aaggcagtcc | agcccccttg | gacttggtgg | 240 |
| cccacactta | aacctgatgt | atgtgccttg | gcggctagtc | ttgagtcctg | ggatatcccg | 300 |
| ggaaccgatg | tctcgtcctc | taaacgagtc | agacctccgg | actcagacta | tactgccgct | 360 |
| tataagcaaa | tcacctgggg | agccataggg | tgcagctacc | ctcgggctag | gactagaatg | 420 |
| gcaagctcta | ccttctacgt | atgtcccgg | gatggccgga | ccctttcaga | agctagaagg | 480 |
| tgcgggggc | tagaatccct | atactgtaaa | gaatgggatt | gtgagaccac | ggggaccggt | 540 |
| tattggctat | ctaaatcctc | aaaagacctc | ataactgtaa | aatgggacca | aaatagcgaa | 600 |
| tggactcaaa | aatttcaaca | gtgtcaccag | accggctggt | gtaacccct | taaaatagat | 660 |
| ttcacagaca | aaggaaaatt | atccaaggac | tggataacgg | gaaaaacctg | ggattaaga | 720 |
| ttctatgtgt | ctggacatcc | aggcgtacag | ttcaccattc | gcttaaaaat | caccaacatg | 780 |
| ccagctgtgg | cagtaggtcc | tgacctcgtc | cttgtggaac | aaggacctcc | tagaacgtcc | 840 |
| ctcgctctcc | cacctcctct | tccccaagg | gaagcgccac | cgccatctct | ccccgactct | 900 |
| aactccacag | ccctggcgac | tagtgcacaa | actcccacgg | tgagaaaaac | aattgttacc | 960 |
| ctaaacactc | cgcctcccac | cacaggcgac | agacttttg | atcttgtgca | gggggccttc | 1020 |
| ctaaccttaa | atgctaccaa | cccaggggcc | actgagtctt | gctggctttg | tttggccatg | 1080 |
| ggccccccctt | attatgaagc | aatagcctca | tcaggagagg | tcgcctactc | caccgacctt | 1140 |
| gaccggtgcc | gctggggggac | ccaaggaaag | ctcacccctca | ctgaggtctc | aggacacggg | 1200 |
| ttgtgcatag | gaaaggtgcc | ctttacccat | cagcatctct | gcaatcagac | cctatccatc | 1260 |
| aattcctccg | gagaccatca | gtatctgctc | ccctccaacc | atagctggtg | ggcttgcagc | 1320 |
| actggcctca | ccccttgcct | ctccacctca | gttttaatc | agactagaga | tttctgtatc | 1380 |
| caggtccagc | tgattcctcg | catctattac | tatcctgaag | aagttttgtt | acaggcctat | 1440 |
| gacaattctc | accccaggac | taaaagagag | gctgtctcac | ttaccctagc | tgttttactg | 1500 |
| gggttgggaa | tcacggcggg | aataggtact | ggttcaactg | ccttaattaa | aggacctata | 1560 |
| gacctccagc | aaggcctgac | aagcctccag | atcgccatag | atgctgacct | ccgggccctc | 1620 |
| caagactcag | tcagcaagtt | agaggactca | ctgacttccc | tgtccgaggt | agtgctccaa | 1680 |
| aataggagag | gccttgactt | gctgtttcta | aaagaaggtg | gcctctgtgc | ggccctaaag | 1740 |
| gaagagtgct | gttttacat | agaccactca | ggtgcagtac | gggactccat | gaaaaaactc | 1800 |
| aaagaaaaac | tggataaaag | acagttagag | cgccagaaaa | gccaaaactg | gtatgaagga | 1860 |

| | |
|---|---|
| tggttcaata actccccttg gttcactacc ctgctatcaa ccatcgctgg gcccctatta | 1920 |
| ctcctccttc tgttgctcat cctcgggcca tgcatcatca ataagttagt tcaattcatc | 1980 |
| aatgatagga taagtgcagt taaaatttaa | 2010 |

<210> SEQ ID NO 8
<211> LENGTH: 2013
<212> TYPE: DNA
<213> ORGANISM: Gibbon leukemia virus

<400> SEQUENCE: 8

| | |
|---|---|
| accatggtcc tgctgcctgg gtctatgctg ctgacttcta acctgcacca cctgcgacac | 60 |
| cagatgtctc ccggctcatg gaaacggctg atcatcctgc tgagctgcgt gttcggagga | 120 |
| ggaggcacct ccctgcagaa caagaatcct caccagccaa tgaccctgac atggcaggtg | 180 |
| ctgtcccaga caggcgacgt ggtgtgggat accaaggcag tgcagccacc ttggacatgg | 240 |
| tggcccaccc tgaagcctga cgtgtgcgcc ctggccgcct ccctggagtc ttgggacatc | 300 |
| cccggcacag acgtgagcag cagcaagagg gtgagaccac ccgactctga ttatacagcc | 360 |
| gcctacaagc agatcacctg ggcgccatc ggctgtagct atcctcgggc cgcacaagg | 420 |
| atggccagct ccacctttta cgtgtgccca cgcgacggaa ggaccctgtc tgaggcaagg | 480 |
| agatgtggcg gcctggagag cctgtattgc aaggagtggg attgtgagac acaggcaca | 540 |
| ggctactggc tgtctaagtc tagcaaggac ctgatcaccg tgaagtggga tcagaacagc | 600 |
| gagtggacac agaagttcca gcagtgccac cagaccggct ggtgtaatcc cctgaagatc | 660 |
| gactttacag ataagggcaa gctgtccaag gactggatca ccggcaagac atggggcctg | 720 |
| agattctacg tgtctggcca ccctggcgtg cagtttacaa tccggctgaa gatcaccaac | 780 |
| atgccagcag tggcagtggg accagacctg gtgctggtgg agcagggacc tccacgcacc | 840 |
| tccctggccc tgcccctcc actgccccct agggaggccc caccccctag cctgcccgat | 900 |
| tctaacagca cagccctggc cacctccgcc cagaccccta cagtgcgcaa gaccatcgtg | 960 |
| acactgaata ccccacccc taccacaggc gacaggctgt tcgatctggt gcagggcgcc | 1020 |
| tttctgacac tgaacgccac caatcctggc gcaaccgaga gctgctggct gtgcctggct | 1080 |
| atgggcccac cctactatga ggcaatcgcc tcctctggag aggtggcata ttccacagac | 1140 |
| ctggatagat gcagatgggg caccccaggggc aagctgaccc tgacagaggt gtctggccac | 1200 |
| ggcctgtgca tcggcaaggt gccattcaca caccagcacc tgtgcaacca gaccctgagc | 1260 |
| atcaatagct ccggcgacca ccagtacctg ctgccaagca accactcctg gtgggcatgc | 1320 |
| tccacaggac tgaccccatg tctgagcacc agcgtgttca accagaccag agacttttgt | 1380 |
| atccaggtgc agctgatccc tcggatctac tattacccag aggaggtgct gctgcaggcc | 1440 |
| tatgataatt cccacccaag aacaaagagg gaggccgtgt ctctgaccct ggccgtgctg | 1500 |
| ctgggactgg gaatcacagc aggaatcggc acaggcagca ccgccctgat caagggacca | 1560 |
| atcgacctgc agcagggact gacctccctg cagatcgcca tcgacgccga tctgagagcc | 1620 |
| ctgcaggaca cgtgtccaa gctggaggat tctctgacct ctctgagcga ggtggtgctg | 1680 |
| cagaacagga ggggcctgga cctgctgttc ctgaaggagg aggactgtg cgccgccctg | 1740 |
| aaggaggagt gctgttttta tatcgaccac tctggcgccg tgcgggatag catgaagaag | 1800 |
| ctgaaggaga gctggataaa cgccagctg gagaggcaga gagccagaa ttggtacgag | 1860 |
| ggctggttca caattcccc ctggtttacc acactgctgt ctaccatcgc aggacctctg | 1920 |

```
ttattactgc tgctgctgct gatcctgggc ccatgtatca tcaacaagct ggtgcagttt      1980
atcaacgacc gaatctccgc agtgaaaatc taa                                  2013
```

<210> SEQ ID NO 9
<211> LENGTH: 669
<212> TYPE: PRT
<213> ORGANISM: Gibbon leukemia virus

<400> SEQUENCE: 9

```
Met Val Leu Leu Pro Gly Ser Met Leu Leu Thr Ser Asn Leu His His
 1               5                  10                  15

Leu Arg His Gln Met Ser Pro Gly Ser Trp Lys Arg Leu Ile Ile Leu
            20                  25                  30

Leu Ser Cys Val Phe Gly Gly Gly Thr Ser Leu Gln Asn Lys Asn
        35                  40                  45

Pro His Gln Pro Met Thr Leu Thr Trp Gln Val Leu Ser Gln Thr Gly
    50                  55                  60

Asp Val Val Trp Asp Thr Lys Ala Val Gln Pro Pro Trp Thr Trp Trp
65                  70                  75                  80

Pro Thr Leu Lys Pro Asp Val Cys Ala Leu Ala Ala Ser Leu Glu Ser
                85                  90                  95

Trp Asp Ile Pro Gly Thr Asp Val Ser Ser Lys Arg Val Arg Pro
            100                 105                 110

Pro Asp Ser Asp Tyr Thr Ala Ala Tyr Lys Gln Ile Thr Trp Gly Ala
        115                 120                 125

Ile Gly Cys Ser Tyr Pro Arg Ala Arg Thr Arg Met Ala Ser Ser Thr
    130                 135                 140

Phe Tyr Val Cys Pro Arg Asp Gly Arg Thr Leu Ser Glu Ala Arg Arg
145                 150                 155                 160

Cys Gly Gly Leu Glu Ser Leu Tyr Cys Lys Glu Trp Asp Cys Glu Thr
                165                 170                 175

Thr Gly Thr Gly Tyr Trp Leu Ser Lys Ser Ser Lys Asp Leu Ile Thr
            180                 185                 190

Val Lys Trp Asp Gln Asn Ser Glu Trp Thr Gln Lys Phe Gln Gln Cys
        195                 200                 205

His Gln Thr Gly Trp Cys Asn Pro Leu Lys Ile Asp Phe Thr Asp Lys
    210                 215                 220

Gly Lys Leu Ser Lys Asp Trp Ile Thr Gly Lys Thr Trp Gly Leu Arg
225                 230                 235                 240

Phe Tyr Val Ser Gly His Pro Gly Val Gln Phe Thr Ile Arg Leu Lys
                245                 250                 255

Ile Thr Asn Met Pro Ala Val Ala Val Gly Pro Asp Leu Val Leu Val
            260                 265                 270

Glu Gln Gly Pro Pro Arg Thr Ser Leu Ala Leu Pro Pro Pro Leu Pro
        275                 280                 285

Pro Arg Glu Ala Pro Pro Ser Leu Pro Asp Ser Asn Ser Thr Ala
    290                 295                 300

Leu Ala Thr Ser Ala Gln Thr Pro Thr Val Arg Lys Thr Ile Val Thr
305                 310                 315                 320

Leu Asn Thr Pro Pro Thr Thr Gly Asp Arg Leu Phe Asp Leu Val
                325                 330                 335

Gln Gly Ala Phe Leu Thr Leu Asn Ala Thr Asn Pro Gly Ala Thr Glu
            340                 345                 350

Ser Cys Trp Leu Cys Leu Ala Met Gly Pro Pro Tyr Tyr Glu Ala Ile
```

```
        355                 360                 365
Ala Ser Ser Gly Glu Val Ala Tyr Ser Thr Asp Leu Asp Arg Cys Arg
    370                 375                 380

Trp Gly Thr Gln Gly Lys Leu Thr Leu Thr Glu Val Ser Gly His Gly
385                 390                 395                 400

Leu Cys Ile Gly Lys Val Pro Phe Thr His Gln His Leu Cys Asn Gln
                405                 410                 415

Thr Leu Ser Ile Asn Ser Ser Gly Asp His Gln Tyr Leu Leu Pro Ser
            420                 425                 430

Asn His Ser Trp Trp Ala Cys Ser Thr Gly Leu Thr Pro Cys Leu Ser
        435                 440                 445

Thr Ser Val Phe Asn Gln Thr Arg Asp Phe Cys Ile Gln Val Gln Leu
    450                 455                 460

Ile Pro Arg Ile Tyr Tyr Tyr Pro Glu Glu Val Leu Leu Gln Ala Tyr
465                 470                 475                 480

Asp Asn Ser His Pro Arg Thr Lys Arg Glu Ala Val Ser Leu Thr Leu
                485                 490                 495

Ala Val Leu Leu Gly Leu Gly Ile Thr Ala Gly Ile Gly Thr Gly Ser
            500                 505                 510

Thr Ala Leu Ile Lys Gly Pro Ile Asp Leu Gln Gln Gly Leu Thr Ser
        515                 520                 525

Leu Gln Ile Ala Ile Asp Ala Asp Leu Arg Ala Leu Gln Asp Ser Val
    530                 535                 540

Ser Lys Leu Glu Asp Ser Leu Thr Ser Leu Ser Glu Val Val Leu Gln
545                 550                 555                 560

Asn Arg Arg Gly Leu Asp Leu Leu Phe Leu Lys Glu Gly Gly Leu Cys
                565                 570                 575

Ala Ala Leu Lys Glu Glu Cys Cys Phe Tyr Ile Asp His Ser Gly Ala
            580                 585                 590

Val Arg Asp Ser Met Lys Lys Leu Lys Glu Lys Leu Asp Lys Arg Gln
        595                 600                 605

Leu Glu Arg Gln Lys Ser Gln Asn Trp Tyr Glu Gly Trp Phe Asn Asn
    610                 615                 620

Ser Pro Trp Phe Thr Thr Leu Leu Ser Thr Ile Ala Gly Pro Leu Leu
625                 630                 635                 640

Leu Leu Leu Leu Leu Leu Ile Leu Gly Pro Cys Ile Ile Asn Lys Leu
                645                 650                 655

Val Gln Phe Ile Asn Asp Arg Ile Ser Ala Val Lys Ile
            660                 665

<210> SEQ ID NO 10
<211> LENGTH: 759
<212> TYPE: DNA
<213> ORGANISM: Artificial Sequence
<220> FEATURE:
<223> OTHER INFORMATION: Homo sapiens

<400> SEQUENCE: 10
atgatcgaga cctacaatca gacaagccca cggtccgccg caaccggact gcctatcagc          60
atgaagatct tcatgtacct gctgaccgtg tttctgatca cacagatgat cggctccgcc         120
ctgttcgccg tgtatctgca aggagactg acaagatcg aggatgagcg caatctgcac          180
gaggacttcg tgtttatgaa gaccatccag cggtgcaaca caggcgagag gagcctgtct         240
ctgctgaatt gtgaggagat caagtcccag ttcgagggct tgtgtaagga tatcatgctg         300
```

```
aacaaggagg agacaaagaa ggacgaggat ccacagatcg cagcacacgt ggtgtccgag    360
gcaaactcta atgccgccag cgtgctgcag tgggccaaga agggctacta taccatgaag    420
tctaacctgg tgacactgga gaatggcaag cagctgaccg tgaagaggca gggcctgtac    480
tatatctatg cccaggtgac attctgctct aacagagagg caagctccca ggcacccttc    540
atcgtgggac tgtggctgaa gccctctagc ggcagcgaga ggatcctgct gaaggccgcc    600
aatacccact cctctagcca gctgtgcgag cagcagtcca tccacctggg aggcgtgttc    660
gagctgcagc ctggagccag cgtgttcgtg aacgtgacag acccatctca ggtgagccac    720
ggcaccggct tcacaagctt tggcctgctg aagctgtga                          759
```

```
<210> SEQ ID NO 11
<211> LENGTH: 252
<212> TYPE: PRT
<213> ORGANISM: Artificial Sequence
<220> FEATURE:
<223> OTHER INFORMATION: Homo sapiens

<400> SEQUENCE: 11
```

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Asp Glu Asp Pro Gln
            100                 105                 110

Ile Ala Ala His Val Val Ser Glu Ala Asn Ser Asn Ala Ala Ser Val
        115                 120                 125

Leu Gln Trp Ala Lys Lys Gly Tyr Tyr Thr Met Lys Ser Asn Leu Val
    130                 135                 140

Thr Leu Glu Asn Gly Lys Gln Leu Thr Val Lys Arg Gln Gly Leu Tyr
145                 150                 155                 160

Tyr Ile Tyr Ala Gln Val Thr Phe Cys Ser Asn Arg Glu Ala Ser Ser
                165                 170                 175

Gln Ala Pro Phe Ile Val Gly Leu Trp Leu Lys Pro Ser Ser Gly Ser
            180                 185                 190

Glu Arg Ile Leu Leu Lys Ala Ala Asn Thr His Ser Ser Ser Gln Leu
        195                 200                 205

Cys Glu Gln Gln Ser Ile His Leu Gly Gly Val Phe Glu Leu Gln Pro
    210                 215                 220

Gly Ala Ser Val Phe Val Asn Val Thr Asp Pro Ser Gln Val Ser His
225                 230                 235                 240

Gly Thr Gly Phe Thr Ser Phe Gly Leu Leu Lys Leu
                245                 250

```
<210> SEQ ID NO 12
<211> LENGTH: 1416
<212> TYPE: DNA
<213> ORGANISM: Homo sapiens
```

<400> SEQUENCE: 12

```
atgctgccct ttctgagcat gctggtgctg ctggtgcagc tctgggaaaa cctgggagcc      60
gagatgaaga gcctgtccca gagatctgtg cctaacacct gcacactggt catgtgcagc     120
cccaccgaga atggactgcc tggaagggac ggaagggatg aaggagggg ccctcggggc      180
gagaagggcg acccaggact gcctggacca atgggactga gcggactgca gggaccaaca     240
ggacctgtgg gaccaaaggg agagaacgga tccgccggag agccaggccc taagggcgag     300
aggggcctgt ctggcccccc tggcctgcca ggcatcccag ccccgccgg caaggagggc      360
ccatccggca gcagggcaa tatcggcccc cagggcaagc ctggcccaaa gggcgaggca     420
ggaccaaagg gagaagtggg agcacctggc atgcagggat ccaccggagc aaagggatct     480
acaggaccaa aggcgagcg cggcgcccca ggcgtgcagg gcgcccccgg caatgcagga     540
gcagcaggac cagcaggacc tgcaggccca cagggcgccc ctggctctag ggcccacccc     600
ggcctgaagg gcgacagggg agtgcctggc gataggggca tcaagggaga gagcggactg     660
ccagattccg ccgccctgag gcagcagatg gaggccctga agggcaagct gcagaggctg     720
gaggtggcct ctcccacta ccagaaggcc gccctgtttc agacggcca caggagactg      780
gacaagatcg aggatgagcg caacctgcac gaggatttcg tgtttatgaa gaccatccag     840
agatgcaaca caggcgagcg gtctctgagc ctgctgaatt gtgaggagat caagtctcag     900
ttcgagggct ttgtgaagga catcatgctg aacaaggagg agaccaagaa ggagaatagc     960
ttcgagatgc agaagggcga tcagaatccc cagatcgcag cacacgtgat cagcgaggca    1020
agctccaaga ccacatccgt gctgcagtgg gccgagaagg gctactatac catgtccaac    1080
aatctggtga cactggagaa cggcaagcag ctgaccgtga agagacaggg cctgtactat    1140
atctatgccc aggtgacatt ctgctctaat cgggaggcct ctagccaggc ccctttatc     1200
gcctctctgt gcctgaagag cccaggcaga ttcgagcgga tcctgctgag gccgccaac    1260
acccactcct ctgccaagcc atgcggacag cagagcatcc acctgggagg cgtgttcgag    1320
ctgcagccag gagcctccgt gtttgtgaat gtgacagacc catcccaggt gtctcacgga    1380
accggcttca catcctttgg cctgctgaag ctgtga                               1416
```

<210> SEQ ID NO 13
<211> LENGTH: 471
<212> TYPE: PRT
<213> ORGANISM: Homo sapiens

<400> SEQUENCE: 13

```
Met Leu Pro Phe Leu Ser Met Leu Val Leu Leu Val Gln Pro Leu Gly
 1               5                  10                  15

Asn Leu Gly Ala Glu Met Lys Ser Leu Ser Gln Arg Ser Val Pro Asn
            20                  25                  30

Thr Cys Thr Leu Val Met Cys Ser Pro Thr Glu Asn Gly Leu Pro Gly
        35                  40                  45

Arg Asp Gly Arg Asp Gly Arg Glu Gly Pro Arg Gly Glu Lys Gly Asp
    50                  55                  60

Pro Gly Leu Pro Gly Pro Met Gly Leu Ser Gly Leu Gln Gly Pro Thr
65                  70                  75                  80

Gly Pro Val Gly Pro Lys Gly Glu Asn Gly Ser Ala Gly Glu Pro Gly
                85                  90                  95

Pro Lys Gly Glu Arg Gly Leu Ser Gly Pro Pro Gly Leu Pro Gly Ile
            100                 105                 110
```

```
Pro Gly Pro Ala Gly Lys Glu Gly Pro Ser Lys Gln Gly Asn Ile
        115                 120                 125
Gly Pro Gln Gly Lys Pro Gly Pro Lys Gly Glu Ala Gly Pro Lys Gly
130                 135                 140
Glu Val Gly Ala Pro Gly Met Gln Gly Ser Thr Gly Ala Lys Gly Ser
145                 150                 155                 160
Thr Gly Pro Lys Gly Glu Arg Gly Ala Pro Gly Val Gln Gly Ala Pro
                165                 170                 175
Gly Asn Ala Gly Ala Ala Gly Pro Ala Gly Pro Ala Gly Pro Gln Gly
            180                 185                 190
Ala Pro Gly Ser Arg Gly Pro Pro Gly Leu Lys Gly Asp Arg Gly Val
        195                 200                 205
Pro Gly Asp Arg Gly Ile Lys Gly Glu Ser Gly Leu Pro Asp Ser Ala
210                 215                 220
Ala Leu Arg Gln Gln Met Glu Ala Leu Lys Gly Lys Leu Gln Arg Leu
225                 230                 235                 240
Glu Val Ala Phe Ser His Tyr Gln Lys Ala Ala Leu Phe Pro Asp Gly
                245                 250                 255
His Arg Leu Asp Lys Ile Glu Asp Glu Arg Asn Leu His Glu Asp
            260                 265                 270
Phe Val Phe Met Lys Thr Ile Gln Arg Cys Asn Thr Gly Glu Arg Ser
        275                 280                 285
Leu Ser Leu Leu Asn Cys Glu Glu Ile Lys Ser Gln Phe Glu Gly Phe
290                 295                 300
Val Lys Asp Ile Met Leu Asn Lys Glu Glu Thr Lys Lys Glu Asn Ser
305                 310                 315                 320
Phe Glu Met Gln Lys Gly Asp Gln Asn Pro Gln Ile Ala Ala His Val
                325                 330                 335
Ile Ser Glu Ala Ser Ser Lys Thr Thr Ser Val Leu Gln Trp Ala Glu
            340                 345                 350
Lys Gly Tyr Tyr Thr Met Ser Asn Asn Leu Val Thr Leu Glu Asn Gly
        355                 360                 365
Lys Gln Leu Thr Val Lys Arg Gln Gly Leu Tyr Tyr Ile Tyr Ala Gln
370                 375                 380
Val Thr Phe Cys Ser Asn Arg Glu Ala Ser Ser Gln Ala Pro Phe Ile
385                 390                 395                 400
Ala Ser Leu Cys Leu Lys Ser Pro Gly Arg Phe Glu Arg Ile Leu Leu
                405                 410                 415
Arg Ala Ala Asn Thr His Ser Ser Ala Lys Pro Cys Gly Gln Gln Ser
            420                 425                 430
Ile His Leu Gly Gly Val Phe Glu Leu Gln Pro Gly Ala Ser Val Phe
        435                 440                 445
Val Asn Val Thr Asp Pro Ser Gln Val Ser His Gly Thr Gly Phe Thr
450                 455                 460
Ser Phe Gly Leu Leu Lys Leu
465                 470
```

<210> SEQ ID NO 14
<211> LENGTH: 1412
<212> TYPE: DNA
<213> ORGANISM: Mus musculus

<400> SEQUENCE: 14
atgctgccct tcctgagcat gctggtgctg ctggtgcagc tctgggcaa tctgggcgcc    60

```
gagatgaagt ccctgtctca gaggagcgtg ccaaacacct gcacactggt catgtgctct    120
ccaaccgaga atggactgcc aggaagggac ggaagagatg gaagggaggg accaagggga    180
gagaagggcg accctggact gcctggacca atgggactgt ccggactgca gggaccaaca    240
ggccctgtgg gaccaaaggg agagaatgga agcgccggag agccaggacc taagggagag    300
aggggcctgt ccggccccce tggcctgcct ggcatcccag ccccgccgg caaggagggc    360
ccttctggca agcagggcaa catcggacca cagggcaagc ctggaccaaa gggagaggca    420
ggaccaaagg gagaagtggg agcacccggc atgcagggca gcaccggagc aaaggggatcc    480
accggcccta agggagagag aggagcacct ggagtgcagg gcgccccagg caatgcagga    540
gcagcaggac cagcaggacc tgcaggccca cagggcgccc aggcagccg ggcccaccc    600
ggcctgaagg gcgacagggg agtgccaggc gataggggca tcaagggaga gtccggactg    660
ccagactctg ccgccctgag gcagcagatg gaggccctga agggcaagct gcagaggctg    720
gaggtggcct tctcccacta ccagaaggcc gccctgtttc cagacggaca caggagactg    780
gataaggtgg aggaggaggt gaacctgcac gaggatttcg tgttcatcaa gaagctgaag    840
aggtgcaaca gggcgaggg cagcctgtcc ctgctgaatt gtgaggagat gcggcgccag    900
ttcgaggacc tggtgaagga tatcaccctg aacaaggagg agaagaagga gaattctttt    960
gagatgcaga gggcgacga ggatcctcag atcgcagcac acgtggtgtc cgaggcaaac   1020
tctaatgccg ccagcgtgct gcagtgggcc aagaagggct actataccat gaagtctaac   1080
ctggtcatgc tggagaatgg caagcagctg acagtgaaga gagagggcct gtactacgtg   1140
tacacccagg tgacattctg cagcaacaga gagcccagct cccagcggcc ttttatcgtg   1200
ggcctgtggc tgaagccctc tatcggaagc gagaggatcc tgctgaaggc agccaatacc   1260
cactctagct cccagctgtg cgagcagcag tccgtgcacc tgggaggcgt gttcgagctg   1320
caggcaggag caagcgtgtt cgtgaacgga cagaggccag ccaggtcatc cacagagtgg   1380
gcttctctag ctttggcctg ctgaagctgt ga                                  1412
```

<210> SEQ ID NO 15
<211> LENGTH: 470
<212> TYPE: PRT
<213> ORGANISM: Mus musculus

<400> SEQUENCE: 15

```
Met Leu Pro Phe Leu Ser Met Leu Val Leu Val Gln Pro Leu Gly
1               5                   10                  15

Asn Leu Gly Ala Glu Met Lys Ser Leu Ser Gln Arg Ser Val Pro Asn
                20                  25                  30

Thr Cys Thr Leu Val Met Cys Ser Pro Thr Glu Asn Gly Leu Pro Gly
            35                  40                  45

Arg Asp Gly Arg Asp Gly Arg Glu Gly Pro Arg Gly Glu Lys Gly Asp
        50                  55                  60

Pro Gly Leu Pro Gly Pro Met Gly Leu Ser Gly Leu Gln Gly Pro Thr
65                  70                  75                  80

Gly Pro Val Gly Pro Lys Gly Glu Asn Gly Ser Ala Gly Glu Pro Gly
                85                  90                  95

Pro Lys Gly Glu Arg Gly Leu Ser Gly Pro Pro Gly Leu Pro Gly Ile
            100                 105                 110

Pro Gly Pro Ala Gly Lys Glu Gly Pro Ser Gly Lys Gln Gly Asn Ile
        115                 120                 125
```

Gly Pro Gln Gly Lys Pro Gly Pro Lys Gly Glu Ala Gly Pro Lys Gly
            130                 135                 140

Glu Val Gly Ala Pro Gly Met Gln Gly Ser Thr Gly Ala Lys Gly Ser
145                 150                 155                 160

Thr Gly Pro Lys Gly Glu Arg Gly Ala Pro Gly Val Gln Gly Ala Pro
                165                 170                 175

Gly Asn Ala Gly Ala Ala Gly Pro Ala Gly Pro Ala Gly Pro Gln Gly
            180                 185                 190

Ala Pro Gly Ser Arg Gly Pro Pro Gly Leu Lys Gly Asp Arg Gly Val
        195                 200                 205

Pro Gly Asp Arg Gly Ile Lys Gly Glu Ser Gly Leu Pro Asp Ser Ala
210                 215                 220

Ala Leu Arg Gln Gln Met Glu Ala Leu Lys Gly Lys Leu Gln Arg Leu
225                 230                 235                 240

Glu Val Ala Phe Ser His Tyr Gln Lys Ala Ala Leu Phe Pro Asp Gly
                245                 250                 255

His Arg Arg Leu Asp Lys Val Glu Glu Val Asn Leu His Glu Asp
            260                 265                 270

Phe Val Phe Ile Lys Lys Leu Lys Arg Cys Asn Lys Gly Glu Gly Ser
        275                 280                 285

Leu Ser Leu Leu Asn Cys Glu Glu Met Arg Arg Gln Phe Glu Asp Leu
290                 295                 300

Val Lys Asp Ile Thr Leu Asn Lys Glu Glu Lys Lys Glu Asn Ser Phe
305                 310                 315                 320

Glu Met Gln Arg Gly Asp Glu Asp Pro Gln Ile Ala Ala His Val Val
                325                 330                 335

Ser Glu Ala Asn Ser Asn Ala Ala Ser Val Leu Gln Trp Ala Lys Lys
            340                 345                 350

Gly Tyr Tyr Thr Met Lys Ser Asn Leu Val Met Leu Glu Asn Gly Lys
        355                 360                 365

Gln Leu Thr Val Lys Arg Glu Gly Leu Tyr Tyr Val Tyr Thr Gln Val
370                 375                 380

Thr Phe Cys Ser Asn Arg Glu Pro Ser Ser Gln Arg Pro Phe Ile Val
385                 390                 395                 400

Gly Leu Trp Leu Lys Pro Ser Ile Gly Ser Glu Arg Ile Leu Leu Lys
                405                 410                 415

Ala Ala Asn Thr His Ser Ser Ser Gln Leu Cys Glu Gln Gln Ser Val
            420                 425                 430

His Leu Gly Gly Val Phe Glu Leu Gln Ala Gly Ala Ser Val Phe Val
        435                 440                 445

Asn Val Thr Glu Ala Ser Gln Val Ile His Arg Val Gly Phe Ser Ser
450                 455                 460

Phe Gly Leu Leu Lys Leu
465                 470

<210> SEQ ID NO 16
<211> LENGTH: 786
<212> TYPE: DNA
<213> ORGANISM: Homo sapiens

<400> SEQUENCE: 16
atgatcgaaa catacaacca aacttctccc cgatctgcgg ccactggact gcccatcagc      60
atgaaaattt ttatgtattt acttactgtt tttcttatca cccagatgat tgggtcagca     120 cttttttgctg tgtatcttca tagaaggttg gacaagatag aagatgaaag gaatcttcat     180

```
gaagattttg tattcatgaa aacgatacag agatgcaaca caggagaaag atccttatcc    240
ttactgaact gtgaggagat taaaagccag tttgaaggct ttgtgaagga tataatgtta    300
aacaaagagg agacgaagaa agaaaacagc tttgaaatgc aaaaaggtga tcagaatcct    360
caaattgcgg cacatgtcat aagtgaggcc agcagtaaaa caacatctgt gttacagtgg    420
gctgaaaaag gatactacac catgagcaac aacttggtaa ccctggaaaa tgggaaacag    480
ctgaccgtta aaagacaagg actctattat atctatgccc aagtcacctt ctgttccaat    540
cgggaagctt cgagtcaagc tccatttata gccagcctct gcctaaagtc ccccggtaga    600
ttcgagagaa tcttactcag agctgcaaat acccacagtt ccgccaaacc ttgcgggcaa    660
caatccattc acttgggagg agtatttgaa ttgcaaccag gtgcttcggt gtttgtcaat    720
gtgactgatc caagccaagt gagccatggc actggcttca cgtccttggg cttactcaaa    780
ctctga                                                              786
```

<210> SEQ ID NO 17
<211> LENGTH: 261
<212> TYPE: PRT
<213> ORGANISM: Homo sapiens

<400> SEQUENCE: 17

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255
```

Gly Leu Leu Lys Leu
            260

<210> SEQ ID NO 18
<211> LENGTH: 783
<212> TYPE: DNA
<213> ORGANISM: Mus musculus

<400> SEQUENCE: 18

| | | | | | |
|---|---|---|---|---|---|
| atgatagaaa | catacagcca | accttccccc | agatccgtgg | caactggact | tccagcgagc | 60 |
| atgaagattt | ttatgtattt | acttactgtt | ttccttatca | cccaaatgat | tggatctgtg | 120 |
| cttttgctg | tgtatcttca | tagaagattg | gataaggtcg | aagaggaagt | aaaccttcat | 180 |
| gaagattttg | tattcataaa | aaagctaaag | agatgcaaca | aggagaagg | atctttatcc | 240 |
| ttgctgaact | gtgaggagat | gagaaggcaa | tttgaagacc | ttgtcaagga | tataacgtta | 300 |
| aacaaagaag | agaaaaaaga | aaacagctttt | gaaatgcaaa | gaggtgatga | ggatcctcaa | 360 |
| attgcagcac | acgttgtaag | cgaagccaac | agtaatgcag | catccgttct | acagtgggcc | 420 |
| aagaaaggat | attataccat | gaaaagcaac | ttggtaatgc | ttgaaaatgg | gaaacagctg | 480 |
| acggttaaaa | gagaaggact | ctattatgtc | tacactcaag | tcaccttctg | ctctaatcgg | 540 |
| gagccttcga | gtcaacgccc | attcatcgtc | ggcctctggc | tgaagcccag | cagtggatct | 600 |
| gagagaatct | tactcaaggc | ggcaaatacc | cacagttcct | cccagctttg | cgagcagcag | 660 |
| tctgttcact | tgggcggagt | gtttgaatta | caagctggtg | cttctgtgtt | tgtcaacgtg | 720 |
| actgaagcaa | gccaagtgat | ccacagagtt | ggcttctcat | cttttggctt | actcaaactc | 780 |
| tga | | | | | | 783 |

<210> SEQ ID NO 19
<211> LENGTH: 260
<212> TYPE: PRT
<213> ORGANISM: Mus musculus

<400> SEQUENCE: 19

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Met Leu Glu Asn Gly Lys Gln Leu
145                 150                 155                 160

Thr Val Lys Arg Glu Gly Leu Tyr Tyr Val Tyr Thr Gln Val Thr Phe
                165                 170                 175

```
Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Val His Leu
    210                 215                 220

Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
                245                 250                 255

Leu Leu Lys Leu
        260
```

<210> SEQ ID NO 20
<211> LENGTH: 930
<212> TYPE: DNA
<213> ORGANISM: Mus musculus

<400> SEQUENCE: 20

```
atggatcagc acacactgga cgtggaggat accgctgacg ctaggcaccc agctggcacc      60
tcctgccctt ctgatgccgc tctgctgcgc gacacaggac tgctggccga tgccgctctg     120
ctgtctgaca cagtgcggcc aaccaacgcc gctctgccaa ccgatgctgc ttaccctgct     180
gtgaacgtga gggacagaga ggctgcttgg ccacctgccc tgaacttctg cagccgccac     240
cctaagctgt acggcctggt ggccctggtg ctgctgctgc tgatcgctgc ttgcgtgcca     300
atctttaccc ggacagagcc acgccccgct ctgacaatca ccacatcccc caacctgggc     360
accagggaga caacgccga tcaggtgaca ccagtgtctc acatcggctg ccccaacacc     420
acacagcagg gaagcccagt gttcgccaag ctgctggcta agaaccaggc cagcctgtgc     480
aacaccacac tgaactggca cagccaggac ggagctggaa gctcctacct gtcccagggc     540
ctgagatacg aggaggataa gaaggagctg gtggtggact cccctggact gtactacgtg     600
ttcctggagc tgaagctgtc tccaaccttt acaaacaccg ccacaaggt gcagggatgg     660
gtgtctctgg tgctgcaggc taagccccag gtggacgatt cgataaccct ggccctgacc     720
gtggagctgt ttccttgtag catggagaac aagctggtgg acaggtcttg gagccagctg     780
ctgctgctga aggctggcca caggctgtcc gtgggactga gagcctacct gcacggcgcc     840
aggatgcttt acagagactg ggagctgagc taccctaaca ccacatcctt cggactgttt     900
ctggtgaagc tgacaaccc atgggagtga                                        930
```

<210> SEQ ID NO 21
<211> LENGTH: 765
<212> TYPE: DNA
<213> ORGANISM: Homo sapiens

<400> SEQUENCE: 21

```
atggagtacg cctctgacgc cagcctggat ccagaggccc ttggccacc tgcaccaagg      60
gcccgcgcct ccgcgtgct gccctgggcc ctggtggccg gctgttatt actgctgctg     120
ctggccgccg cctgcgccgt gttcctggca tgtccttggg ccgtgagcgg agccagagcc     180
tccccaggct ctgccgccag ccctcggctg agagagggac cagagctgtc cccagacgat     240
ccagcaggcc tgctggacct gaggcaggga atgtttgccc agctggtggc ccagaacgtg     300
ctgctgatcg acggcccccct gtcctggtac tctgatcctg gcctggccgg cgtgtctctg     360
```

```
accggcggcc tgagctataa ggaggataca aaggagctgg tggtggccaa ggccggcgtg        420
tactacgtgt tcttccagct ggagctgagg agagtggtgg caggagaggg ctctggaagc        480
gtgtccctgg ccctgcacct gcagcccctg cggagcgccg caggagccgc cgccctggcc        540
ctgaccgtgg acctgccacc agccagctcc gaggcaagga attccgcctt cggcttcag         600 ggcagactgc tgcacctgtc tgccggacag aggctgggag tgcacctgca caccgaggcc        660
agggcccgcc acgcatggca gctgacccag ggagcaacag tgctgggcct gttccgcgtg        720
acacctgaga tcccagcagg cctgcctagc ccacggtccg agtga                        765

<210> SEQ ID NO 22
<211> LENGTH: 1389
<212> TYPE: DNA
<213> ORGANISM: Mus musculus

<400> SEQUENCE: 22
atgctgcctt tcctgtccat gctggtgctg ctggtgcagc cactgggcaa cctgggagcc         60
gagatgaagt ctctgagcca gcgcagcgtg cctaacacct gcacactggt catgtgctcc        120
cctacagaga acggcctgcc aggaagggac ggaagagatg aagggaggg accaagggga         180 gagaagggcg accccggact gcctggacca atgggactga gcggcctgca gggaccaacc        240
ggccccgtgg gacctaaggg agagaacgga tccgctggag agccaggacc taagggagag        300
agaggactgt ctggaccacc tggactgcca ggaatcccag accagctgg caaggaggga         360 ccatccggca gcagggaaa catcggacca cagggaaagc ctggaccaaa gggagaggct        420
ggacctaagg gagaagtggg cgccccagga atgcagggct ctacaggagc taagggcagc        480
accggaccaa agggagagag gggagccccc ggagtgcagg gagcccctgg caacgctgga        540
gccgctggcc cagccggacc cgctggccct caggagcccc ccggctctag ggaccaccac        600
ggcctgaagg gagacagagg cgtgcccgga atcggggca tcaagggaga gagcggcctg        660
cctgactccg ccgctctgag acagcagatg gaggctctga agcaagct gcagcggctg        720 gaggtggcct ctctcccacta ccagaaggcc gctctgtttc ctgacggaag acagagccc        780 aggcctgctc tgaccatcac cacatctcca aacctgggca aagagagaa caacgccgat        840 caggtgaccc ccgtgtctca catcggatgc cctaacacca cacagcaggg cagccccgtg        900
tttgccaagc tgctggctaa gaaccaggcc agcctgtgca acaccacact gaactggcac        960
tcccaggatg gcgccggaag ctcctacctg tctcagggcc tgcggtacga ggaggacaag       1020
aaggagctgg tggtggatag cccaggcctg tactacgtgt tcctggagct gaagctgtcc       1080
cccaccttta caaacaccgg acacaaggtg cagggatggg tgagcctggt gctgcaggct       1140
aagccccagg tggacgatt cgacaacctg gccctgaccg tggagctgtt tccttgctct       1200
atggagaaca gctggtgga tagatcctgg agccagctgc tgctgctgaa ggctggacac       1260
cgcctgagcg tgggcctgag ggcttacctg cacggagctc aggacgctta cagggattgg       1320
gagctgtcct accctaacac cacatctttc ggcctgttc tggtgaagcc agacaacccc       1380
tgggagtga                                                              1389

<210> SEQ ID NO 23
<211> LENGTH: 1389
<212> TYPE: DNA
<213> ORGANISM: Homo sapiens

<400> SEQUENCE: 23
atgctgctgt tcctgctgtc cgccctggtg ctgctgaccc agcctctggg ctacctggag         60
```

```
gccgagatga agacctattc tcaccggaca atgccaagcg cctgcacact ggtcatgtgc      120
agcagcgtgg agtctggcct gccaggaagg acggaaggg atggaaggga gggacctaga      180
ggcgagaagg gcgaccctgg cctgccagga gcagcaggac aggcaggaat gcccggccag      240
gccggccccg tgggacctaa gggcgacaac ggaagcgtgg gagagccagg accaaagggc      300
gataccggcc cttccggacc acctggacca ccaggcgtgc ctggcccagc cggcagggag      360
ggccctctgg gcaagcaggg caatatcggc ccacagggca agcccggccc taagggcgag      420
gccggcccca agggcgaagt gggcgcccct ggcatgcagg gaagcgccgg agcccgcggc      480
ctggccggac ctaagggcga gagaggcgtg cctggagaga ggggcgtgcc aggaaacaca      540
ggcgcagcag gatctgccgg agcaatggga ccccagggca gccctggcgc aggggccct       600 ccaggcctga gggcgacaa gggcatccca ggcgataagg gagcaaaggg agagagcggc      660
ctgccagatg tggcctccct cgccagcag gtggaggccc tgcagggcca ggtgcagcac      720
ctgcaggccg ccttctctca gtacaagaag gtggagctgt ttccaaacgg cgcctgcccc      780
tgggccgtga gcggagcccg ggcctcccca ggctctgccg ccagccctag gctgcgcgag      840
ggaccagagc tgagcccaga cgatccagca ggcctgctgg acctgagaca gggaatgttc      900
gcccagctgg tggcccagaa tgtgctgctg atcgacggcc cactgtcctg gtactctgat      960
ccaggcctgg ccggcgtgtc cctgaccggc ggcctgtctt ataaggagga tacaaaggag     1020
ctggtggtgg ccaaggccgg cgtgtactac gtgttcttcc agctggagct gaggagagtg     1080
gtggcaggag agggatccgg atctgtgagc ctggccctgc acctgcagcc cctgcggtcc     1140
gccgcaggag ccgccgccct ggccctgacc gtggacctgc cacctgcctc tagcgaggca     1200
cgcaattccg ccttcggctt tcagggccgg ctgctgcacc tgtctgccgg acagagactg     1260
ggagtgcacc tgcacaccga ggcccgggcc agacacgcct ggcagctgac ccagggagca     1320
acagtgctgg gcctgtttag ggtgacacct gagatcccag ccggcctgcc aagcccccgc     1380
tccgagtga                                                             1389

<210> SEQ ID NO 24
<211> LENGTH: 522
<212> TYPE: DNA
<213> ORGANISM: Mus musculus

<400> SEQUENCE: 24
atggaggaga tgcctctgag ggagagctcc ccacagaggg ccgagagatg caagaagagc       60
tggctgctgt gcatcgtggc tctgctgctg atgctgctgt gctctctggg caccctgatc      120
tacacaagcc tgaagccaac cgccatcgag tcctgtatgg tgaagttcga gctgtctagc      180
tccaagtggc acatgacatc ccccaagcct cactgcgtga acaccacatc tgacggaaag      240
ctgaagatcc tgcagagcgg cacctacctg atctacggac aggtcatccc cgtggacaag      300
aagtacatca aggataacgc cccttttcgtg gtgcagatct acaagaagaa cgacgtgctg      360
cagacactga tgaacgattt tcagatcctg cccatcggcg gagtgtacga gctgcacgct      420
ggcgacaaca tctacctgaa gttcaactcc aaggatcaca tccagaagac caacacatac      480 tgggaatca tcctgatgcc agatctgccc tttatctctt ga                          522

<210> SEQ ID NO 25
<211> LENGTH: 600
<212> TYPE: DNA
<213> ORGANISM: Homo sapiens
```

<400> SEQUENCE: 25

```
atgaccctgc acccaagccc catcacatgc gagttcctgt tttctaccgc cctgatcagc    60
ccaaagatgt gcctgagcca cctggagaat atgccctgt cccactctcg acacaggga    120
gcccagagaa gctcctggaa gctgtggctg ttctgctcta tcgtgatgct gctgttcctg   180
tgcagctttt cctggctgat cttcatcttt ctgcagctgg agacagccaa ggagccttgc   240
atggccaagt ttggccctct gccatccaag tggcagatgg cctctagcga gccccttgc    300
gtgaacaagg tgagcgactg gaagctggag atcctgcaga acggcctgta cctgatctat   360
ggccaggtgg cccccaacgc caattacaac gacgtggccc ctttcgaggt gcggctgtat   420
aagaacaagg atatgatcca gaccctgaca aataagtcta agatccagaa cgtgggcggc   480
acatacgagc tgcacgtggg cgacaccatc gacctgatct tcaacagcga gcaccaggtg   540
ctgaagaaca atacatattg gggcatcatc ctgctggcca ccccagtt tatctcctga    600
```

<210> SEQ ID NO 26
<211> LENGTH: 1164
<212> TYPE: DNA
<213> ORGANISM: Mus musculus

<400> SEQUENCE: 26

```
atgctgcctt tcctgtctat gctggtgctg ctggtgcagc cactgggcaa cctgggagcc    60
gagatgaaga gcctgtccca gagatccgtg cccaacacct gcacactggt catgtgctct   120
cctaccgaga acggcctgcc aggaagggac ggaagagatg aagggagggg acctcgggga   180
gagaagggcg acccaggact gcctggacca atgggactga gcggcctgca gggaccaaca   240
ggccccgtgg gacctaaggg agagaacgga agcgccggag agccaggacc taagggagag   300
aggggactgt ccgaccacc tggactgcct ggaatcccag accagctgg caaggaggga   360
ccatccggca agcagggaaa catcggacca cagggaaagc ctggaccaaa gggagaggct   420
ggaccaaagg gagaagtggg cgctcctgga atgcagggct ccaccggagc caagggctct   480
acaggaccaa aggagagag gggagctccc ggagtgcagg gagcccctgg caacgctgga   540
gccgctggcc cagccggacc cgctggccct caggagcccc aggcagcag gggaccaccc   600
ggcctgaagg gcgacagggg cgtgccagga gataggggca tcaagggaga gtctggcctg   660
ccagacagcg ccgctctgag acagcagatg gaggccctga agggcaagct gcagcggctg   720
gaggtggctt ctctcccacta ccagaaggcc gctctgtttc cagatggcag cctgaagccc   780
accgccatcg agtcctgcat ggtgaagttt gagctgagct cctctaagtg gcacatgaca   840
tctcccaagc ctcactgcgt gaacaccaca tctgacggca agctgaagat cctgcagagc   900
ggcacctacc tgatctacgg ccaggtcatc cccgtggaca agaagtacat caaggataac   960
gcccctttcg tggtgcagat ctacaagaag aacgacgtgc tgcagacact gatgaacgat  1020
tttcagatcc tgccaatcgg cggagtgtac gagctgcacg ctggcgacaa catctacctg  1080
aagttcaact ctaaggatca catccagaag accaacacat actggggcat catcctgatg  1140
ccagatctgc cctttatcag ctga                                          1164
```

<210> SEQ ID NO 27
<211> LENGTH: 1152
<212> TYPE: DNA
<213> ORGANISM: Homo sapiens

<400> SEQUENCE: 27

```
atgctgctgt tcctgctgtc tgccctggtg ctgctgaccc agccactggg ctacctggag    60
```

```
gccgagatga agacctattc ccaccgcaca atgccttctg cctgcacact ggtcatgtgc      120
agcagcgtgg agagcggcct gccaggaagg gacggaagga atggaaggga gggacccaga      180
ggcgagaagg gcgaccctgg cctgccagga gcagcaggac aggcaggaat gccaggccag      240
gccggccccg tgggccctaa gggcgacaat ggatccgtgg gagagccagg accaaagggc      300
gataccggcc cttctggacc acctggacca ccaggcgtgc ctggaccagc aggaagagag      360
ggacctctgg gcaagcaggg aaacatcgga ccacagggca agccaggccc taagggcgag      420
gccggcccca agggcgaagt gggcgcccct ggcatgcagg gatccgccgg agccaggggc      480
ctggccggac ctaagggcga gcgcggcgtg cctggagaga gggcgtgcc aggaaataca      540 ggcgcagcag gatctgccgg agcaatggga ccacagggca gccccggcgc cagaggccct      600
ccaggcctga gggcgacaa gggaatccct ggcgataagg gagcaaaggg agagagcggc      660
ctgccagacg tggcctccct gaggcagcag gtggaggccc tgcagggaca ggtgcagcac      720
ctgcaggccg ccttcagcca gtacaagaag gtggagctgt ttccaaatgg cgagacagcc      780
aaggagccct gcatggccaa gttcggccca ctgcccagca gtggcagat ggcctctagc      840 gaccccctt gcgtgaacaa ggtgagcgat tggaagctgg agatcctgca gaacggcctg      900
tacctgatct atggccaggt ggcccccaac gccaattaca cgacgtggc ccctttttgag      960 gtgcggctgt ataagaacaa ggatatgatc cagaccctga caaataagtc taagatccag     1020
aacgtgggag gcacctacga gctgcacgtg ggcgacacaa tcgacctgat cttcaacagc     1080
gagcaccagg tgctgaagaa caatacatat tggggcatca tcctgctggc caaccccag      1140 tttatctcct ga                                                         1152

<210> SEQ ID NO 28
<211> LENGTH: 597
<212> TYPE: DNA
<213> ORGANISM: Mus musculus

<400> SEQUENCE: 28
atggagggcg agggagtgca gcccctggat gagaacctgg agaacggctc ccggcctcgc       60
ttcaagtgga agaagaccct gcggctggtg gtgtctggaa tcaagggcgc cggaatgctg      120
ctgtgcttta tctacgtgtg cctgcagctg agctcctctc ccgccaagga tccccctatc      180
cagaggctga gaggagctgt gaccaggtgc gaggacggca gctgttcat cagctcctac      240 aagaacgagt accagacaat ggaggtgcag aacaacagcg tggtcatcaa gtgtgatggc      300
ctgtacatca tctacctgaa gggatccttc tttcaggagg tgaagatcga cctgcacttt      360
cgggaggatc acaacccaat ctctatcccc atgctgaacg acggcaggag aatcgtgttc      420
acagtggtgg ccagcctggc ttttaaggac aaggtgtacc tgaccgtgaa cgccccagat      480
acactgtgcg agcacctgca gatcaacgac ggagagctga tcgtggtgca gctgacccct      540
ggctactgtg ctccagaggg atcttaccac agcacagtga accaggtgcc cctgtga         597

<210> SEQ ID NO 29
<211> LENGTH: 552
<212> TYPE: DNA
<213> ORGANISM: Homo sapiens

<400> SEQUENCE: 29
atggagaggg tgcagcccct ggaggagaac gtgggaaatg ccgcccggcc tagattcgag       60
aggaacaagc tgctgctggt ggcctctgtg atccaggggc tgggcctgct gctgtgcttc      120
```

```
acctacatct gtctgcactt ttctgccctg caggtgagcc acagataccc ccgcatccag    180
agcatcaagg tgcagttcac cgagtataag aaggagaagg gctttatcct gacatcccag    240
aaggaggacg agatcatgaa ggtgcagaac aattctgtga tcatcaactg cgatggcttc    300
tacctgatct ccctgaaggg ctattttttct caggaagtga atatcagcct gcactatcag    360
aaggacgagg agccactgtt tcagctgaag aaggtgcgga gcgtgaattc cctgatggtg    420
gccagcctga cctacaagga caaggtgtat ctgaacgtga ccacagataa tacatccctg    480
gacgatttcc acgtgaacgg cggcgagctg atcctgatcc accagaatcc cggcgagttt    540
tgcgtgctgt ga                                                        552
```

```
<210> SEQ ID NO 30
<211> LENGTH: 1215
<212> TYPE: DNA
<213> ORGANISM: Mus musculus

<400> SEQUENCE: 30
```

```
atgctgccct tcctgtccat gctggtgctg ctggtgcagc tctgggcaa cctgggagcc     60 gagatgaagt ctctgagcca gagatccgtg ccaaacacct gcacactggt catgtgctct   120
cccaccgaga acggctgcc tggaagggac ggaagagatg aagggaggg accccgggga   180 gagaagggcg atcctggact gccaggacct atgggactga gcggcctgca gggaccaaca   240
ggccccgtgg gacctaaggg agagaacgga agcgccggag agccaggacc aaagggagag   300
aggggactgt ccggcccacc tggactgcct ggaatccctg gaccagctgg caaggaggga   360
ccttccggca gcagggaaa catcggacca cagggaaagc caggacctaa gggagaggct   420
ggaccaaagg gagaagtggg cgctcccgga atgcagggct ctaccggagc caagggcagc   480
acaggaccta agggagagag ggagctcca ggagtgcagg gagcccccgg caacgctgga   540
gctgctggac cagctggacc agctggccct cagggagccc caggctctag ggaccacca   600 ggcctgaagg gcgacagggg cgtgccagga gataggggca tcaagggaga gagcggcctg   660
ccagattccg ccgctctgag acagcagatg gaggccctga agggcaagct gcagcggctg   720
gaggtggctt tcagccacta ccagaaggcc gctctgtttc ctgacggcag ctcctctcca   780
gccaaggatc ctccaatcca gcggctgcgc ggagctgtga ccaggtgcga ggatggccag   840
ctgttcatca gctcctacaa gaacgagtac cagacaatgg aggtgcagaa caactctgtg   900
gtcatcaagt gtgacggcct gtacatcatc tacctgaagg gcagcttctt tcaggaggtg   960
aagatcgacc tgcactttag agaggatcac aacccaatct ccatcccat gctgaacgac  1020 ggcaggagaa tcgtgttcac cgtggtggcc tctctggctt ttaaggacaa ggtgtacctg  1080
accgtgaacg cccccgatac actgtgcgag cacctgcaga tcaacgacgg cgagctgatc  1140
gtggtgcagc tgaccctgg atactgtgct ccagagggct cctaccactc tacagtgaac  1200
caggtgcctc tgtga                                                   1215
```

```
<210> SEQ ID NO 31
<211> LENGTH: 1170
<212> TYPE: DNA
<213> ORGANISM: Homo sapiens

<400> SEQUENCE: 31
```

```
atgctgctgt tcctgctgag cgccctggtg ctgctgaccc agccactggg ctacctggag     60
gccgagatga agacctattc ccacagaaca atgcctctg cctgcacact ggtcatgtgc    120
agcagcgtgg agtccggcct gccaggaagg gacggcagag atggcaggga gggccccagg    180
```

```
ggcgagaagg gcgaccccgg cctgcctgga gcagcaggcc aggccggcat gccaggccag      240
gccggcccag tgggcCccaa gggcgacaac ggcagcgtgg gcgagcccgg ccctaagggc      300
gataccggcc cctccggccc ccctggccca cccggcgtgc caggaccagc aggaagggag      360
ggaccactgg gcaagcaggg caatatcgga cctcagggca agcctggacc aaagggagag      420
gcaggaccaa agggagaagt gggcgcccct ggcatgcagg gatctgccgg agcccggggc      480
ctggccggcc ccaagggcga gagggcgtg cccggcgaga ggggcgtgcc tggcaacaca       540
ggcgccgccg gctccgccgg cgccatggga cctcagggct ctccaggagc cagaggccct      600
ccaggcctga gggcgacaa gggaatccct ggcgataagg gagcaaaggg agagagcggc       660
ctgccagacg tggcctccct gcggcagcag gtggaggccc tgcagggcca ggtgcagcac      720
ctgcaggccg ccttcagcca gtacaagaag gtggagctgt ttcctaatgg cgtgtctcac      780
cgctacccac ggatccagag catcaaggtg cagttcaccg agtataagaa ggagaagggc      840
tttatcctga catctcagaa ggaggacgag atcatgaagg tgcagaacaa tagcgtgatc      900
atcaactgcg atggcttcta cctgatcagc ctgaagggct atttttccca ggaagtgaat      960
atctctctgc actatcagaa ggatgaggag cctctgtttc agctgaagaa ggtgagatct     1020
gtgaacagcc tgatggtggc ctccctgacc tacaaggaca aggtgtatct gaacgtgacc     1080
acagataata catctctgga cgatttccac gtgaacggcg cgagctgat cctgatccac      1140 cagaatcccg cgagttttg cgtgctgtga                                        1170

<210> SEQ ID NO 32
<211> LENGTH: 969
<212> TYPE: DNA
<213> ORGANISM: Mus musculus

<400> SEQUENCE: 32
atgcagctga agtgtccatg cttcgtgtcc ctgggaacaa gacagcccgt ctggaagaaa       60
ctgcacgtga gctccggctt cttagcggc ctggggctgt ttctgctgct gctgtctagt      120
ctgtgcgccg cttccgcaga gactgaagtc ggagccatgg tgggcagtaa cgtggtcctg     180
tcatgcatcg acccacaccg acggcatttc aacctgtctg gcctgtacgt gtattggcag     240
attgagaatc ccgaagtgtc agtcacctac tatctgcctt acaagagccc agggatcaac     300
gtggactcaa gctataaaaa tagggggcac ctgtccctgg attctatgaa gcagggaaac     360
ttcagcctgt acctgaaaaa tgtgaccccc caggacacac aggagttcac ttgtcgcgtc     420
tttatgaaca ctgcaaccga actggtgaag attctggagg aagtggtccg gctgagagtc     480
gcagccaact ttagcactcc tgtgatctct accagtgatt cctctaatcc aggccaggag     540
cggacatata cttgcatgtc taagaacgga taccccgaac ctaatctgta ttggatcaac     600
accacagaca atagtctgat tgataccgct ctgcagaaca atacagtcta cctgaacaag     660
ctggggctgt atgacgtgat ctctactctg cggctgccat ggaccagtag aggagatgtg     720
ctgtgctgcg tggagaacgt ggccctgcac cagaatatca cctcaattag ccaggctgag     780
tcctttaccg gcaacaatac aaagaatcct caggagacac ataacaatga actgaaagtg     840
ctggtgccag tgctggccgt cctggctgca gcagcttttcg tgtctttat catctacaga     900 aggacccgcc ctcaccgctc atacactgga cctaagaccg tgcagctgga actgacagac     960
catgcttga                                                              969

<210> SEQ ID NO 33
```

<211> LENGTH: 909
<212> TYPE: DNA
<213> ORGANISM: Homo sapiens

<400> SEQUENCE: 33

```
atgcgtctgg gttcacctgg tctgctgttt ctgctgtttt caagtctgcg tgctgatact    60
caggagaagg aagtccgggc tatggtcgga agtgacgtgg agctgtcatg cgcttgtccc   120
gaagggtccc ggttcgacct gaacgatgtc tacgtgtatt ggcagacctc tgagagtaag   180
accgtggtca cataccacat ccctcagaac tccagcctgg aaaatgtgga ttcaaggtat   240
cggaacagag ccctgatgtc ccctgctggc atgctgcggg gagacttctc tctgagactg   300
tttaatgtga caccacagga tgagcagaaa ttccattgcc tggtcctgtc acagtccctg   360
ggatttcagg aggtgctgag tgtcgaagtg actctgcacg tcgccgctaa tttctccgtg   420
cctgtggtca gcgcaccaca tagcccctct caggacgagc tgacctttac atgtacttcc   480
atcaacggct accccgccc taacgtgtac tggattaaca agactgacaa tagcctgctg   540
gatcaggcac tgcagaacga caccgtgttt ctgaatatgc gaggactgta cgatgtggtc   600
agcgtcctgc gtattgccag gaccccatct gtgaacatcg ggtgctgtat tgagaacgtc   660
ctgctgcagc agaatctgac agtggggagc cagactggta atgacatcgg cgagagggat   720
aagattaccg aaaccccgt gagtacaggc gagaagaacg cagccacatg gtcaatcctg   780
gctgtgctgt cctgctggt ggtcgtggct gtcgcaattg ctgggtgtg ccgcgatcgg   840
tgtctgcagc actcttatgc cggtgcttgg gcagtgagtc cagagactga actgaccggc   900
catgtctaa                                                          909
```

<210> SEQ ID NO 34
<211> LENGTH: 1574
<212> TYPE: DNA
<213> ORGANISM: Mus musculus

<400> SEQUENCE: 34

```
cttaagatgg aaactgatac tctgctgctc tgggtgctgc tcctctgggt gcctggttca    60
actggggaca ttcgacgggc tgacattgtg atgacccaga ccacactgag cctgcccgtg   120
tccctgggcg accaggccag catctcctgc cggagctccc agtctatcgt gcacagcaac   180
ggaaacacat acctggagtg gtatctgcag aagcctggcc agtccccaaa gctgctgatc   240
tacaaggtgt ccaacaggtt cagcggcgtg cctgaccgct tttctggaag cggctccgga   300
acagatttca ccctgaagat cagcagggtg gaggctgagg acctgggcgt gtactactgc   360
ttccagggat cccacgtgcc ttacaccttt ggcggaggca aaagctgga gatcaagaga   420
gccgatgctg ctccaaccgt gtctggaagc ggaggcgggg ttctggagg cggtgggagc   480
ggtggcggag ggtctgaggc taagctgcag gagagcggcc ccgtgctggt gaagcctgga   540
gccagcgtga agatgtcctg taaggcttct ggatacacct tcacagacta ctacatgaac   600
tgggtgaagc agagccacgg caagtccctg gagtggatcg gagtgatcaa cccttacaac   660
ggcgacacct cttacaacca gaagtttaag ggcaaggcca ccctgacagt ggataagtct   720
agctccaccg cttacatgga gctgaacagc ctgacatccg aggattctgc cgtgtactac   780
tgtgctaggt actacggaag ctggttcgcc tactggggcc agggaacact gatcaccgtg   840
tccacagcca agaccacacc ccctagcgtg taccccctgg ctcctaggtc tagcagaggc   900
tgcaagccat gcatctgtac cgtgcccgag gtgagcagcg tgttcatctt ccacccaag   960
cccaaggacg tgctgaccat cacactgacc cctaaggtga catgcgtggt ggtggatatc  1020
```

```
agcaaggacg atccagaggt gcagttctcc tggtttgtgg acgatgtgga ggtgcacacc    1080
gcccagacac agccaaggga ggagcagttc aactccacct ttagatccgt gtctgagctg    1140
cccatcatgc accaggactg gctgaacgga aaggagttca agtgccgggt gaactccgcc    1200
gcttttcctg ctccaatcga aagaccatc tctaagacaa agggccgccc aaaggctcca     1260
caggtgtaca ccatccctcc acccaaggag cagatggcta aggataaggt gagcctgacc    1320
tgtatgatca cagacttctt tcccgaggat atcacagtgg agtggcagtg aacggacag     1380 cctgccgaga actacaagaa cacccagcca atcatggaca cagatggctc ttacttcgtg    1440
tacagcaagc tgaacgtgca gaagtctaac tgggaggctg caacaccttc acctgcagc    1500 gtgctgcacg aaggtctcca taatcaccac accgaaaaga gcctcagtca cagccctggg    1560
aaatgaggcg cgcc                                                      1574

<210> SEQ ID NO 35
<211> LENGTH: 1484
<212> TYPE: DNA
<213> ORGANISM: Homo sapiens

<400> SEQUENCE: 35
cttaagatgg aaactgacac cctgctgctg tgggtcctgc tgctgtgggt gcctggatcc      60
accggcgata tcgtgctgac ccagtctcct ggcacactga gtctgtcacc aggggagcga    120
gcaacactgt cttgtagagc cagccagtct gtgggaagct cctacctggc ttggtatcag    180
cagaagccag gccaggcacc caggctgctg atctacggag ccttcagccg ggccactggc    240
attccagaca ggttctctgg aagtggctca gggaccgact tcaccctgac catcagccga    300
ctggagcccg aagacttcgc cgtgtactat tgccagcagt acggctctag tccttggact    360
tttggacagg gcaccaaagt ggagatcaag cgcggcgggg gaggctctgg gggaggcggg    420
agtggaggcg ggggatcaca ggtccagctg gtggaaagcg gcgggggagt ggtccagcca    480
ggccggagcc tgcggctgag ctgcgccgct tcaggattca cattttcaag ctataccatg    540
cactgggtcc ggcaggcacc agggaaggga ctggagtggg tgaccttcat cagctatgac    600
ggcaacaaca agtattacgc tgattccgtg aaagggaggt ttaccattag ccgcgacaac    660
tccaaaaata cactgtacct gcagatgaac agcctgcggg ccgaggatac tgctatctac    720
tattgcgcaa gaaccgggtg gctgggaccc ttcgactatt ggggccaggg gactctggtc    780
accgtgtcct ctgataagac acacacatgc cctccctgtc ctgcaccaga gctgctgggc    840
gggccatccg tgttcctgtt tccacccaag cctaaagaca ccctgatgat cagccggaca    900
cctgaagtca cttgcgtggt cgtggacgtg agtcacgagg atccagaagt caagtttaac    960
tggtacgtga tggcgtcga ggtgcataat gccaagacca acctcgcga ggaacagtac    1020 aatagcacat atcgagtcgt gtccgtcctg actgtgctgc atcaggattg gctgaacggc    1080
aaagagtata agtgcaaagt gagcaataag gcactgcctg ccccaatcga gaaacaatt    1140 tccaaggcta aaggccagcc cagggaacct caggtgtaca ctctgcctcc aagtcgcgag    1200
gaaatgacca gaaccaggt gagcctgacc tgtctggtga agggttcta tccatcagac    1260 attgcagtgg agtgggaaag caatggacag cccgaaaaca attacaagac cacaccccct    1320
gtgctggaca gcgatggctc cttctttctg tattctaagc tgactgtgga taaaagtcgc    1380
tggcagcagg ggaacgtctt tagctgttcc gtgatgcatg aggctctgca caatcattac    1440
acacagaagt ctctgagtct gtcacccggc aaatgaggcg cgcc                    1484
```

<210> SEQ ID NO 36
<211> LENGTH: 632
<212> TYPE: DNA
<213> ORGANISM: Artificial Sequence
<220> FEATURE:
<223> OTHER INFORMATION: CMV promoter

<400> SEQUENCE: 36

```
gttgacattg attattgact agttattaat agtaatcaat tacgggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggagt atttacggta aactgcccac ttggcagtac     240
atcaagtgta tcatatgcca agtacgcccc ctattgacgt caatgacggt aaatggcccg     300
cctggcatta tgcccagtac atgaccttat gggactttcc tacttggcag tacatctacg     360
tattagtcat cgctattacc atggtgatgc ggttttggca gtacatcaat gggcgtggat     420
agcggtttga ctcacgggga tttccaagtc tccaccccat tgacgtcaat gggagtttgt     480
tttggcacca aaatcaacgg gactttccaa aatgtcgtaa caactccgcc ccattgacgc     540
aaatgggcgg taggcgtgta cggtgggagg tctatataag cagagctctc tggctaacta     600
gagaacccac tgcttactgg cttatcgaaa tt                                   632
```

<210> SEQ ID NO 37
<211> LENGTH: 394
<212> TYPE: DNA
<213> ORGANISM: Artificial Sequence
<220> FEATURE:
<223> OTHER INFORMATION: RSV promoter

<400> SEQUENCE: 37

```
tgtacgggcc agatatacgc gtatctgagg ggactagggt gtgtttaggc gaaaagcggg      60
gcttcggttg tacgcggtta ggagtccccct caggatatag tagtttcgct tttgcatagg    120
gagggggaaa tgtagtctta tgcaatacac ttgtagtctt gcaacatggt aacgatgagt     180
tagcaacatg ccttacaagg agagaaaaag caccgtgcat gccgattggt ggaagtaagg     240
tggtacgatc gtgccttatt aggaaggcaa cagacaggtc tgacatggat tggacgaacc     300
actgaattcc gcattgcaga gataattgta tttaagtgcc tagctcgata caataaacgc     360
catttgacca ttcaccacat tggtgtgcac ctcc                                 394
```

<210> SEQ ID NO 38
<211> LENGTH: 188
<212> TYPE: DNA
<213> ORGANISM: Artificial Sequence
<220> FEATURE:
<223> OTHER INFORMATION: BGH polyA

<400> SEQUENCE: 38

```
ctgtgccttc tagttgccag ccatctgttg tttgccccctc ccccgtgcct tccttgaccc     60
tggaaggtgc cactcccact gtcctttcct aataaaatga ggaaattgca tcgcattgtc    120
tgagtaggtg tcattctatt ctggggggtg ggtggggca ggacagcaag ggggaggatt     180
gggaagac                                                              188
```

<210> SEQ ID NO 39
<211> LENGTH: 249
<212> TYPE: DNA
<213> ORGANISM: Artificial Sequence
<220> FEATURE:
<223> OTHER INFORMATION: SV40 late polyA

<400> SEQUENCE: 39

| | | | | | |
|---|---|---|---|---|---|
| gacatgataa | gatacattga | tgagtttgga | caaaccacaa | ctagaatgca | gtgaaaaaaa | 60 |
| tgctttattt | gtgaaatttg | tgatgctatt | gctttatttg | tgaaatttgt | gatgctattg | 120 |
| ctttatttgt | aaccattata | agctgcaata | aacaagttaa | caacaacaat | tgcattcatt | 180 |
| ttatgtttca | ggttcagggg | gaggtgtggg | aggttttttta | aagcaagtaa | aacctctaca | 240 |
| aatgtggta | | | | | | 249 |

<210> SEQ ID NO 40
<211> LENGTH: 345
<212> TYPE: DNA
<213> ORGANISM: Artificial Sequence
<220> FEATURE:
<223> OTHER INFORMATION: SV40 enhancer promoter

<400> SEQUENCE: 40

| | | | | | |
|---|---|---|---|---|---|
| gctgtggaat | gtgtgtcagt | tagggtgtgg | aaagtcccca | ggctccccag | caggcagaag | 60 |
| tatgcaaagc | atgcatctca | attagtcagc | aaccaggtgt | ggaaagtccc | caggctcccc | 120 |
| agcaggcaga | agtatgcaaa | gcatgcatct | caattagtca | gcaaccatag | tcccgcccct | 180 |
| aactccgccc | atcccgcccc | taactccgcc | cagttccgcc | cattctccgc | cccatggctg | 240 |
| actaattttt | tttatttatg | cagaggccga | ggccgcctcg | gcctctgagc | tattccagaa | 300 |
| gtagtgagga | ggcttttttg | gaggcctagg | cttttgcaaa | aagct | | 345 |

<210> SEQ ID NO 41
<211> LENGTH: 99
<212> TYPE: DNA
<213> ORGANISM: Artificial Sequence
<220> FEATURE:
<223> OTHER INFORMATION: Rabbit beta-globin polyA

<400> SEQUENCE: 41

| | | | | | |
|---|---|---|---|---|---|
| gacctctggc | taataaagga | aatttatttt | cattgcaata | gtgtgttgga | attttttgtg | 60 |
| tctctcactc | ggaaggacat | atgggagggc | aaatcattt | | | 99 |

<210> SEQ ID NO 42
<211> LENGTH: 723
<212> TYPE: DNA
<213> ORGANISM: Artificial Sequence
<220> FEATURE:
<223> OTHER INFORMATION: GFP

<400> SEQUENCE: 42

| | | | | | |
|---|---|---|---|---|---|
| accatggtga | gcaagggcga | ggagctgttc | accggggtgg | tgcccatcct | ggtcgagctg | 60 |
| gacggcgacg | taaacggcca | caagttcagc | gtgtccggcg | agggcgaggg | cgatgccacc | 120 |
| tacggcaagc | tgaccctgaa | gttcatctgc | accaccggca | agctgcccgt | gccctggccc | 180 |
| accctcgtga | ccaccctgac | ctacggcgtg | cagtgcttca | gccgctaccc | cgaccacatg | 240 |
| aagcagcacg | acttcttcaa | gtccgccatg | cccgaaggct | acgtccagga | gcgcaccatc | 300 |
| ttcttcaagg | acgacggcaa | ctacaagacc | cgcgccgagg | tgaagttcga | gggcgacacc | 360 |
| ctggtgaacc | gcatcgagct | gaagggcatc | gacttcaagg | aggacggcaa | catcctgggg | 420 |
| cacaagctgg | agtacaacta | caacagccac | aacgtctata | tcatggccga | caagcagaag | 480 |
| aacggcatca | aggtgaactt | caagatccgc | cacaacatcg | aggacggcag | cgtgcagctc | 540 |

```
gccgaccact accagcagaa caccccatc ggcgacggcc ccgtgctgct gcccgacaac      600
cactacctga gcacccagtc cgccctgagc aaagacccca cgagaagcg cgatcacatg      660 gtcctgctgg agttcgtgac cgccgccggg atcactctcg gcatggacga gctgtacaag    720
taa                                                                  723

<210> SEQ ID NO 43
<211> LENGTH: 454
<212> TYPE: DNA
<213> ORGANISM: Artificial Sequence
<220> FEATURE:
<223> OTHER INFORMATION: MoMuLV LTR

<400> SEQUENCE: 43
ttaattaagt aacgccattt tgcaaggcat ggaaaaatac ataactgaga atagagaagt      60
tcagatcaag gtcaggaaca gatggaacag ctgaatatgg gccaaacagg atatctgtgg    120
taagcagttc ctgccccggc tcagggccaa gaacagatgg aacagctgaa tatgggccaa    180
acaggatatc tgtggtaagc agttcctgcc ccggctcagg gccaagaaca gatggtcccc    240
agatgcggtc cagccctcag cagtttctag agaaccatca gatgtttcca gggtgcccca    300
aggacctgaa atgaccctgt gccttatttg aactaaccaa tcagttcgct tctcgcttct    360
gttcgcgcgc ttctgctccc cgagctcaat aaaagagccc acaacccctc actcggggcg    420
ccagtcctcc gattgactga gtcgcccgct taag                                454

<210> SEQ ID NO 44
<211> LENGTH: 1349
<212> TYPE: DNA
<213> ORGANISM: Artificial Sequence
<220> FEATURE:
<223> OTHER INFORMATION: EF1alpha promoter

<400> SEQUENCE: 44
ttaattaaga gtaattcata caaaaggact cgcccctgcc ttggggaatc ccagggaccg      60
tcgttaaact cccactaacg tagaacccag agatcgctgc gttcccgccc cctcacccgc    120
ccgctctcgt catcactgag gtggagaaga gcatgcgtga ggctccggtg cccgtcagtg    180
ggcagagcgc acatcgccca cagtccccga aagttggggg gaggggtcg gcaattgaac    240 cggtgcctag agaaggtggc gcggggtaaa ctgggaaagt gatgtcgtgt actggctccg    300
cctttttccc gagggtgggg gagaaccgta tataagtgca gtagtcgccg tgaacgttct    360
ttttcgcaac gggtttgccg ccagaacaca ggtaagtgcc gtgtgtggtt cccgcgggcc    420
tggcctcttt acgggttatg gcccttgcgt gccttgaatt acttccacgc cctggctgc    480 agtacgtgat tcttgatccc gagcttcggg ttggaagtgg gtgggagagt tcgaggcctt    540
gcggttaagg agccccttcg cctcgtgctt gagttgaggc ctggcttggg cgctggggcc    600
gccgcgtgcg aatctggtgg caccttcgcg cctgtctcgc tgctttcgat aagtctctag    660
ccatttaaaa ttttttgatga cctgctgcga cgctttttt ctggcaagat agtcttgtaa    720
atgcgggcca agatctgcac actggtattt cggtttttgg ggccgcgggc ggcgacgggg    780
cccgtgcgtc ccagcgcaca tgttcggcga ggcgggcct gcgagcgcgg ccaccgagaa    840
tcggacgggg gtagtctcaa gctggccggc ctgctctggt gcctggcctc gcgccgccgt    900
gtatcgcccc gccctgggcg gcaaggctgg cccggtcggc accagttgcg tgagcggaaa    960 gatgccgct tcccgccct gctgcaggga gctcaaaatg gaggacgcgg cgctcggag     1020 agcgggcggg tgagtcaccc acacaaagga aaagggcctt tccgtcctca gccgtcgctt    1080
```

```
catgtgactc cacggagtac cgggcgccgt ccaggcacct cgattagttc tcgagctttt    1140
ggagtacgtc gtctttaggt tggggggagg ggttttatgc gatggagttt ccccacactg    1200
agtgggtgga gactgaagtt aggccagctt ggcacttgat gtaattctcc ttggaatttg    1260 cccttttttga gtttggatct tggttcattc tcaagcctca gacagtggtt caaagttttt    1320
ttcttccatt tcaggtgtcg tgacttaag                                       1349

<210> SEQ ID NO 45
<211> LENGTH: 481
<212> TYPE: DNA
<213> ORGANISM: Artificial Sequence
<220> FEATURE:
<223> OTHER INFORMATION: HGH polyA

<400> SEQUENCE: 45
gacgggtggc atccctgtga cccctcccca gtgcctctcc tggccctgga agttgccact      60
ccagtgccca ccagccttgt cctaataaaa ttaagttgca tcattttgtc tgactaggtg     120
tccttctata atattatggg gtggaggggg gtggtatgga gcaaggggca agttgggaag     180
acaacctgta gggcctgcgg ggtctattgg gaaccaagct ggagtgcagt ggcacaatct     240
tggctcactg caatctccgc ctcctgggtt caagcgattc tcctgcctca gcctcccgag     300
ttgttgggat tccaggcatg catgaccagg ctcagctaat ttttgttttt ttggtagaga     360
cggggtttca ccatattggc caggctggtc tccaactcct aatctcaggt gatctaccca     420
ccttggcctc ccaaattgct gggattacag gcgtgaacca ctgctccctt ccctgtcctt     480
t                                                                     481
```

ONCOLYTIC VIRUS STRAIN

CROSS-REFERENCE TO RELATED APPLICATION

This application is a national phase under 35 U.S.C. § 371 of International Application No. PCT/GB2017/050037, filed Jan. 9, 2017, which claims the benefit of priority to Great Britain Patent Application Serial Nos. 1600380.8, 1600381.6, and 1600382.4, all filed Jan. 8, 2016,the entire contents of each of which are hereby incorporated by reference in their entirety.

FIELD OF THE INVENTION

The invention relates to an oncolytic immunotherapeutic agent and to the use of the oncolytic immunotherapeutic agent in treating cancer.

BACKGROUND TO THE INVENTION

Viruses have a unique ability to enter cells at high efficiency. After entry into cells, viral genes are expressed and the virus replicates. This usually results in the death of the infected cell and the release of the antigenic components of the cell as the cell ruptures as it dies. As a result, virus mediated cell death tends to result in an immune response to these cellular components, including both those derived from the host cell and those encoded by or incorporated into the virus itself.

Viruses also engage with various mediators of the innate immune response as part of the host response to the recognition of a viral infection through e.g. toll-like receptors and cGAS/STING signalling resulting in the activation of interferon responses and inflammation which are also immunogenic signals to the host. These immune responses may result in the immunogenic benefit to cancer patients such that immune responses to tumor antigens provide a systemic overall benefit resulting in the treatment of tumors which have not been infected with the virus, including micrometastatic disease, and providing vaccination against relapse.

The combined direct ('oncolytic') effects of the virus, and immune responses against tumor antigens (including non-self 'neo-antigens', i.e. derived from the particular mutated genes in individual tumors) is termed 'oncolytic immunotherapy'.

Viruses may also be used as delivery vehicles ('vectors') to express heterologous genes inserted into the viral genome in infected cells. These properties make viruses useful for a variety of biotechnology and medical applications. For example, viruses expressing heterologous therapeutic genes may be used for gene therapy. In the context of oncolytic immunotherapy, delivered genes may include those encoding specific tumor antigens, genes intended to increase the immunogenicity of antigens released following virus replication and cell death, to increase the general immune activation status of the tumor, or to increase the direct oncolytic properties (i.e. cytotoxic effects) of the virus.

It has been demonstrated that a number of viruses including herpes simplex virus (HSV) have utility in the oncolytic treatment of cancer. HSV for use in the oncolytic treatment of cancer must be disabled such that it is no longer pathogenic, but can still enter into and kill tumor cells. A number of disabling mutations to HSV, including disruption of the genes encoding ICP34.5, ICP6, and/or thymidine kinase, have been identified which do not prevent the virus from replicating in culture or in tumor tissue in vivo, but which prevent significant replication in normal tissue. HSVs in which only the ICP34.5 genes have been disrupted replicate in many tumor cell types in vitro, and replicate selectively in tumor tissue, but not in surrounding tissue, in mouse tumor models. Clinical trials of ICP34.5 deleted, or ICP34.5 and ICP6 deleted, HSV have also shown safety and selective replication in tumor tissue in man.

As discussed above, an oncolytic virus, including HSV, may also be used to deliver a therapeutic gene in the treatment of cancer. An ICP34.5 deleted virus of this type additionally deleted for ICP47 and encoding a heterologous gene for GM-CSF has also been tested in clinical trials, including a phase 3 trial in melanoma in which safety and efficacy in man was shown. The trial data demonstrated that tumor responses could be seen in injected tumors, and to a lesser extent in uninjected tumors. Responses tended to be highly durable (months-years), and a survival benefit appeared to be achieved in responding patients. Each of these indicated engagement of the immune system in the treatment of cancer in addition to the direct oncolytic effect. However, this and other data with oncolytic viruses generally showed that not all tumors respond to treatment and not all patients achieve a survival advantage. Thus, improvements to the art of oncolytic therapy and oncolytic immunotherapy are clearly needed. These may serve to increase the direct oncolytic effects of therapy, the anti-tumor immune stimulating effects of the therapy, or both of these effects together.

Recently it has been shown that oncolytic immunotherapy can result in additive or synergistic therapeutic effects in conjunction with immune checkpoint blockade (i.e. inhibition or 'antagonism' of immune checkpoint pathways), also referred to as immune co-inhibitory pathway blockade. Checkpoint (immune co-inhibitory pathway) blockade is intended to block host immune inhibitory mechanisms which usually serve to prevent the occurrence of autoimmunity. However, in cancer patients these mechanisms can also serve to inhibit or block the potentially beneficial effects of any immune responses induced to tumors. Alternatively, immune responses may not be fully potentiated due to a lack of activation or lack of full activation of immune potentiating pathways. Therefore, drugs which alleviate these blocks or stimulate immune potentiating pathways (i.e. which activate, or are 'agonists' of these immune potentiating pathways) are attractive for testing and developing cancer treatments. Targets for such approved or experimental drugs include CTLA-4, PD-1, PD-L1, LAG-3, TIM-3, VISTA, CSF1R, IDO, CEACAM1, GITR, 4-1-RB, KIR, SLAMF7, OX40, CD40, ICOS or CD47.

For these approaches to be successful, pre-existing immune responses to tumors are needed, i.e. so that a pre-existing immune response can be potentiated or a block to an anti-tumor immune response can be relieved. The presence of an inflamed tumor micro-environment, which is indicative of such an ongoing response, is also needed. Pre-existing immune responses to tumor neo-antigens appear to be particularly important for the activity of immune co-inhibitory pathway blockade and related drugs. Only some patients may have an ongoing immune response to tumor antigens including neoantigens and/or an inflamed tumor microenvironment, both of which are required for the activity of these drugs. Therefore, oncolytic agents which can induce immune responses to tumor antigens, including neoantigens, and/or which can induce an inflamed tumor microenvironment are attractive for use in combination with immune co-inhibitory pathway blockade and immune potentiating drugs. This likely also explains the promising combined anti-tumor effects of oncolytic agents and immune co-inhibitory pathway blockade in mice and humans that have so far been observed.

The indoleamine 2,3-dioxygenase (IDO) pathway contributes to tumor-induced tolerance by creating a tolerogenic environment in the tumor and the tumor-draining lymph nodes, both by direct suppression of T cells and enhancement of local regulatory T cell (Treg)-mediated immunosuppression. IDO catalyses the rate-limiting step of tryptophan degradation along the kynurenine pathway, and both the reduction in local tryptophan concentration and the production of immunomodulatory tryptophan metabolites contribute to the immunosuppressive effects of IDO. IDO is chronically activated in many cancer patients with IDO activation correlating with more extensive disease. It can also function as an antagonist to other activators of antitumor immunity. Therefore, inhibitors of the IDO pathway are being developed as anticancer agents, particularly in combination with checkpoint blockade agents such as those which target CTLA-4, PD-1 or PDL-1. IDO inhibitors may also be synergistic with oncolytic immunotherapy, including together with drugs targeting other immune checkpoint or immune co-stimulatory pathways.

SUMMARY OF THE INVENTION

The invention provides improved oncolytic viruses. The improved oncolytic viruses have improved direct oncolytic effects. The improved direct oncolytic effects provided by the viruses of the invention will also lead to improved systemic anti-tumor immune effects. The improved direct oncolytic effects provided by the viruses of the invention will also lead to improved therapeutic effects in patients. Enhanced replication in and killing of tumor cells will result in enhanced tumor antigen release and enhanced systemic immune responses to the released antigens. The expression levels of any genes inserted to augment the direct oncolytic effects and/or immune stimulation will also be increased.

Virus species naturally exist in a range of variants (strains) within the natural population which may differ by a small or larger number of nucleotides while still retaining the antigenic characteristics and sufficient sequence identity to still be recognized as the same virus species. These strains, due to their differing sequences, may exhibit a range of differing properties, including properties which have been selected for by natural selection in their natural host or hosts (for example the ability to infect or replicate in the target cell types of the virus in question, spread between these cells, or to evade the host innate or adaptive immune system, or to spread between infected individuals of the host species) and properties which have not been specifically selected for (e.g. the ability to replicate in and kill or spread between cell types which are not the natural targets of the virus in question, including tumor or other non-target cell types or tissues). The inventors have recognised that sampling a range of viral strains of a particular viral species which are present in the natural host population (in the case of viruses infecting humans, here termed 'clinical isolates') and comparing these to each other to select for the strain with the best properties for the intended purpose for which it is to be used (e.g. infection and killing of tumor cells) can be used to identify a virus (i.e. a virus strain) with optimal properties for that purpose. The optimal properties may be properties that offer the best starting point for development to produce a virus that can be used as a therapeutic. A virus identified by this approach is likely to have more optimal properties for the intended purpose than a 'prototype' or 'laboratory' virus strain or a clinical strain which has not been selected for the required property or properties from a broad group of viral strains. This is because the full biological complexity in the natural population, particularly with respect to the particular desirable property or properties, is unlikely to have been sampled through taking a narrow approach to screening for the desired property or properties, bearing in mind the degree of sequence variation present in natural virus populations. In particular, these may vary in sequence within an infected host (as is often the case with RNA or retroviral populations where so-called quasi-species are often present), between individual infected hosts, or between different geographically separated viral populations.

Viruses of the invention have therefore been selected by sampling a range of viral strains present in the natural population of a particular viral species and testing these against each other for the desired property or properties (e.g. the ability to infect and kill tumor cells). The virus strain or strains with the best properties for the intended purpose are used for further development.

Where the intended use is oncolytic viral therapy, taking such an approach provides an improved starting point for development of an oncolytic agent, which may require further manipulation of the advantageous virus strains. Such manipulation includes the deletion of viral genes to provide, for example, tumor selectivity, and/or the insertion of exogenous genes to improve oncolytic or immune potentiating properties further.

The viruses of the invention therefore include novel clinical isolates of a viral species that have better anti-tumor effects than the other clinical isolates to which they were compared and through which comparison they were identified. In particular, the clinical isolates of the invention kill tumor cell lines in vitro more quickly and/or at a lower dose than these reference clinical isolates of the same virus type. Typically, a clinical isolate of the invention will have been identified through comparison of >5 clinical isolates of a viral species for the required property or properties, preferably through comparison of >10 clinical isolates of the viral species, and more preferably through comparison of >20 clinical isolates of the viral species. A clinical isolate of the invention typically shows better tumor cell killing activity than $3/5$, $6/10$ or $11/20$ths, preferably better than $4/5$, $8/10$ or $17/20$ths, more preferably better than $9/10$ or $19/20$ths of the viral strains tested.

Typically, a clinical isolate of the invention can kill two or more tumor cell lines in vitro within 24 to 48 hours after infection at a multiplicity of infection (MOI) of 0.01 to 0.001 or less.

The clinical isolates of the invention may be modified to further enhance their anti-tumor effects. The genome of a clinical isolate of the invention may be modified to delete or alter expression of one or more viral genes, and/or the genome of the clinical isolate may be modified to express one or more heterologous genes, such as genes encoding a fusogenic protein and/or an immune stimulatory molecule or molecules.

Oncolytic viruses of the invention provide improved treatment of cancer through improved direct oncolytic effects, viral replication and spread through tumors, which (i) increases the amount of tumor antigens, including neoantigens, which are released for the induction of an anti-tumor immune response; and (ii) enhances the expression of the virus-encoded immune stimulatory molecule(s). Expression of immune stimulatory molecule(s) by the virus can further enhance and potentiate the anti-tumor immune effect.

Expression of fusogenic protein(s) by the virus can further enhance viral spread through tumors. Expression of fusogenic protein(s) by the virus can further enhance tumor cell killing.

Anti-tumor efficacy of an oncolytic virus of the invention is achieved when the virus is used as a single agent and also when the virus is used in combination with other anti-cancer modalities, including chemotherapy, treatment with targeted agents, radiation, immune checkpoint blockade (i.e. administration of one or more antagonist of an immune co-inhibitory pathway) and/or immune potentiating drugs (e.g.one or more agonists of an immune co-stimulatory pathway). The improved direct oncolytic effects (i.e. virus replication in, spread between, and direct killing of tumor cells) and improved systemic anti-tumor immune effects of the viruses of the invention improve on the combined benefits of oncolytic therapy and immune co-inhibitory pathway blockade and/or immune co-stimulatory pathway activation.

Accordingly, the present invention provides an oncolytic virus which is, or is derived from, a clinical isolate which has been selected by comparing the abilities of a panel of three or more clinical isolates of the same viral species to kill tumor cells of two or more tumor cell lines in vitro and selecting a clinical isolate which is capable of killing cells of two or more tumor cell lines more rapidly and/or at a lower dose in vitro than one or more of the other clinical isolates in the panel. The clinical isolate may be modified. A modified clinical isolate may have mutations, such as deletions in the viral genome and/or may express one or more heterologous genes.

The virus may be a strain of any virus species which may be used for the oncolytic treatment of cancer, including strains of herpes virus, pox virus, adenovirus, retrovirus, rhabdovirus, paramyxovirus or reovirus. The virus is preferably a herpes simplex virus (HSV), such as HSV1. The HSV typically does not express functional ICP34.5 and/or functional ICP47 and/or expresses the US11 gene as an immediate early gene.

The virus may comprise (i) a fusogenic protein-encoding gene; and/or (ii) an immune stimulator) molecule or an immune stimulatory molecule-encoding gene. The virus may encode more than one fusogenic protein andlor more than one immune stimulatory molecule. The fusogenic protein is preferably the glycoprotein from gibbon ape leukemia virus (GALV) and has the R transmembrane peptide mutated or removed (GALV-R-). The immune stimulatory molecule is preferably GM-CSF and/or an agonist of an immune co-stimulatory pathway including GITRL, 4-1-BBL, OX40L, ICOSL or CD40L, or a modified version in each case thereof, or a protein capable of blocking signaling through CTLA-4, for example an antibody or a fragment thereof which binds CTLA-4.

The invention also provides:
a pharmaceutical composition comprising a virus of the invention and a pharmaceutically acceptable carrier or diluent;
the virus of the invention fhr use in a method of treating the human or animal body by therapy;
the virus of the invention for use in a method of treating cancer, wherein the method optionally comprises administering a further anti-cancer agent;
a product of manufacture comprising a virus of the invention in a sterile vial, ampoule or syringe;
a method of treating cancer, which comprises administering a therapeutically effective amount of a virus or a pharmaceutical composition of the invention to a patient in need thereof, wherein the method optionally comprises administering a further anti-cancer agent;
use of a virus of the invention in the manufacture of a medicament for use in a method of treating cancer, wherein the method optionally comprises administering a further anti-cancer agent, which is optionally an antagonist of an immune co-inhibitory pathway, or an agonist of an immune co-stimulatory pathway;
a method of treating cancer, which comprises administering a therapeutically effective amount of an oncolytic virus, an inhibitor of the indoleamine 2,3-dioxygenase (IDO) pathway and a further antagonist of an immune co-inhibitory pathway, or agonist of an immune co-stimulatory pathway to a patient in need thereof; and
a method of selecting an oncolytic virus, the method comprising:
  (i) comparing the abilities of a panel of three or more clinical isolates of the same viral strain to kill tumor cells of two or more tumor cell lines in vitro;
  (ii) scoring the abilities of each of the panel of viruses to kill tumor cells;
  (iii) selecting a virus which has one of the best scores;
  (iv) optionally modifying the virus to inactivate one or more viral genes; and/or
  (v) optionally modifying the virus to express one or more immune stimulatory molecule encoding genes and/or one or more fusogenic protein-encoding genes.

The further anti-cancer agent may be an antagonist of an immune co-inhibitory pathway or an agonist of an immune co-stimulatory pathway.

BRIEF DESCRIPTION OF THE FIGURES

FIG. 1 also shows similar exemplary viruses of the invention expressing only a GALV-R-encoding gene (second panel), or only a GM-CSF-encoding gene (third panel) Also shown is an exemplary virus in which the ICP34.5 gene and the ICP47 gene are deleted.

FIG. 6 shows the results of an ELISA to detect expression of human or mouse GM-CSF in supernatants from BHK cells infected with virus 16 (mGM-CSF and GALVR-), virus 17 (hGM-CSF and GALVR-) and virus 19 (mGM-CSF).

FIG. 7 is a comparison between the cell-killing abilities of strain RH018A in which ICP34.5 is deleted and which expresses GALVR- and GFP (virus 10) with a virus that expresses only GFP (virus 12) as determined by crystal violet staining in three cell lines at low magnification.

FIG. 11 shows the antitumor effects of Virus 16 in Balb/c mice harboring mouse CT26 tumors in the left and right flanks. Groups of 10 mice were then treated with: Vehicle (3 injections into right flank tumors every other day); 5×10exp6 pfu of Virus 16 (mRP1) injected in the right flank tumor every other day; anti-mouse PD1 alone (10 mg/kg i.p. every three days, BioXCell clone RMP1-14); anti-mouse CTLA-4 (3 mg/kg i.p every three days, BioXCell clone 9D9); anti-mouse PD1 together with Virus 16; anti-mouse CTLA4 together with Virus 16; 1-methyl trypotophan (I-MT; IDO inhibitor (5 mg/ml in drinking water)); anti-mouse PD1 together with 1-methyl trypotophan; or anti-mouse PD1 together with 1-methyl trypotophan and Virus 16. Effects on tumor size were observed for a further 30 days. Greater tumor reduction was seen in animals treated with combinations of virus and checkpoint bockade than with the single treatment groups. FIG. 11A shows that using Virus 16 and anti-PD1 in combination has a better anti-tumor effect than using either anti-PD1 or the virus alone. FIG. 11B shows that the anti-tumor effect of Virus 16 in combination with anti-CTLA-4 was better than the anti-tumor effect of either Virus 16 or anti-CTLA-4 alone. FIG. 11C shows that enhanced tumor reduction was observed using Virus 16 together with both anti-PD1 and IDO inhibition as compared to anti-PD1 and 1-MT inhibition in the absence of the virus.

BRIEF DESCRIPTION OF THE SEQUENCE LISTING

Figure 1:
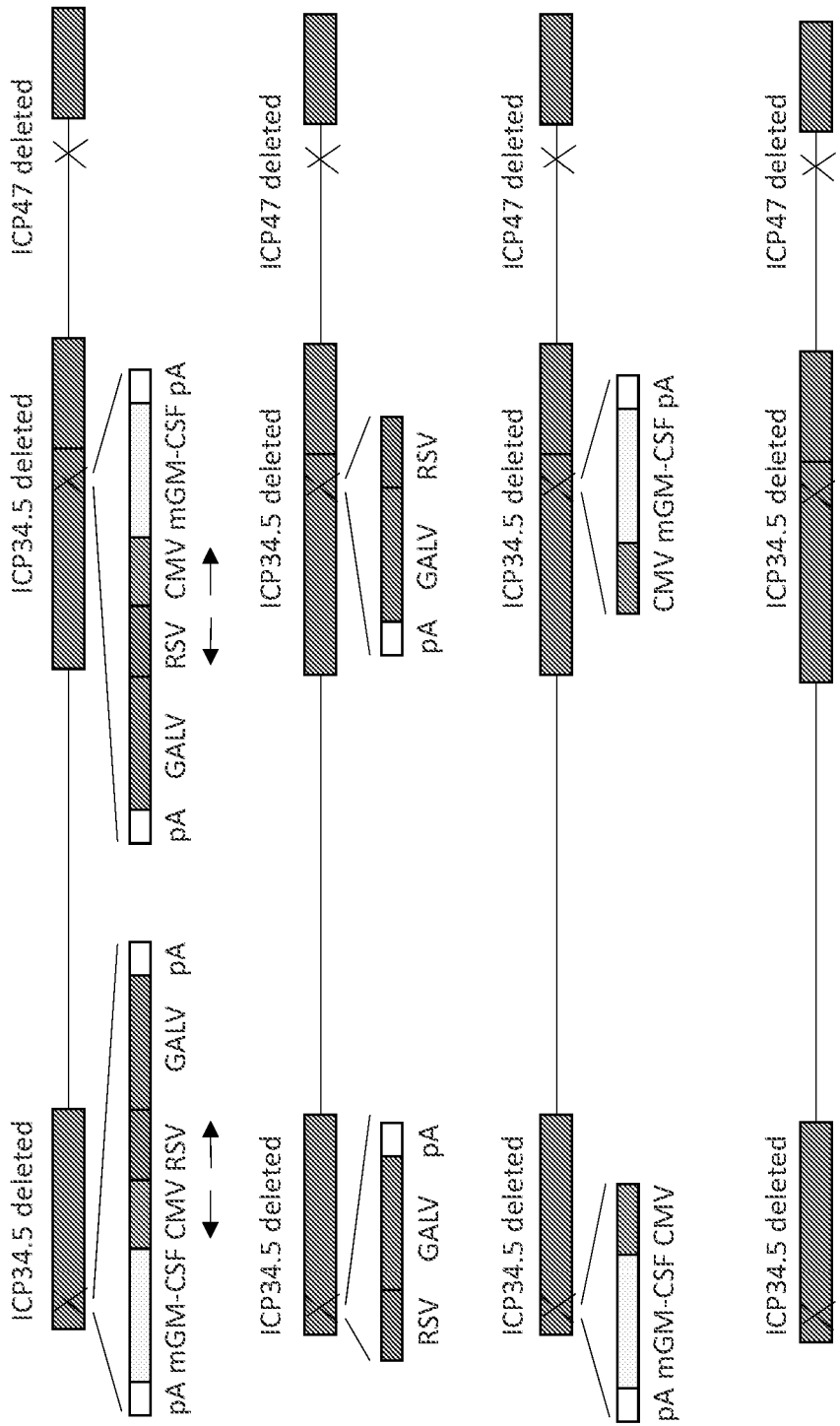
FIG. 1 depicts the structure of an exemplary virus of the invention that comprises a gene encoding GALV-R- and a gene encoding GM-CSF inserted into the ICP34.5 gene locus, and in which the ICP47 gene is deleted such that the US11 gene is under the control of the ICP47 immediate early promoter (top panel).
Figure 2:
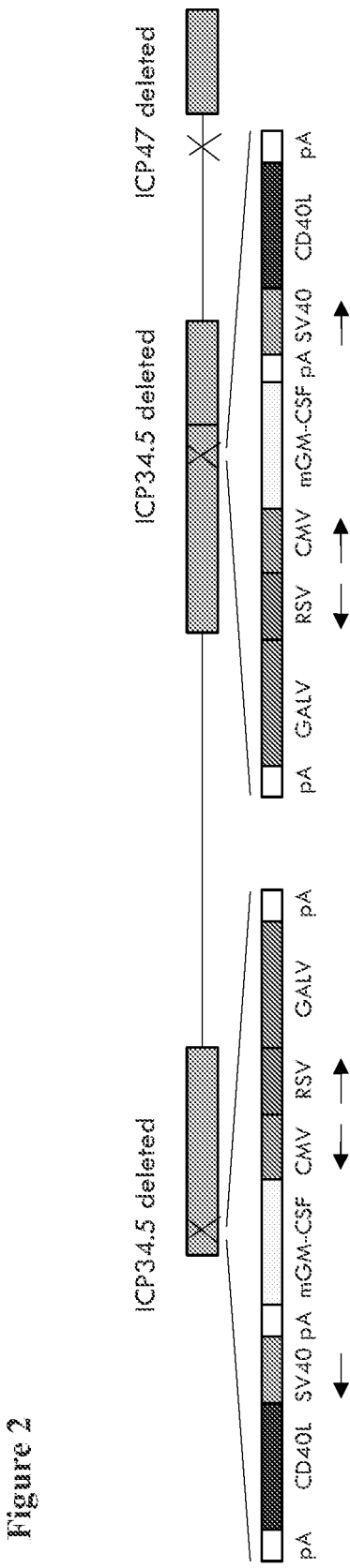
FIG. 2 depicts the structure of an exemplary virus of the invention that comprises a gene encoding GALV-R-, a gene encoding GM-CSF and a gene encoding CD40L.

SEQ ID NO: 1 is the nucleotide sequence of mouse GM-CSF.

SEQ ID NO: 2 is the nucleotide sequence of a codon optimized version of mouse GM-CSF.

SEQ ID NO: 3 is the nucleotide sequence of human GM-CSF.

SEQ ID NO: 4 is the nucleotide sequence of a codon optimized version of human GM-CSF.

SEQ ID NO: 5 is the amino acid sequence of mouse GM-CSF.

SEQ ID NO: 6 is the amino acid sequence of human GM-CSF.

SEQ ID NO: 7 is the nucleotide sequence of GALV-R-.

SEQ ID NO: 8 is the nucleotide sequence of a codon optimized version of GALV-R- (the first three nucleotides are optional).

SEQ ID NO: 9 is the amino acid sequence of GALV-R-.

SEQ ID NO: 10 is the nucleotide sequence of a codon optimized version of a human membrane bound version of CD40L.

SEQ ID NO: 11 is the amino acid sequence of a human membrane bound version of CD40L.

SEQ ID NO: 12 is the nucleotide sequence of a codon optimized version of a multimeric secreted version of human CD40L.

SEQ ID NO: 13 is the amino acid sequence of a multimeric secreted version of human CD40L.

SEQ ID NO: 14 is the nucleotide sequence of a codon optimized version of a multimeric secreted version of mouse CD40L.

SEQ ID NO: 15 is the amino acid sequence of a multimeric secreted version of mouse CD40L.

SEQ ID NO: 16 is a codon optimized version of the nucleotide sequence of wild-type human CD40L.

SEQ ID NO: 17 is the amino acid sequence of wild-type human CD40L.

SEQ ID NO: 18 is a codon optimized version of the nucleotide sequence of wild-type mouse CD40L.

SEQ ID NO: 19 is the amino acid sequence of wild-type mouse CD40L.

SEQ ID NO: 20 is the nucleotide sequence of a codon optimized version of murine 4-1BBL.

SEQ ID NO: 21 is the nucleotide sequence of a codon optimized version of human 4-1BBL.

SEQ ID NO: 22 is the nucleotide sequence of a codon optimized version of secreted mouse 4-1BBL.

SEQ ID NO: 23 is the nucleotide sequence of a codon optimized version of human secreted 4-1BBL.

SEQ ID NO: 24 is the nucleotide sequence of a codon optimized version of murine GITRL.

SEQ ID NO: 25 is the nucleotide sequence of a codon optimized version of human GITRL.

SEQ ID NO: 26 is the nucleotide sequence of a codon optimized version of secreted murine GITRL.

SEQ ID NO: 27 is the nucleotide sequence of a codon optimized version of secreted human GITRL.

SEQ ID NO: 28 is the nucleotide sequence of a codon optimized version of murine OX40L.

SEQ ID NO: 29 is the nucleotide sequence of a codon optimized version of human OX40L.

SEQ ID NO: 30 is the nucleotide sequence of a codon optimized version of secreted murine OX40L.

SEQ ID NO: 31 is the nucleotide sequence of a codon optimized version of secreted human OX40L.

SEQ ID NO: 32 is the nucleotide sequence of a codon optimized version of murine ICOSL.

SEQ ID NO: 33 is the nucleotide sequence of a codon optimized version of human ICOSL.

SEQ ID NO: 34 is the nucleotide sequence of a murine scFv CTLA-4 antibody. The first six and last eight nucleotides are restriction sites added for cloning purposes.

SEQ ID NO: 35 is the nucleotide sequence of a murine scFv CTLA-4 antibody. The first six and last eight nucleotides are restriction sites added for cloning purposes.

SEQ ID NO: 36 is the nucleotide sequence of the CMV promoter.

SEQ ID NO: 37 is the nucleotide sequence of the RSV promoter.

SEQ ID NO: 38 is the nucleotide sequence of BGH polyA.

SEQ ID NO: 39 is the nucleotide sequence of SV40 late polyA.

SEQ ID NO: 40 is the nucleotide sequence of the SV40 enhancer promoter.

SEQ ID NO: 41 is the nucleotide sequence of rabbit beta-globulin (RBG) polyA.

SEQ ID NO: 42 is the nucleotide sequence of GFP.

SEQ ID NO: 43 is the nucleotide sequence of the MoMuLV LTR promoter.

SEQ ID NO: 44 is the nucleotide sequence of the EF1a promoter.

SEQ ID NO: 45 is the nucleotide sequence of HGH polyA.

DETAILED DESCRIPTION OF THE INVENTION

Oncolytic Virus

The virus of the invention is oncolytic. An oncolytic virus is a virus that infects and replicates in tumor cells, such that the tumor cells are killed. Therefore, the virus of the invention is replication competent. Preferably, the virus is selectively replication competent in tumor tissue. A virus is selectively replication competent in tumor tissue if it replicates more effectively in tumor tissue than in non-tumor tissue. The ability of a virus to replicate in different tissue types can be determined using standard techniques in the art.

The virus of the invention may be any virus which has these properties, including a herpes virus, pox virus, adenovirus, retrovirus, rhabdovirus, paramyxovirus or reovirus, or any species or strain within these larger groups. Viruses of the invention may be wild type (i.e. unaltered from the parental virus species), or with gene disruptions or gene additions. Which of these is the case will depend on the virus species to be used. Preferably the virus is a species of herpes virus, more preferably a strain of HSV, including strains of HSV1 and HSV2, and is most preferably a strain of HSV1. The virus of the invention is based on a clinical isolate of the virus species to be used. The clinical isolate is selected on the basis of it having particular advantageous properties for the treatment of cancer. The virus of the invention has surprisingly good anti-tumor effects compared to other strains of the same virus isolated from other patients, wherein a patient is an individual harbouring the virus species to be tested. The virus strains used for comparison to identify viruses of the invention may be isolated from a patient or an otherwise healthy (i.e. other than harboring the virus species to be tested) volunteer, preferably an otherwise healthy volunteer. HSV1 strains used to identify a virus of the invention are typically isolated from cold sores of individuals harboring HSV1, typically by taking a swab using e.g. Virocult (Sigma) brand swab/container containing transport media followed by transport to the facility to be used for further testing.

After isolation of viruses to be compared from individuals, stocks of the viruses are typically prepared, for example by growing the isolated viruses on BHK or vero cells. Preferably, this is done following no more than 3 cycles of freeze thaw between taking the sample and it being grown on, for example, BHK or vero cells to prepare the virus stock for further use. More preferably the virus sample has undergone 2 or less than 2 cycles of freeze thaw prior to preparation of the stock for further use, more preferably one cycle of freeze thaw, most preferably no cycles of freeze thaw. Lysates from the cell lines infected with the viruses prepared in this way after isolation are compared, typically by testing for the ability of the virus to kill tumor cell lines in vitro. Alternatively, the viral stocks may be stored under suitable conditions, for example by freezing, prior to testing. Viruses of the invention have surprisingly good anti-tumor effects compared to other strains of the same virus isolated from other individuals, preferably when compared to those isolated from >5 individuals, more preferably >10 other individuals, most preferably >20 other individuals.

The stocks of the clinical isolates identified as viruses of the invention (i.e. having surprisingly good properties for the killing of tumor cells as compared to other viral strains to which they were compared) may be stored under suitable conditions, before or after modification, and used to generate further stocks as appropriate.

A clinical isolate is a strain of a virus species which has been isolated from its natural host. The clinical isolate has preferably been isolated for the purposes of testing and comparing the clinical isolate with other clinical isolates of that virus species for a desired property, in the case of viruses of the invention that being the ability to kill human tumor cells. Clinical isolates which may be used for comparison also include those from clinical samples present in clinical repositories, i,e. previously collected for clinical diagnostic or other purposes. In either case the clinical isolates used for comparison and identification of viruses of the invention will preferably have undergone minimal culture in vitro prior to being tested for the desired property, preferably having only undergone sufficient culture to enable generation of sufficient stocks for comparative testing purposes. As such, the viruses used for comparison to identify viruses of the invention may also include deposited strains, wherein the deposited strain has been isolated from a patient, preferably an HSV1 strain isolated from the cold sore of a patient.

The virus of the invention is an oncolytic virus which is, or is derived from, a clinical isolate which has been selected by comparing the abilities of a panel of three or more clinical isolates of the same viral species to kill tumor cells of two or more tumor cell lines in vitro and selecting a clinical isolate which is capable of killing cells of two or more tumor cell lines more rapidly and/or at a lower dose in vitro than one or more of the other clinical isolates in the panel. Thus, the virus is a clinical isolate that kills two or more tumor cell lines more rapidly and/or at a lower dose in vitro than one or more reference clinical isolates of the same species of virus.

Typically, the clinical isolate of the invention will kill two or more tumor cell lines within 72 hours, preferably within 48 hours, more preferably within 24 hours, of infection at multiplicities of infection. (MOI) of less than or equal to 0.1, preferably less than or equal to an MOI of 0.01 more preferably less than or equal to an MOI of 0.001. Preferably the clinical isolate will kill a broad range of human tumor cell lines, such as 2, 3, 4, 5, 6, 7 or all of the following cell lines: HT29 (colorectal), MDA-MB-231 (breast), SK-MEL-28 (melanoma), Fadu (squamous cell carcinoma), MCF7 (breast), A549 (lung), MIAPACA-2 (pancreas), HT1080 (fibrosarcoma). Thus, the virus of the invention may be capable of killing cells from two or more, such as 3, 4, 5, 6, 7 or more, different types of tumor such as two or more, such as 3, 4, 5, 6, 7 or more, solid tumors, including but not limited to colorectal tumor cells, prostate tumor cells, breast tumor cells, ovarian tumor cells, melanoma cells, squamous cell carcinoma cells, lung tumor cells, pancreatic tumor cells, sarcoma cells and/or fibrosarcoma cells.

Tumor cell line killing can be determined by any suitable method. Typically, a sample is first isolated from a patient, preferably, in the case of HSV1, from a cold sore, is used to infect BHK cells, or another suitable cell line such as vero cells. Positive samples are typically identified by the presence of a cytopathic effect (CPE) 24-72 hours post infection, such as 48 hours post infection, and confirmed to be the target viral species by, for example, immunohistochemistry or PCR. Viral stocks are then generated from the positive samples. A sample from the viral stock is typically tested and compared to other samples generated in the same way using swabs from different patients. Testing may be carried out by determining the level of CPE achieved at a range of multiplicity of infection (MOI) and at various times post infection.

For example, cell lines at 80% confluency may be infected with the viral sample at MOI of 1, 0.1, 0.01 and 0.001 and duplicate plates incubated for 24 and 48 hours at 37° C., 5% $CO_2$ prior to determination of the extent of viral cell killing. This may be determined by, for example, fixing the cells with glutaraldehyde and staining with crystal violet using standard methods. The level of cell lysis may then be assessed by standard methods such as gross observation, microscopy (cell counts) and photography. The method may be repeated with the cells being incubated for shorter time periods, such as 8, 12 or 16 hours, or longer time periods, such as 72 hours, before cell killing is determined, or at additional MOIs such as 0.0001 or less.

Growth curve experiments may also be conducted to assess the abilities of different clinical isolates to replicate in tumor cell lines in vitro. For example, cell lines at 80% confluency may be infected with the viral sample at MOI of 1, 0.1, 0.01 and 0.001 are incubated at 37° C., 5% $CO_2$ and the cells lysed, typically by freeze/thawing, at 0, 8, 16, 24 and 48 hours post infection prior to determination of the extent of viral cell killing. This may be determined by, for example, assessing viral titres by a standard plaque assay.

A clinical isolate of the invention can kill infected tumor cell lines more rapidly and/or at a lower MOI than the other clinical isolates to which it is compared, preferably 2, 3, 4, 5 or 10 or more, other clinical isolates of the same virus species. The clinical isolates of the invention typically kills a 10%, 25% or 50% greater proportion of the tumor cells present at a particular MOI and time point than at least one, preferably 2, 3, 4, 5 or 10 or more, other clinical isolates of the same virus type at the same MOI and time point to which it was compared. The clinical isolate of the invention typically kills the same or a greater proportion of tumor cells at a MOI that is half or less than half that of the MOI at which one or more, preferably 2, 3, 4, 5,10 or 15 or more, other clinical isolates of the same virus species used for the comparison at the same time point, typically at 12, 24 and/or 48 hours, kills the same proportion of tumor cells. Preferably, a clinical isolate of the invention typically kills the same or a greater proportion of tumor cells at a MOI that is 5 or 10 times lower than the MOI at which one or more, preferably 2, 3, 4, 5, 10 or 15 or more, other clinical isolates of the same virus used for the comparison at the same time point, typically at 12, 24 and/or 48 hours kills the same proportion of tumor cells. The improved tumor cell killing abilities of a virus of the invention are typically achieved compared to at least 50%, 75% or 90% of the other clinical isolates of the same viral species used for the comparison. The virus is preferably compared to at least 4 other virus strains, such as, for example, 7, 9, 19, 39 or 49 other virus strains of the same species.

The isolated strains may be tested in batches, for example of 4-8 viral strains at a time, on, for example, 4-8 of the tumor cell lines at a time. For each batch of experiments, the degree of killing achieved is ranked on each cell line for the best (i.e. least surviving cells at each time point/MOI) to the worst (i.e. most surviving cells for each time point/MOI) for the viruses being compared in that experiment. The virus strains from each experiment which perform the best across the range of tumor cell line tested (i.e. that consistently ranked as one of the best at killing the cell lines) may then be compared head to head in further experiments using other clinical isolates and/ore other tumor cell lines to identify the best virus strains in the total of, for example, >20 virus strains sampled. Those ranked as the best overall are the viruses of the invention.

In a preferred embodiment, the virus of the invention is a strain selected from:
  strain RH018A having the provisional accession number ECCAC 16121904;
  strain RH004A having the provisional accession number ECCAC 16121902;
  strain RH031A having the provisional accession number ECCAC 16121907;
  strain RH040A having the provisional accession number ECCAC 16121908;
  strain RH015A having the provisional accession number ECCAC 16121903;
  strain RH021A having the provisional accession number ECCAC 16121905;
  strain RH023A having the provisional accession number ECCAC 16121906; and
  strain RH047A having the provisional accession number ECCAC 16121909.

More preferably, the virus of the invention is a strain selected from:
  strain RH018A having the provisional accession number ECCAC 16121904;
  strain RH004A having the provisional accession number ECCAC 16121902;
  strain RH031A having the provisional accession number ECCAC 16121907;
  strain RH040A having the provisional accession number ECCAC 16121908; and
  strain RH015A having the provisional accession number ECCAC 16121903;

Most preferably, the virus of the invention is strain RH018A having the accession number EACC 16121904.

An HSV of the invention is capable of replicating selectively in tumors, such as human tumors. Typically, the HSV replicates efficiently in target tumors but does not replicate efficiently in non-tumor tissue. This HSV comprises one or more mutations in one or more viral genes that inhibit replication in normal tissue but still allow replication in tumors. The mutation may, for example, be a mutation that prevents the expression of functional ICP34.5, ICP6 and/or thymidine kinase by the HSV.

In one preferred embodiment, the ICP34.5-encoding genes are mutated to confer selective oncolytic activity on the HSV. Mutations of the ICP34.5-encoding genes that prevent the expression of functional ICP34.5 are described in Chou et al. (1990) Science 250:1262-1266, Maclean et al. (1991) J. Gen. Virol. 72:631-639 and Liu et al. (2003) Gene Therapy 10:292-303, which are incorporated herein by reference. The ICP6-encoding gene and/or thymidine kinase-encoding gene may also be inactivated, as may other genes provided that such inactivation does not prevent the virus infecting or replicating in tumors.

The HSV may contain a further mutation or mutations which enhance replication of the HSV in tumors. The resulting enhancement of viral replication in tumors not only results in improved direct 'oncolytic' tumor cell killing by the virus, but also enhances the level of heterologous (i.e. a gene inserted into the virus, in the case of viruses of the invention genes encoding fusogenic protein(s) and an immune modulatory molecule(s)) gene expression and increases the amount of tumor antigen released as tumor cells die, both of which may also improve the immunogenic properties of the therapy for the treatment of cancer. For example, in a preferred embodiment of the invention, deletion of the ICP47-encoding gene in a manner that places the US11 gene under the control of the immediate early promoter that normally controls expression of the ICP47 encoding gene leads to enhanced replication in tumors (see Liu et al., 2003, which is incorporated herein by reference).

Other mutations that place the US11 coding sequence, which is an HSV late gene, under the control of a promoter that is not dependent on viral replication may also be introduced into a virus of the invention. Such mutations allow expression of US11 before HSV replication occurs and enhance viral replication in tumors. In particular, such mutations enhance replication of an HSV lacking functional ICP34.5-encoding genes.

Accordingly, in one embodiment the HSV of the invention comprises a US11 gene operably linked to a promoter, wherein the activity of the promoter is not dependent on viral replication. The promoter may be an immediate early (IE) promoter or a non-HSV promoter which is active in mammalian, preferably human, tumor cells. The promoter may, for example, be a eukaryotic promoter, such as a promoter derived from the genome of a mammal, preferably a human. The promoter may be a ubiquitous promoter (such as a promoter of (β-actin or tubulin) or a cell-specific promoter, such as tumor-specific promoter. The promoter may be a viral promoter, such as the Moloney murine leukaemia virus long terminal repeat (MMLV LTR) promoter or the human or mouse cytomegalovirus (CMV) IE promoter. HSV immediate early (IE) promoters are well known in the art. The HSV IE promoter may be the promoter driving expression of ICP0, ICP4, ICP22, ICP27 or ICP47.

The genes referred to above may be rendered functionally inactive by any suitable method, for example by deletion or substitution of all or part of the gene and/or control sequence of the gene or by insertion of one or more nucleic acids into or in place of the gene and/or the control sequence of the gene. For example, homologous recombination methods, which are standard in the art, may be used to generate the virus of the invention.

As used herein, the term "gene" is intended to mean the nucleotide sequence encoding a protein, i.e. the coding sequence of the gene. The various genes referred to above may be rendered non-functional by mutating the gene itself or the control sequences flanking the gene, for example the promoter sequence. Deletions may remove one or more portions of the gene, the entire gene or the entire gene and all or some of the control sequences. For example, deletion of only one nucleotide within the gene may be made, resulting in a frame shift. However, a larger deletion may be made, for example at least about 25%, more preferably at least about 50% of the total coding and/or non-coding sequence. In one preferred embodiment, the gene being rendered functionally inactive is deleted. For example, the entire gene and optionally some of the flanking sequences may be removed from the virus. Where two or more copies of the gene are present in the viral genome both copies of the gene are rendered functionally inactive.

A gene may be inactivated by substituting other sequences, for example by substituting all or part of the endogenous gene with a heterologous gene and optionally a promoter sequence. Where no promoter sequence is substituted, the heterologous gene may be inserted such that it is controlled by the promoter of the gene being rendered non-functional. In an HSV of the invention it is preferred that the ICP34.5 encoding-genes are rendered non-functional by the insertion of a heterologous gene or genes and a promoter sequence or sequences operably linked thereto, and optionally other regulatory elements such as polyadenylation sequences, into each the ICP34.5-encoding gene loci.

A virus of the invention may be used to express a fusogenic protein and/or an immune stimulatory protein in tumors. This is typically achieved by inserting a heterologous gene encoding the fusogenic protein and/or a heterologous gene encoding the immune stimulatory protein in the genome of a selectively replication competent virus wherein each gene is under the control of a promoter sequence. As replication of such a virus will occur selectively in tumor tissue, expression of the fusogenic protein and/or immune stimulatory protein by the virus is also enhanced in tumor tissue as compared to non-tumor tissue in the body. Enhanced expression occurs where expression is greater in tumors as compared to other tissues of the body. Accordingly, the invention provides benefits of expression of both a fusogenic protein and/or an immune stimulatory protein selectively in tumors combined with the anti-tumor effect provided by oncolytic virus replication.

Fusogenic Protein

The virus of the invention may comprise a gene encoding a fusogenic protein. The fusogenic protein may be any heterologous protein capable of promoting fusion of a cell infected with the virus of the invention to another cell. A fusogenic protein, preferably a wild type or modified viral glycoprotein (i.e. modified to increase its fusogenic properties), is a protein which is capable in inducing the cell to cell fusion (syncitia formation) of cells in which it is expressed. Examples of fusogenic glycoprotiens include VSV-G, syncitin-1 (from human endogenous retrovirus-W (HERV-W)) or syncitin-2 (from HERVFRDE1), paramyxovirus SV5-F, measles virus-H, measles virus-F, RSV-F, the glycoprotein from a retrovirus or lentivirus, such as gibbon ape leukemia virus (GALV), murine leukemia virus (MLV), Mason-Pfizer monkey virus (MPMV) and equine infectious anemia virus (EIAV) with the R transmembrane peptide removed (R-versions). In a preferred embodiment the fusogenic protein is from GALV and has the R-peptide removed (GALV-R−).

The virus of the invention may comprise multiple copies of the fusogenic protein-encoding gene, preferably 1 or 2 copies. The virus may comprise two or more different fusogenic proteins, including any of the fusogenic proteins listed above.

The fusogenic protein or proteins expressed by a virus of the invention may be identical to a naturally occurring protein, or may be a modified protein.

The fusogenic protein-encoding gene (fusogenic gene) may have a naturally occurring nucleic acid sequence or a modified sequence. The sequence of the fusogenic gene may, for example, be modified to increase the fusogenic properties of the encoded protein, or to provide codon optimisation and therefore increase the efficiency of expression of the encoded protein.

Immune Stimulatory Molecule

The virus of the invention may comprise one or more immune stimulatory molecules and/or one or more genes encoding an immune stimulatory molecule Immune stimulatory molecules include proteins which may aid in the induction of an immune response, proteins which may relieve inhibitory signals to the induction or effectiveness of an immune response and RNA molecules (e.g. shRNA, antisense RNA, RNAi or micro RNA) which inhibit the expression of immune inhibitory molecules.

Examples of immune stimulatory molecules include IL-2, IL12, IL-15, IL-18, IL-21, IL-24, CD40 ligand, GITR ligand, 4-1-BB ligand, OX40 ligand, ICOS ligand, flt3 ligand, type I interferons, including interferon alpha and interferon beta, interferon gamma, type III interferon (IL-28, IL-29), other cytokines such as TNF alpha or GM-CSF, TGF beta or immune checkpoint antagonists Immune checkpoint antagonists include antibodies, single chain antibodies and RNA1/siRNA/microRNA/antisense RNA knockdown approaches. Agonists of immune potentiating/co-stimulatory pathways include mutant or wild type, soluble, secreted and/or membrane bound ligands, and agonistic antibodies including single chain antibodies. With regard to the targeting of immune co-inhibitory or immune co-stimulatory pathways, proteins or other molecules (agonistic or antagonistic depending on the case) targeting CTLA-4 (antagonist), PD-1 (antagonist), PD-L1 (antagonist), LAG-3 (antagonist), TIM-3 (antagonist), VISTA (antagonist), CSF1R (antagonist), IDO (antagonist), CEACAM1 (antagonist), GITR (agonist), 4-1-BB (agonist), KIR (antagonist), SLAMF7 (antagonist), OX40 (agonist), CD40 (agonist), ICOS (agonist) or CD47 (antagonist) are particularly preferred. Viruses of the invention therefore preferably encode one or more of these molecules. More preferably viruses of the invention encode GM-CSF and/or a wild type or modified version of CD40L, ICOSL, 4-1-BBL, GITRL or OX40L, most preferably GM-CSF.

The inhibitor of a co-inhibitory pathway may be a CTLA-4 inhibitor. The CTLA-4 inhibitor is typically a molecule such as a peptide or protein that binds to CTLA-4 and reduces or blocks signaling through CTLA-4, such as by reducing activation by B7. By reducing CTLA-4 signalling, the inhibitor reduces or removes the block of immune stimulatory pathways by CTLA-4.

The CTLA-4 inhibitor is preferably an antibody or an antigen binding fragment thereof. The term "antibody" as referred to herein includes whole antibodies and any antigen binding fragment (i.e., "antigen-binding portion") or single chains thereof. An antibody refers to a glycoprotein comprising at least two heavy (H) chains and two light (kappa) (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region (abbreviated herein as VL) and a light chain constant region. The variable regions of the heavy and light chains contain a binding domain that interacts with an antigen. The VH and VL regions can be further subdivided into regions of hypervariability, termed complementarity determining regions (CDR), interspersed with regions that are more conserved, termed framework regions (FR). The constant regions of the antibodies may mediate the binding of the immunoglobulin to host tissues or factors, including various cells of the immune system (e.g., effector cells) and the first component (Clq) of the classical complement system.

The antibody is typically a monoclonal antibody. The antibody may be a chimeric antibody. The antibody is preferably a humanised antibody and is more preferably a human antibody.

The term "antigen-binding fragment" of an antibody refers to one or more fragments of an antibody that retain the ability to specifically bind to CTLA-4. The antigen-binding fragment also retains the ability to inhibit CTLA-4 and hence to reduce or remove the CTLA-4 blockade of a stimulatory immune response. Examples of suitable fragments include a Fab fragment, a F(ab')₂ fragment, a Fab' fragment, a Fd fragment, a Fv fragment, a dAb fragment and an isolated complementarity determining region (CDR). Single chain antibodies such as scFv and heavy chain antibodies such as VHH and camel antibodies are also intended to be encompassed within the term "antigen-binding portion" of an antibody. In a preferred embodiment, the antibody is an scFv. Examples of suitable scFv molecules are disclosed in, for example, WO2007/123737 and WO2014/066532, which are incorporated herein by reference. The scFv may be encoded by the nucleotide sequence shown in SEQ ID NO: 34 the nucleotide sequence shown in SEQ ID NO: 35.

Viruses of the invention may encode one or more immune stimulatory molecules, preferably 1, 2, 3 or 4 immune stimulatory molecules, more preferably 1 or 2 immune stimulatory molecules.

The sequence of the gene encoding the immune stimulatory molecule may be codon optimized so as to increase expression levels of the respective proteins in target cells as compared to if the unaltered sequence is used.

Modification of Virus Strains

Modified viruses of the invention are modified versions of such clinical isolates identified as having advantageous properties for killing tumor cells as compared to other virus strains used for the comparison. Modified viruses of the invention are constructed using methods well known in the art. For example plasmids (for smaller viruses and single and multiple genome component RNA viruses) or BACS (for larger DNA viruses including herpes viruses) encoding the viral genome to be packaged, including any genes encoding fusogenic and/or immune stimulating molecules under appropriate regulatory control, can be constructed by standard molecular biology techniques and transfected into permissive cells from which recombinant viruses can be recovered.

Alternatively, in a preferred embodiment plasmids containing DNA regions flanking the intended site of insertion can be constructed, and then co-transfected into permissive cells with viral genomic DNA such that homologous recombination between the target insertion site flanking regions in the plasmid and the same regions in the parental clinical isolate occur. Recombinant viruses can then be selected and purified through the loss or addition of a function inserted or deleted by the plasmid used for modification, e.g. insertion or deletion of a marker gene such as GFP or lacZ from the parental virus at the intended insertion site. In a most preferred embodiment the insertion site is the ICP34.5 locus of HSV, and therefore the plasmid used for manipulation contains HSV sequences flanking this insertion site, between which are an expression cassette encoding a fusogenic protein and an immune stimulatory molecule. In this case, the parental clinical isolate may contain a cassette encoding GFP in place of ICP34.5 and recombinant virus plaques are selected through the loss of expression of GFP. In a most preferred embodiment the US11 gene of HSV is also expressed as an IE gene. This may be accomplished through deletion of the ICP47-encoding region, or by other means.

Fusogenic protein encoding sequences and immune stimulatory molecule encoding sequences may be inserted into the viral genome under appropriate regulatory control. This may be under the regulatory control of natural promoters of the virus species of the invention used, depending on the species and insertion site, or preferably under the control of heterologous promoters. Suitable heterologous promoters include mammalian promoters, such as the IEF2a promoter or the actin promoter. More preferred are strong viral promoters such as the CMV IE promoter, the RSV LTR, the MMLV LTR or promoters derived from SV40. Preferably each exogenous gene (i.e. encoding the fusogenic protein and immune modulatory molecule) will be under separate promoter control, but may also be expressed from a single RNA transcript, for example through insertion of an internal ribosome entry sites (IRES) between protein coding sequences. RNA derived from each promoter is typically terminated using a polyadenylation sequence (e.g. mammalian sequences such as the bovine growth hormone (BGH) poly A sequence, synthetic polyadenylation sequences, or viral sequences such as the SV40 early or late polyadenylation sequence).

The invention also provides a virus, such as a pox virus or a HSV, preferably HSV1, which expresses at least three heterologous genes, wherein each of the three heterologous genes is driven by a different promoter selected from the CMV promoter, the RSV promoter, the EF1a promoter, the SV40 promoter and a retroviral LTR promoter. The virus may, for example, express four heterologous genes, wherein each of the four heterologous genes is driven by a different promoter selected from the CMV promoter, the RSV promoter, the EF1a promoter, the SV40 promoter and a retroviral LTR promoter. The retroviral LTR is preferably from MMLV (SEQ ID NO:43), also knowm as MoMuLV. The heterologous genes may be terminated by poly adenylation sequences. The poly adenylation sequences may be the same or different. Preferably each heterologous gene is terminated by a different poly adenylation sequence, which is preferably selected from the BGH, SV40, HGH and RBG poly adenylation sequences.

The invention also provides a virus, such as a pox virus or a HSV, preferably HSV1, which expresses at least three heterologous genes, wherein each of the three heterologous genes is terminated by a different poly adenylation sequence selected from the BGH, SV40, HGH and RBG poly adenylation sequences. The virus may, for example, express four heterologous genes terminated by each of the BGH, SV40, HGH and RBG poly adenylation sequences, respectively.

Pharmaceutical Compositions

The invention provides a pharmaceutical composition comprising a virus of the invention and a pharmaceutically acceptable carrier or diluent. Suitable carriers and diluents include isotonic saline solutions, for example phosphate-buffered saline. The composition may further comprise other constituents such as sugars or proteins to improve properties such as stability of the product. Alternatively a lyophilized formulation may be used, which is reconstituted in a pharmaceutically acceptable carrier or diluent before use.

The choice of carrier, if required, is frequently a function of the route of delivery of the composition. Within this invention, compositions may be formulated for any suitable route and means of administration. Pharmaceutically acceptable carriers or diluents are those used in compositions suitable for intra-tumoral administration, intravenous/intraarterial administration, administration into the brain or administration into a body cavity (e.g. bladder, pleural cavity or by intraperitoneal administration). The composition may be administered in any suitable form, preferably as a liquid.

The present invention also provides a product of manufacture comprising a virus of the invention in a sterile vial, ampoule or syringe.

Medical Uses/Methods of Treatment

The invention provides the virus of the invention for use in the treatment of the human or animal body by therapy, particularly for use in a method of treating cancer. The cancer is typically in a mammal, preferably in a human. The virus kills infected tumour cells by virus mediated toxicity, including by lysis, necrosis or apoptosis, preferably by lysis or necrosis. The virus of the invention also elicits a systemic anti-tumor immune response, augmented through the expression of the immune stimulatory molecule, which also kills cancer cells.

The invention also provides a method of treating cancer, the method comprising administering a therapeutically effective amount of the virus of the invention to an individual in need thereof.

The invention additionally provides the use of the virus of the invention in the manufacture of a medicament for treating cancer.

The virus of the invention is particularly useful in treating any solid tumor including any adenocarcinoma, carcinoma or sarcoma. For example, the virus of the invention is useful in treating head and neck, prostate, breast, ovarian, lung, liver, endometrial, bladder, gall bladder, pancreas, colon, kidney, stomach/gastric, esophageal, or cervical cancers, mesothelioma, melanoma or other skin cancer, lymphoma, glioma or other cancer of the nervous system, or sarcomas such as soft tissue sarcoma.

The virus of the invention may be used to treat malignant tumors, including tumors that have metastasised from the site of the original tumor. In this embodiment, the virus may be administered to the primary tumor or to one or more secondary tumors.

The virus of the invention may be administered in combination with other therapeutic agents, including chemotherapy, targeted therapy, immunotherapy (including immune co-inhibitory pathway blockade or immune co-stimulatory pathway activation) and/or in combination with radiotherapy and/or in combination with any combination of these. The therapeutic agent is preferably an anti-cancer agent.

The virus of the invention may be administered in combination with a second virus, such as a second oncolytic virus.

For example, the therapeutic agent may comprise an immunogen (including a recombinant or naturally occurring antigen, including such an antigen or combination of antigens delivered as DNA or RNA in which it/they are encoded), to further stimulate an immune response, such as a cellular or humoral immune response, to tumor cells, particularly tumor neoantigens. The therapeutic agent may be an agent intended to increase or potentiate an immune response, such as a cytokine, an agent intended to inhibit an immune checkpoint pathway or stimulate an immune potentiating pathway or an agent which inhibits the activity of regulatory T cells (Tregs).

The therapeutic agent may be an agent known for use in an existing cancer therapeutic treatment. The therapeutic agent may be radiotherapy or a chemotherapeutic agent. The therapeutic agent may be selected from cyclophosmamide, alkylating-like agents such as cisplatin or melphalan, plant alkaloids and terpenoids such as vincristine or paclitaxel (Taxol), antimetabolites such as 5-fluorouracil, topoisomerase inhibitors type I or II such as camptothecin or doxorubicin, cytotoxic antibiotics such as actinomycin, anthracyclines such as epirubicin, glucocorticoids such as triamcinolone, inhibitors of protein, DNA and/or RNA synthesis such as methotrexate and dacarbazine, histone deacetylase (HDAC) inhibitors, or any other chemotherapy agent.

The therapeutic agent may be one, or a combination of: immunotherapeutics or immunomodulators, such as TLR agonists; agents that down-regulate T-regulatory cells such as cyclophosphamide; or agents designed to block immune checkpoints or stimulate immune potentiating pathways, including but not limited to monoclonal antibodies, such as a CTLA-4 inhibitor, a PD-1 inhibitor, a PD-L1 inhibitor, a LAG-3 inhibitor, a TIM-3 inhibitor, a VISTA inhibitor, a CSF1R inhibitor, an IDO inhibitor, a CEACAM1 inhibitor, a GITR agonist, a 4-1-BB agonist, a KIR inhibitor, a SLAMF7 inhibitor, an OX40 agonist, a CD40 agonist, an ICOS agonist or a CD47 inhibitor. In a preferred embodiment, the therapeutic agent is a CTLA-4 inhibitor such as an anti-CTLA-4 antibody, a PD1 inhibitor, such as an anti-PD-1 antibody or a PD-L1 inhibitor such as an anti-PD-L1 antibody. Such inhibitors, agonists and antibodies can be generated and tested by standard methods known in the art.

Immunotherapeutic agents may also include bi-specific antibodies, cell based-therapies based on dendritic cells, NK cells or engineered T cells such CAR-T cells or T cells expressing engineered T cell receptors Immunotherapeutic agents also include agents that target a specific genetic mutation which occurs in tumors, agents intended to induce immune responses to specific tumor antigens or combinations of tumor antigens, including neoantigens and/or agents intended to activate the STING/cGAS pathway, TLR or other innate immune response and/or inflammatory pathway, including intra-tumoral agents.

For example, a virus of the invention may be used: in combination with dacarbazine, a BRAF inhibitor and or CTLA-4, PD1 or PD-L1 blockade to treat melanoma; in combination with taxol, doxorubicin, vinorelbine, cyclophosphamide and/or gemcitabine to treat breast cancer; in combination with 5-fluorouracil and optionally leucovorin, irinoteacan and/or oxaliplatin to treat colorectal cancer; in combination with taxol, carboplatin, vinorelbine and/or gemcitabine, PD-1 or PD-L1 blockade to treat lung cancer; in combination with cisplatin and/or radiotherapy to treat head and neck cancer.

The therapeutic agent may be an inhibitor of the idoleamine 2,3-dioxygenase (IDO) pathway. Examples of IDO inhibitors include epacadostat (INCB024360), 1-methyl-tryptophan, indoximod (1-methyl-D-tryptophan), GDC-0919 or F001287.

The mechanism of action of IDO in suppressing anti-tumor immune responses may also suppress immune responses generated following oncolytic virus therapy. IDO expression is induced by toll like receptor (TLR) activation and interferon-γ both of which may result from oncolytic virus infection. One embodiment of the use of oncolytic virus therapy for cancer treatment includes combination of an oncolytic virus, including a virus expressing an immune stimulating protein or proteins and/or a fusogenic protein, with an inhibitor of the IDO pathway and optionally one or more further antagonist of an immune co-inhibitory pathway and/or one or more agonist of an immune co-stimulatory pathway, including those targeting CTLA-4, PD-1 and/or PD-L1.

The invention also provides a method of treating cancer, which comprises administering a therapeutically effective amount of an oncolytic virus, an inhibitor of the indoleamine 2,3-dioxygenase (IDO) pathway and a further antagonist of an immune co-inhibitory pathway, and/or an agonist of an immune co-stimulatory pathway to a patient in need thereof. The oncolytic virus is preferably a modified clinical isolate. The oncolytic virus is preferably a pox virus, more preferably a HSV, such as a HSV1 and/or a HSV rendered functionally inactive for ICP34.5 and/or ICP47. The oncolytic virus may express an immune stimulating molecule, such as GM-CSF, and/or a fusogenic protein, such as the GALV fusogenic glycoprotein with the R sequence mutated or deleted. The further antagonist of an immune co-inhibitory pathway is preferably an antagonist of CTLA-4, an antagonist of PD1 or an antagonist of PD-L1. For example, the further antagonist of an immune co-inhibitory pathway may be an inhibitor of the interaction between PD1 and PD-L1.

Where a therapeutic agent and/or radiotherapy is used in conjunction with a virus of the invention, administration of the virus and the therapeutic agent and/or radiotherapy may be contemporaneous or separated by time. The composition of the invention may be administered before, together with or after the therapeutic agent or radiotherapy. The method of treating cancer may comprise multiple administrations of the virus of the invention and/or of the therapeutic agent and/or radiotherapy. A skilled practitioner will readily be able to determine suitable courses of administration of the virus and the therapeutic agent.

In preferred embodiments, in the case of combination with one or more antagonist of an immune co-inhibitory pathway, one or more agonist of an immune co-stimulatory pathway and/or other immune potentiating agents, the virus of the invention is administered once or multiple times prior to the concurrent administration of the antagonist of an immune co-inhibitory pathway, agonist of an immune co-stimulatory pathway and/or other immune potentiating agent or agents thereafter, or concurrent with the administration of the antagonist of an immune co-inhibitory pathway, agonist of an immune co-stimulatory pathway and/or other immune potentiating agent or agents without prior administration of the virus of the invention.

The virus of the invention may be administered to a subject by any suitable route. Typically, a virus of the invention is administered by direct intra-tumoral injection, including through the use of imaging guidance to target the tumor or tumors. The virus may be administered into a body cavity, for example into the pleural cavity, bladder or by intra-peritoneal administration. The virus may be injected into a blood vessel, preferably a blood vessel supplying a tumor.

Therapeutic agents which may be combined with a virus of the invention can be administered to a human or animal subject in vivo using a variety of known routes and techniques. For example, the composition may be provided as an injectable solution, suspension or emulsion and administered via parenteral, subcutaneous, oral, epidermal, intradermal, intramuscular, interarterial, intraperitoneal, intravenous injection using a conventional needle and syringe, or using a liquid jet injection system. The composition may be administered topically to skin or mucosal tissue, such as nasally, intratrachealy, intestinally, sublingually, rectally or vaginally, or provided as a finely divided spray suitable for respiratory or pulmonary administration. In preferred embodiments, the compositions are administered by intravenous infusion, orally, or directly into a tumor.

The virus and/or therapeutic agent may be administered to a subject in an amount that is compatible with the dosage composition that will be therapeutically effective. The administration of the virus of the invention is for a "therapeutic" purpose. As used herein, the term "therapeutic" or "treatment" includes any one or more of the following as its objective: the prevention of any metastasis or further metastasis occurring; the reduction or elimination of symptoms; the reduction or complete elimination of a tumor or cancer, an increase in the time to progression of the patient's cancer; an increase in time to relapse following treatment; or an increase in survival time.

Therapeutic treatment may be given to Stage I, II, III, or IV cancers, preferably Stage II, III or IV, more preferably Stage III or IV, pre- or post-surgical intervention, preferably before surgical intervention (either for resection of primary or recurrent/metastatic disease), i.e. while residual tumor remains.

Therapeutic treatment may be carried out following direct injection of the virus composition into target tissue which may be the tumor, into a body cavity, or a blood vessel. As a guide, the amount of virus administered is in the case of HSV in the range of from $10^4$ to $10^{10}$ pfu, preferably from $10^5$ to $10^9$ pfu. In the case of HSV, an initial lower dose (e.g. $10^4$ to $10^7$ pfu) may be given to patients to seroconvert patients who are seronegative for HSV and boost immunity in those who are seropositive, followed by a higher dose then being given thereafter (e.g. $10^6$ to $10^9$ pfu). Typically up to 20 ml of a pharmaceutical composition consisting essentially of the virus and a pharmaceutically acceptable suitable carrier or diluent may be used for direct injection into tumors, or up to 50 ml for administration into a body cavity (which may be subject to further dilution into an appropriate diluent before administration) or into the bloodstream. However for some oncolytic therapy applications larger or smaller volumes may also be used, depending on the tumor and the administration route and site.

The routes of administration and dosages described are intended only as a guide since a skilled practitioner will be able to determine readily the optimum route of administration and dosage. The dosage may be determined according to various parameters, especially according to the location of the tumor, the size of the tumor, the age, weight and condition of the patient to be treated and the route of administration. Preferably the virus is administered by direct injection into the tumor. The virus may also be administered by injection into a blood vessel or into a body cavity. The optimum route of administration will depend on the location and size of the tumor. Multiple doses may be required to achieve an immunological or clinical effect, which, if required, will be typically administered between 2 days to 12 weeks apart, preferably 3-days to 3 weeks apart. Repeat doses up to 5 years or more may be given, preferably for up to one month to two years dependent on the speed of response of the tumor type being treated and the response of a particular patient, and any combination therapy which may also be being given.

The following Examples illustrate the invention.

EXAMPLE 1

Clinical Isolates with Improved Anti-tumor Effects

The virus species used to exemplify the invention is HSV, specifically HSV1. Cold sore swabs were taken from more than 20 otherwise healthy volunteers. A sample of each swab was used to infect BHK cells. Samples containing HSV1 were identified by the presence of a cytopathic effect (CPE) 24-72 hours post infection and by immunohistochemistry and viral stocks of the primary clinical isolates were generated from the positive samples.

The abilities of the primary clinical isolates of HSV1 to kill a panel of human tumor-derived cell lines is tested and the virus strain with the greatest ability to kill a broad range of these rapidly, and at low dose is chosen. Tumor cell lines used for this comparison are HT29 (colorectal), MDA-MB-231 (breast), SK-MEL-28 (melanoma), Fadu (squamous cell carcinoma), MCF7 (breast), A549 (lung), MIAPACA-2 (pancreas), CAPAN-1(pancreas), HT1080 (fibrosarcoma).

The cell lines are used to test for the level of CPE achieved at a range of MOI and times post infection for each of the primary clinical isolates.

More specifically, the tumor cell lines are used to seed multi-well tissue culture plates so that they are about 80% confluent on the day of infection. Representative wells from each tumor cell line are trypsinised and the number of cells in the well determined. These cell counts are used to determine the volume of each clinical isolate required to give an MOI of 1, 0.1, 0.01 and 0.001. Separate wells of a tumor cell line are infected with the clinical isolate at these MOI and overlaid with growth media and carboxymethyl-cellulose. All infections are carried out in quadruplicate. Duplicate wells are incubated for 24 hours and duplicate wells are incubated for 48 hours, both at 37° C., 5% $CO_2$, prior to fixation of the cells with glutaraldehyde and staining with crystal violet. The level of cell lysis is then assessed by gross observation, microscopy (cell counts) and photography or using a metabolic assay such as an MTT assay.

Growth curve experiments are also conducted to assess the abilities of different clinical isolates to replicate in tumor cell lines in vitro. The tumor cell lines are used to seed multi-well tissue culture plates so that they are about 80% confluent on the day of infection. Cell counts are determined as above and used to determine the volume of virus to give MOIs of 1, 0.1, 0.01 and 0.001. The tumor cells are infected in duplicate for MOI and time point. The infected cells are incubated at 37° C., 5% $CO_2$ and the cells lysed by freeze/thawing at 0, 8, 16, 24 and 48 hours post infection. Viral titres are assessed by a standard plaque assay.

EXAMPLE 2

Modification of Clinical Isolates

In this example the clinical isolate selected in Example 1 (i.e. a virus if the invention) is modified by deletion of ICP47 from the viral genome using homologous recombination with a plasmid containing regions flanking DISV1 nucleotides 145300 to 145582 (HSV1 nucleotides 145300 to 145582 being the sequences to be deleted; HSV1 strain 17 sequence Genbank file NC_001806.2) between which are encoded GFP. GFP expressing virus plaques are selected, and GFP then removed by homologous recombination with the empty flanking regions and plaques which do not express GEP are selected. This results in an ICP47 deleted virus in which US11 is expressed as an IE protein as it is now under the control of the ICP47 promoter. ICP34.5 is then deleted using homologous recombination with a plasmid containing regions flanking HSV1 nucleotides 124953 to 125727 (HSV1 nucleotides 124953 to 125727 being the sequences to be deleted; HSV1 strain 17 sequence Genbank file NC_001806.2) between which GFP is encoded. GFP expressing virus plaques are again selected, and GFP then removed by homologous recombination with the same flanking regions but between which are now an expression cassette comprising a codon optimized version of the mouse GM-CSF sequence and a codon optimized version of the GALV R- sequence driven by the CMV IE promoter and RSV promoter respectively, in a back to back orientation and again selecting virus plaques which do not express GFP. This virus construction is performed using methods which are standard in the art.

The structure of the resulting virus is shown in FIG. 1 (top panel). The mGM-CSF and GALV-R- sequences are shown in SEQ ID NOs 2 and 8 respectively. The structure of the resulting virus is confirmed by restriction digestion and Southern blot, GM-CSF expression is confirmed by ELISA, and GALV-R- expression is confirmed by infection of human HT1080 tumor cells and the observation of syncitial plaques.

Viruses are also constructed using similar procedures which have no insertion into ICP34.5, or which only have inserted the gene for mouse GM-CSF or GALV-R-. The structures of these viruses are also shown in FIG. 1.

For human use, hGM-CSF is used, the sequence for a codon optimised version of which is shown in SEQ ID NO 4.

EXAMPLE 3

Expression of Two Immune Stimulatory Molecule from a Virus Expressing a Fusogenic Protein A virus similar to the GALV-R- and mCGM-CSF expressing virus described above is constructed, but additionally expressing versions of CD40L. Here, instead of using a plasmid containing ICP34.5 flanking regions and an expression cassette comprising GM-CSF and GALV-R- driven by a CMV and an RSV promoter, a plasmid containing ICP34.5 flanking regions and an expression cassette comprising GM-CSF, GALV and CD40L driven by a CMV, an RSV and an SV40 promoter is used for recombination with the virus containing GFP inserted into ICP34.5 and non-GFP expressing plaques again selected.

EXAMPLE 4

The Effect of the Combined Expression of a Fusogenic Protein and an Immune Stimulatory Molecule from an Oncolytic Virus in Mouse Tumor Models The GALV R- protein causes cell to cell fusion in human cells but not in mouse cells because the PiT-1 receptor required for cell fusion to occur has a sequence in mice which does not allow cell fusion to occur. As a result mouse tumor cells expressing human PiT-1 are first prepared using methods standard in the art. Human PiT-1 is cloned into a lentiviral vector also comprising a selectable marker gene. The vector is transfected into target CT26 mouse colorectal cancer tumor cells and clones resistant to the selectable marker are selected to generate CT26/PiT-1 cells, PiT-1 expression is confirmed by western blotting in untransfected cells and in cells transfected with the PiT-1 expressing lentivirus and by transfection of a plasmid expressing GALV-R- and confirmation that cell fusion occurs.

The utility of the invention is demonstrated by administering CT26/PiT-1 cells into both flanks of Balb/c mice and allowing the CT26/PiT-1 tumors to grow to approximately 0.5 cm in diameter.

The following treatments are then administered to groups of mice (five per group), into one flank of each mouse only 3 times per week for two weeks:
  50 µl of saline (1 group);
  50 µl of $10^5$ pfu/ml, $10^6$ pfu, or $10^7$ pfu/ml of the HSV with no inserted gene (3 groups);
  50 µl of $10^5$ pfu/ml, $10^6$ pfu/ml, or $10^7$ pfu/ml of the HSV with only mouse GM-CSF inserted (3 groups);
  50 µl of $10^5$ pfu/ml, $10^6$ pfu/ml, or $10^7$ pfu/ml of the virus with only GALV-R- inserted (3 groups); or
  50 µl of $10^5$ pfu/ml, $10^6$ pfu/ml, or $10^7$ pfu/ml of the virus with both mouse GM-CSF and GALV-R- inserted (3 groups).

Effects on tumor growth are then observed for up to one month. Superior tumor control and shrinkage in both injected and uninjected tumors with the virus expressing GM-CSF and GALV-R- as compared to the other groups is observed, including through an improved dose response curve.

EXAMPLE 5

The Effect of Combined Expression of a Fusogenic Protein and an Immune Stimulatory Molecule from an Oncolytic Virus on the Therapeutic Effect of Immune Checkpoint Blockade in Mouse Tumor Models The experiment in Example 3 above is repeated but mice are additionally dosed bi-weekly by the intra-peritoneal route with an antibody targeting mouse PD-1 (10 mg/kg; Bioxcell RMP-1-14 on the same days as virus dosing) or an antibody targeting mouse CTLA-4 (10 mg/kg; Bioxcell 9H10 on the same days as virus dosing). An additional group of mice is added which receive no antibody treatment. More specifically, groups of mice receive (1) saline, (2) HSV with no inserted gene, (3) HSV with both GM-CSF and GALV-R-inserted as in Example 3, (4) PD-1 antibody, (5) CTLA-4 antibody, (6) HSV with no inserted gene plus PD-1 antibody, (7) HSV with no inserted gene plus CTLA-4 antibody, (8) HSV with GM-CST and GALV-R- and PD-1 antibody or (9) HSV with GM-CSF and GALV-R- and CTLA-4 antibody. Superior tumor control and shrinkage in both injected and uninjected tumors with the virus expressing GM-CSF and GAL,V-R- together with the anti-PD-1 antibody or the anti-CTLA-4 antibody as compared to the other groups is observed, including through an improved dose response curve.

EXAMPLE 6

Collection of Clinical Isolates

The virus species used to exemplify the invention is HSV, specifically HSV1. To exemplify the invention, 181 volunteers were recruited who suffered from recurrent cold sores. These volunteers were given sample collection kits (including Sigma Virovult collection tubes), and used these to swab cold sores when they appeared following which these samples were shipped to Replimune, Oxford UK. From June 2015-February 2016, swabs were received from 72 volunteers. A sample of each swab was used to infect BHK cells. Of these 36 live virus samples were recovered following plating out and growth on BHK cells. These samples are detailed in Table 1.

TABLE 1

Details of Tested Swab Samples & Result

| Sample Number | Virus retrieved |
|---|---|
| RH001A | No |
| RH001B | |
| RH002A | Yes |
| RH003A | No |
| RH004A | Yes |
| RH004B | |
| RH005A | No |
| RH005B | |
| RH006A | No |
| RH006B | |

TABLE 1-continued

Details of Tested Swab Samples & Result

| Sample Number | Virus retrieved |
|---|---|
| RH007A | Yes |
| RH007B | |
| RH007C | |
| RH008A | No |
| RH008B | |
| RH008C | |
| RH009A | No |
| RH009B | |
| RH010A | No |
| RH011A | No |
| RH011B | |
| RH011C | |
| RH012A | No |
| RH013A | No |
| RH014A | Yes |
| RH014B | |
| RH015A | Yes |
| RH016A | No |
| RH016B | |
| RH017A | Yes |
| RH018A | Yes |
| RH018B | |
| RH018C | |
| RH019A | No |
| RH019B | |
| RH019C | |
| RH020A | Yes- RH020A only |
| RH020B | |
| RH020C | |
| RH021A | Yes |
| RH021B | |
| RH022A | Yes |
| RH022B | |
| RH023A | Yes |
| RH024A | No |
| RH025A | Yes -RH025B only |
| RH025B | |
| RH026A | Yes |
| RH027A | No |
| RH027B | |
| RH027C | |
| RH028A | No |
| RH028B | |
| RH028C | |
| RH029A | No |
| RH030A | No |
| RH031A | Yes - RH031A to RH031D |
| RH031B | |
| RH031C | |
| RH031D | |
| RH031E | |
| RH031F | |
| RH032A | No |
| RH033A | No |
| RH033B | |
| RH033C | |
| RH034A | No |
| RH034B | |
| RH034C | |
| RH035A | No |
| RH036A | Yes |
| RH037A | Yes |
| RH038A | Yes |
| RH039A | No |
| RH039B | |
| RH039C | |
| RH040A | Yes |
| RH040B | |
| RH040C | |
| RH041A | Yes |
| RH042A | Yes |
| RH043A | No |
| RH043B | |
| RH043C | |
| RH044A | No |
| RH045A | No |

TABLE 1-continued

Details of Tested Swab Samples & Result

| Sample Number | Virus retrieved |
|---|---|
| RH046A | Yes |
| RH047A | Yes- RH047A and |
| RH047B | RH047C |
| RH047C | |
| RH048A | No |
| RH049A | No |
| RH049B | |
| RH049C | |
| RH050A | No |
| RH051A | Yes |
| RH051B | |
| RH052A | Yes - RH052A only |
| RH052B | |
| RH053A | No |
| RH054A | No |
| RH055A | No |
| RH055B | |
| RH056A | Yes |
| RH057A | No |
| RH058A | Yes |
| RH058B | |
| RH059A | No |
| RH060A | No |
| RH061A | Yes |
| RH062A | No |
| RH063A | No |
| RH064A | Yes |
| RH065A | Yes |
| RH065B | |
| RH066A | No |
| RH067A | No |
| RH067B | |
| RH068A | No - contaminated |
| RH069A | No |
| RH069A | |
| RH070A | Yes |
| RH071A | Yes |
| RH072A | No |
| RH073A | Yes |
| RH073B | |
| RH074A | No |
| RH074B | |
| RH075A | No |
| RH076A | No |
| RH078A | No |
| RH078B | |
| RH079B | Yes |
| RH079B | |
| RH080A | No |
| RH081A | Yes |
| RH082A | No |
| RH082B | |
| RH083A | Yes |
| RH083B | |
| RH084A | Yes |
| RH084B | |
| RH084C | |
| RH085A | No |
| RH086A | No |
| RH087A | Yes - RH078B only |
| RH087B | |

Designations A, B, C etc. indicate multiple swabs from the same volunteer.

EXAMPLE 7

Identification of Clinical Isolates with Improved Anti-Tumor Effects

The abilities of the primary clinical isolates of HSV1 to kill a panel of human tumor-derived cell lines was tested. The tumor cell lines used for this comparison were HT29 (colorectal), MDA-MB-231 (breast), SK-MEL-28 (melanoma), Fadu (squamous cell carcinoma), MCF7 (breast), A549 (lung), MIAPACA-2 (pancreas) and HT1080 (fibrosarcoma). The cell lines were used to test for the level of CPE achieved at a range of MOI and times post infection for each of the primary clinical isolates.

Experiments were conducted in parallel using 5 to 8 of the new viruses strains at the same time. The virus strains were plated out in duplicate at a range of MOIs (0.001-1), and the extent of CPE following crystal violet staining was assessed at 24 and 48 hours following infection. The viral strains which were most effective at killing the tumor cell lines were scored, and the most effective two or three strains from each screen of 5-8 strains were identified and compared in parallel in a further experiment to identify the top strains for further development.

The initial screens demonstrated substantial variability in the ability of the different strains to kill the different tumor cell lines. Of an initial 29 strains tested, 8 strains of interest were identified in the initial screens for further comparison. These were strains RH004A, RH015A, RH018A, RH021A, RH023A, RH31A, RH040A, and RH047A.

Figure 3:
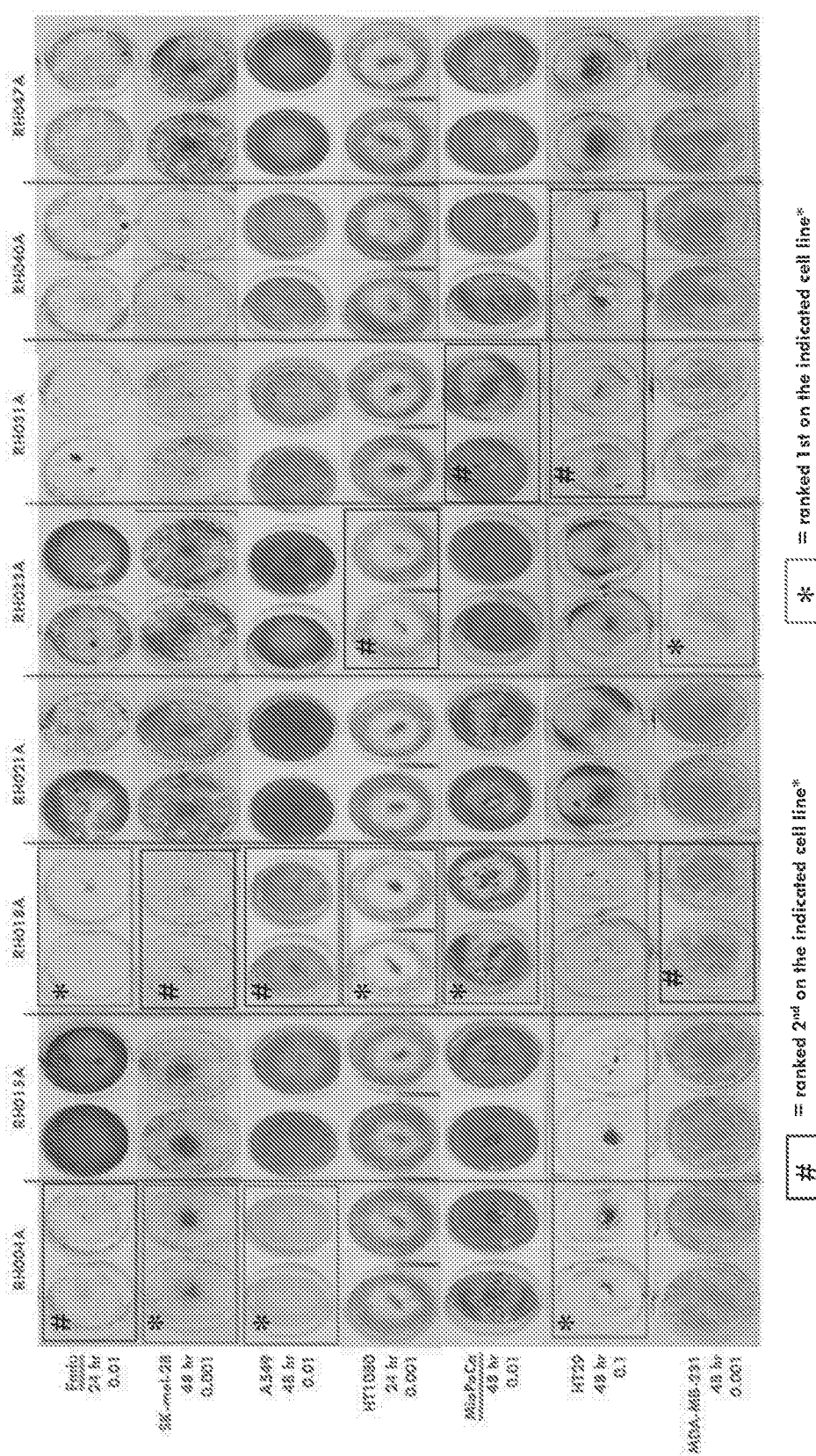
FIG. 3 shows the differential abilities of the eight top ranking HSV1 clinical isolate strains as assessed by crystal violet staining 24 hours or 48 hours after infection with a MOI of 0.1, 0.01 or 0.001 as indicated in the Figure to kill Fadu, SK-mel-28, A549, HT1080, MIA-PA-CA-2, HT29 and MDA-MB-23I human tumor cell lines. The virus strains ranked first and second on each cell line are indicated. The virus RH018A was ranked first on each of the Fadu, HT1080, MIA-PA-CA-2 and HT29 cell lines and second on each of the SK-mel-2.8, A549 and MDA-MB-231 cell lines. RH004A was ranked joint first with RH018A and RH015A on the HT29 cell line, first on the SK-mel-28 and A549 cell lines and second on the Fadu cell line, RI-1023A was ranked first on the MDA-MB-231 cell line and second on the HT1080 cell line. RH031A was ranked second on each of the MIA-PA-CA-2 and HT29 cell lines. RH040A was ranked joint second on the HT29 cell line.

The 8 strains for further comparison were tested in parallel on the panel of tumor cell lines, and their relative ability to kill these tumor cell lines was assessed following crystal violet staining and observation tbr CPE. FIG. 3 shows a representative time point and MOI for these viruses on each of the viruses on each of the cell lines demonstrating the differential ability of the viruses to kill the target tumor cell lines observed.

There was substantial variation amongst the strains, and it was found that while a particular strain may be particularly effective at killing one cell line, it is not necessarily particularly effective at killing other cell lines too, further demonstrating the degree of variability in the ability of clinical strains of HSV to kill tumor cells of different types.

FIG. 3 also indicates which of the virus strains was both best and second best at killing each of the cell lines, enabling the virus strains to be rank ordered as to their overall relative ability to kill the panel of cell lines as a whole. This analysis demonstrated that strains RH004A, RH015A, RH018A, RH031A and RH040A were relatively more effective than the other strains, and these five strains were chosen for potential further development as oncolytic agents. Of these top five strains, the relative rank order based on their abilities to kill across the panel of cell lines was RH018A>RH004A>RH031A>RH040A>RH015A.

More specifically, in these experiments, the tumor cell lines were used to seed multi-well tissue culture plates so that they were about 80% confluent on the day of infection. Representative wells from each tumor cell line were trypsinised and the number of cells in the well determined. These cell counts are used to determine the volume of each clinical isolate required to give an MOI of 1, 0.1, 0.01 and 0.001. Separate wells of a tumor cell line were infected with the clinical isolate at these MOI. All infections are carried out in quadruplicate. Duplicate wells were incubated for 24 hours and duplicate wells were incubated for 48 hours, both at 37° C., 5% $CO_2$, prior to fixation of the cells with glutaraldehyde and staining with crystal violet. The level of cell lysis was then assessed by gross observation, microscopy (cell counts) and photography.

Figure 4:
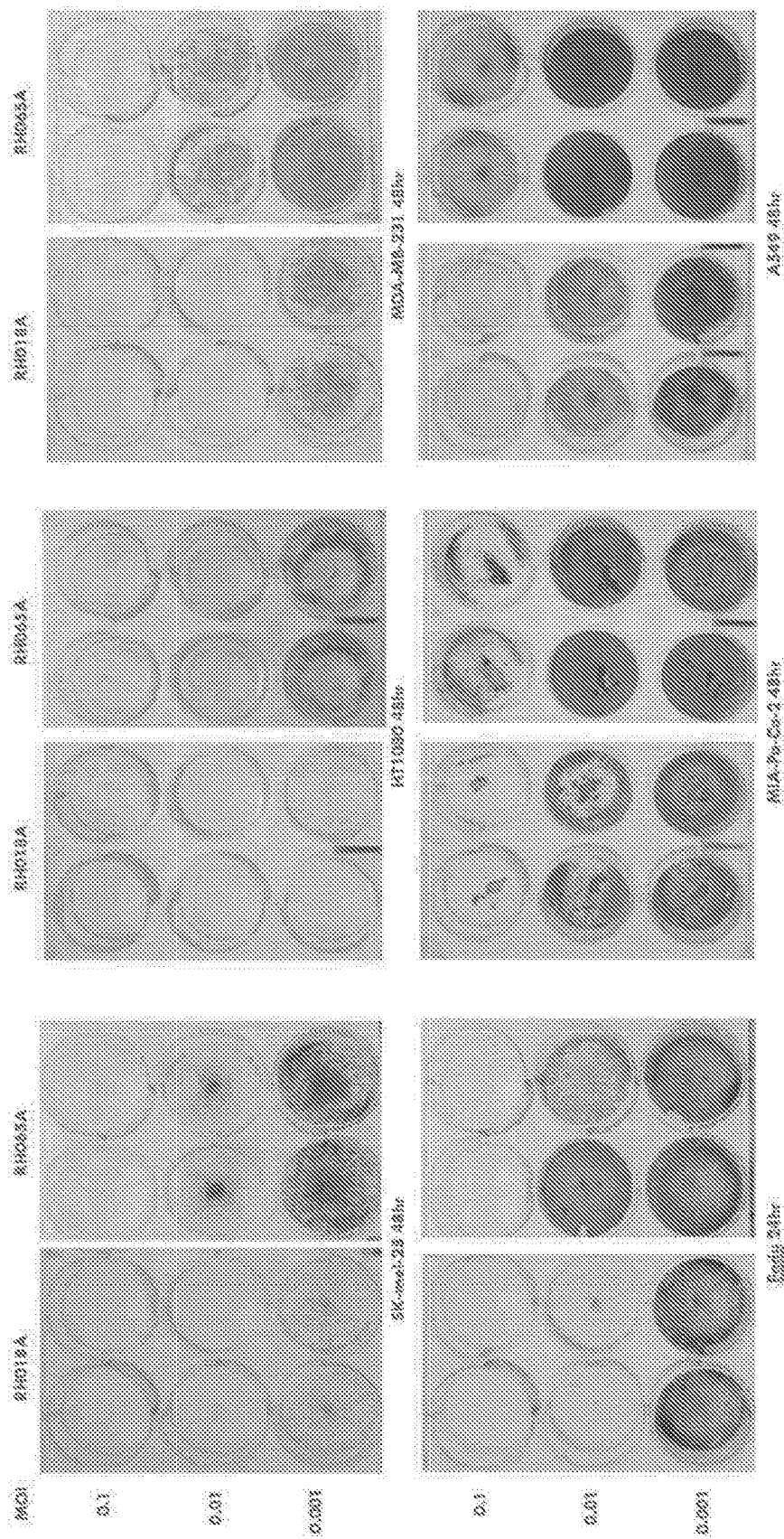
FIG. 4 shows a comparison between strain RH018A, the strain ranked first of all the strains tested, with an 'average' strain from the screen (i,e. strain RH065A). Approximately 10 fold less of strain RH018A was needed to kill an equal proportion of cells than was needed of strain RH065A as shown by crystal violet staining 24 or 48 hours post infection with MOIs of 0.1, 0.01 and 0.001 in SK-mel-28, HT1080, MDA-MB-231, Fadu, MIA-PA-CA-2 and A549 cell lines.
Figure 5A:
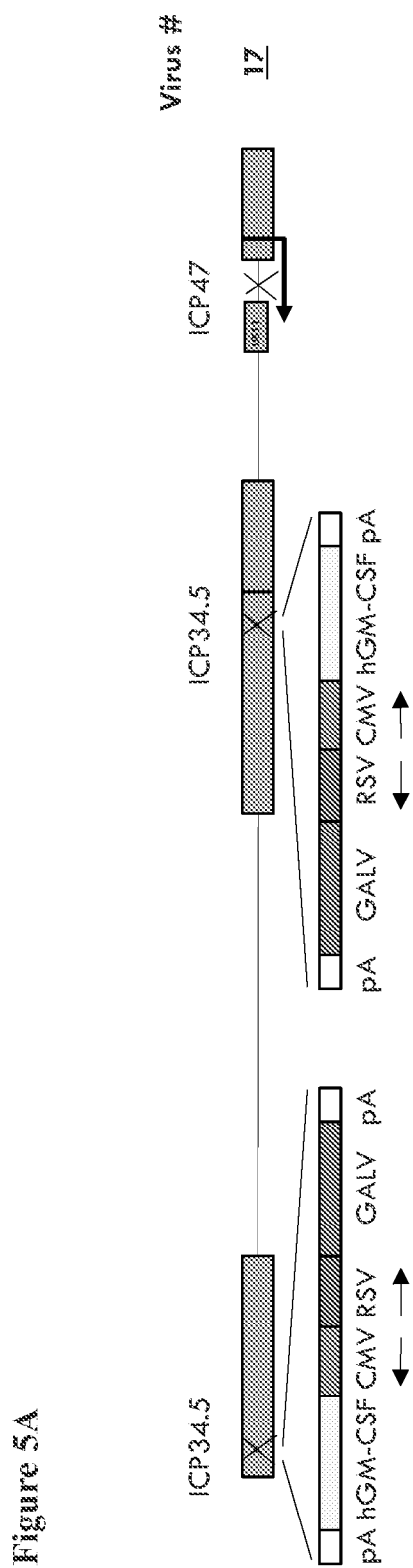
FIG. 5 depicts structures of HSV1 viruses modified by the deletion of ICP34.5 and ICP47 such that the US11 gene is under control of the ICP457 immediate early promoter and containing heterologous genes in the ICP34.5 locus. The viruses were constructed using the RH018A strain unless otherwise stated in the Figure.
Figure 5B:
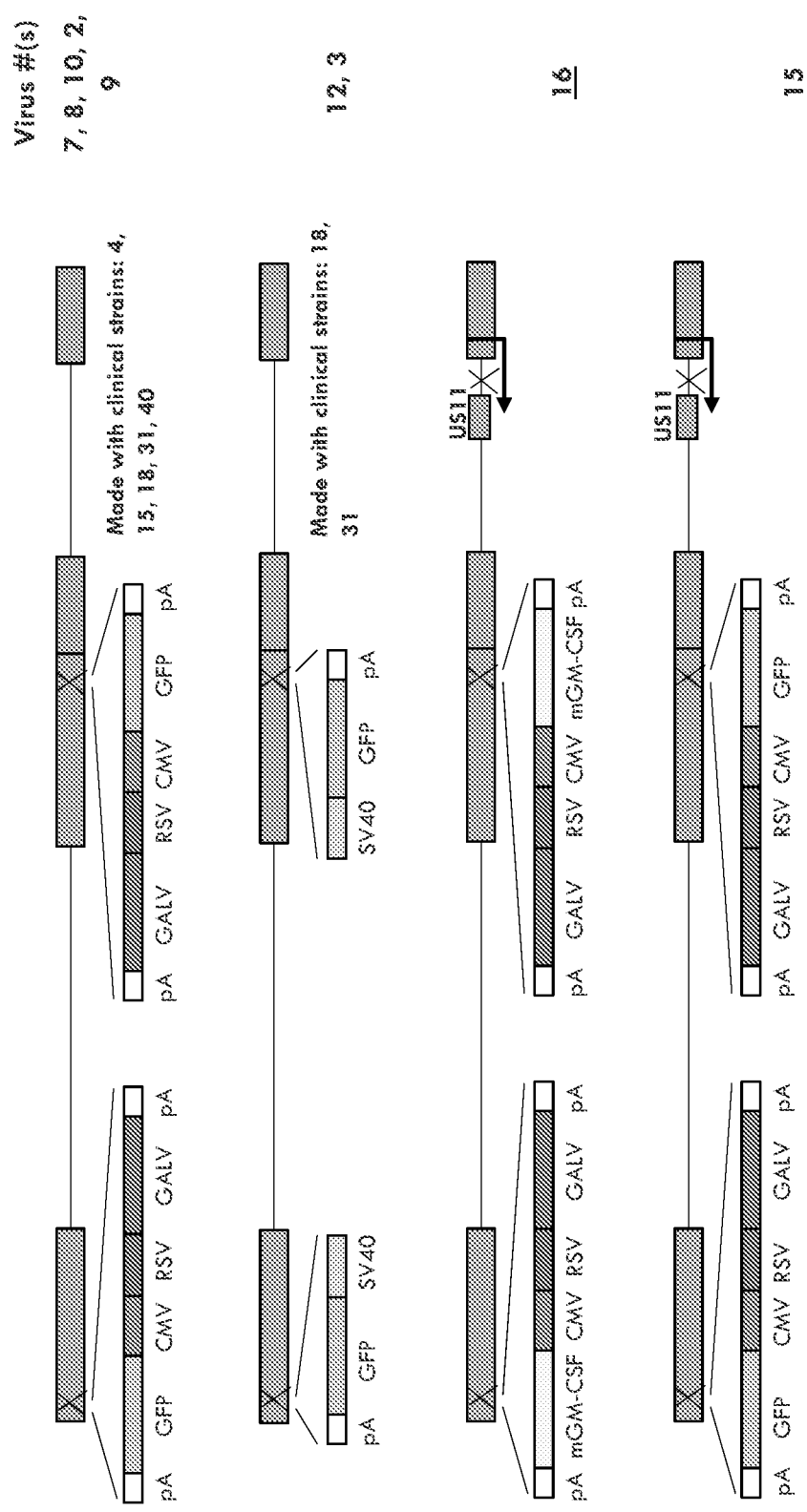
Figure 5C:
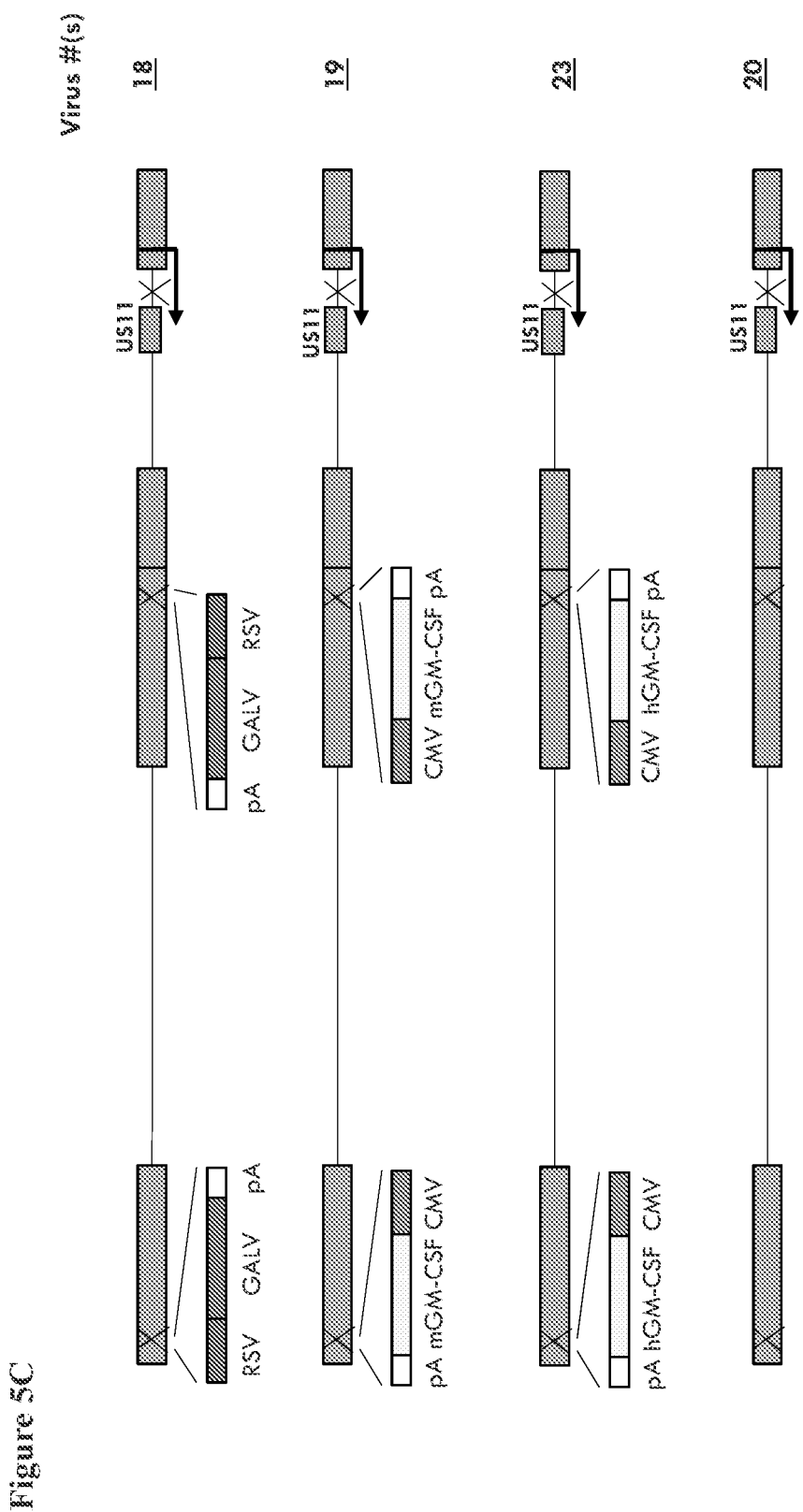
Figure 5D:
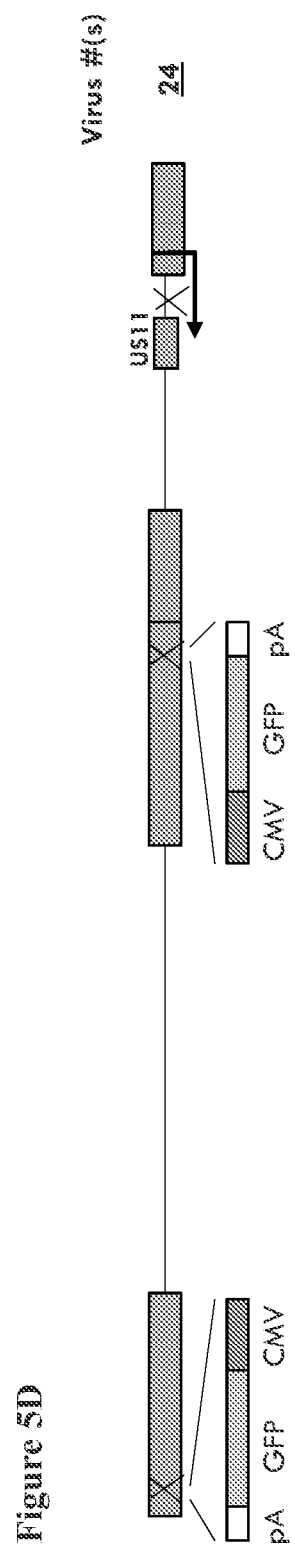
Figure 5E:
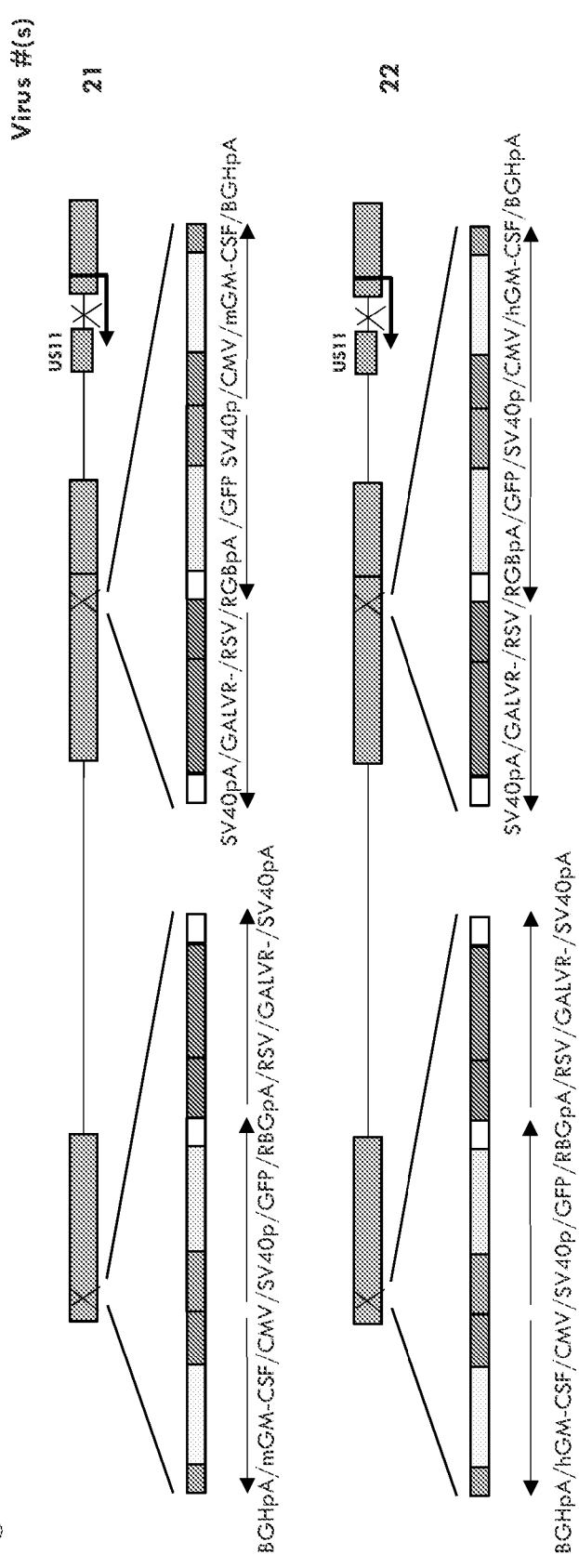
Figure 5F:
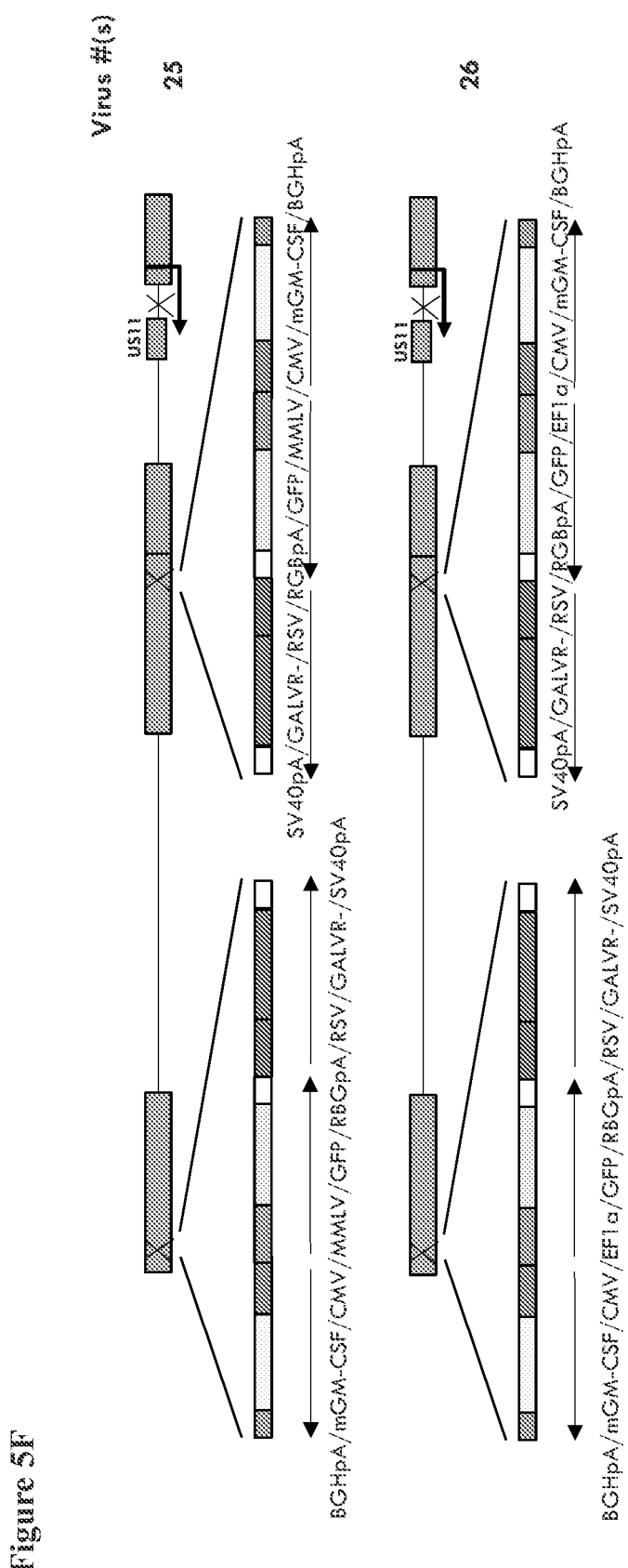
Figure 5G:
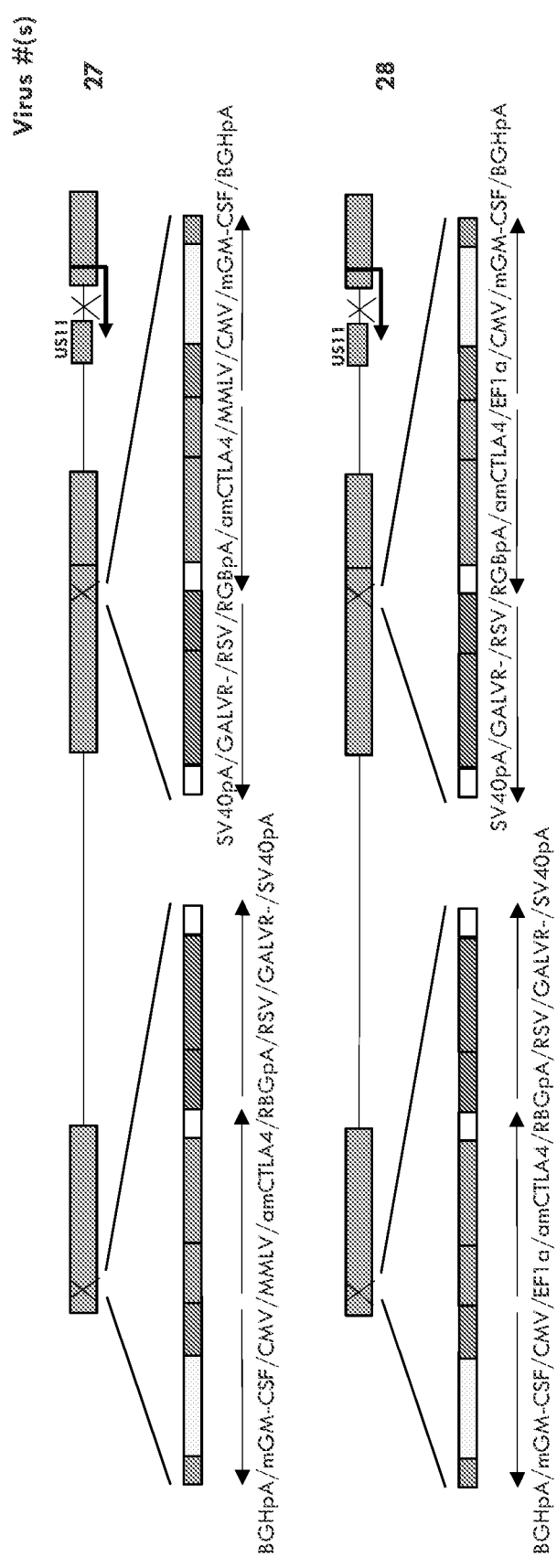
Figure 5L:
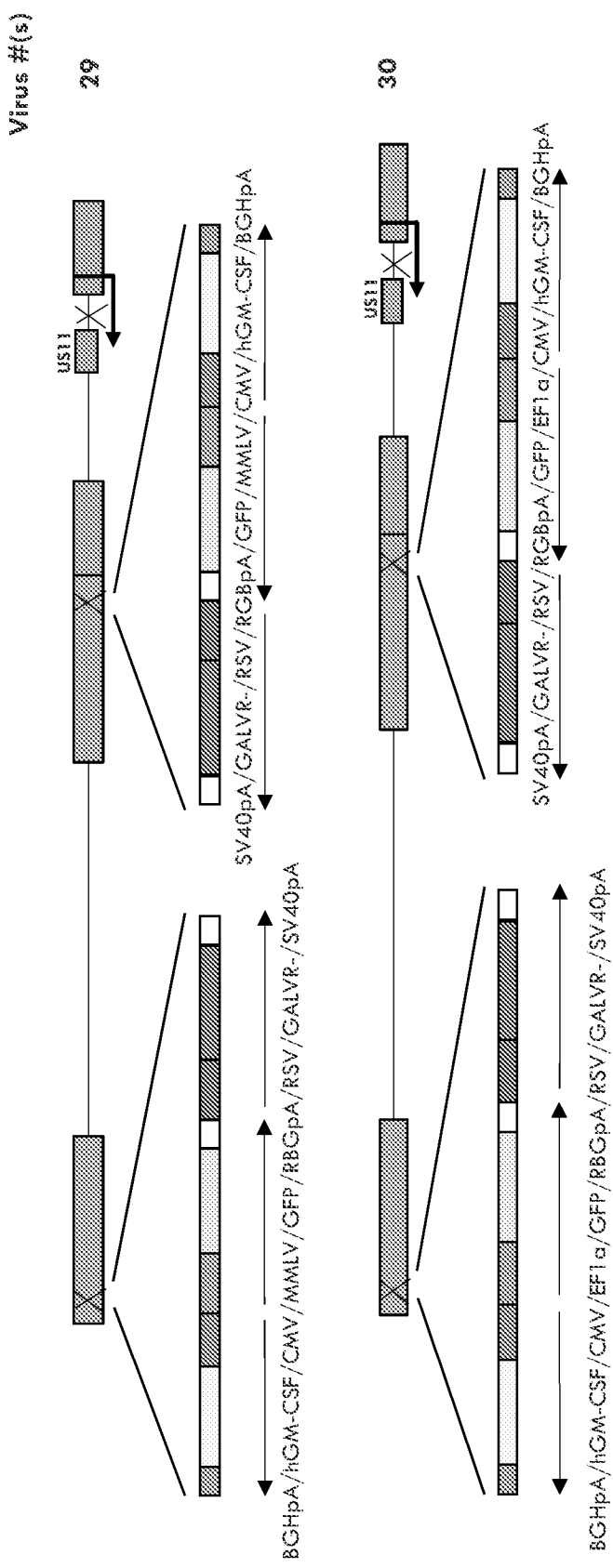
Figure 51:
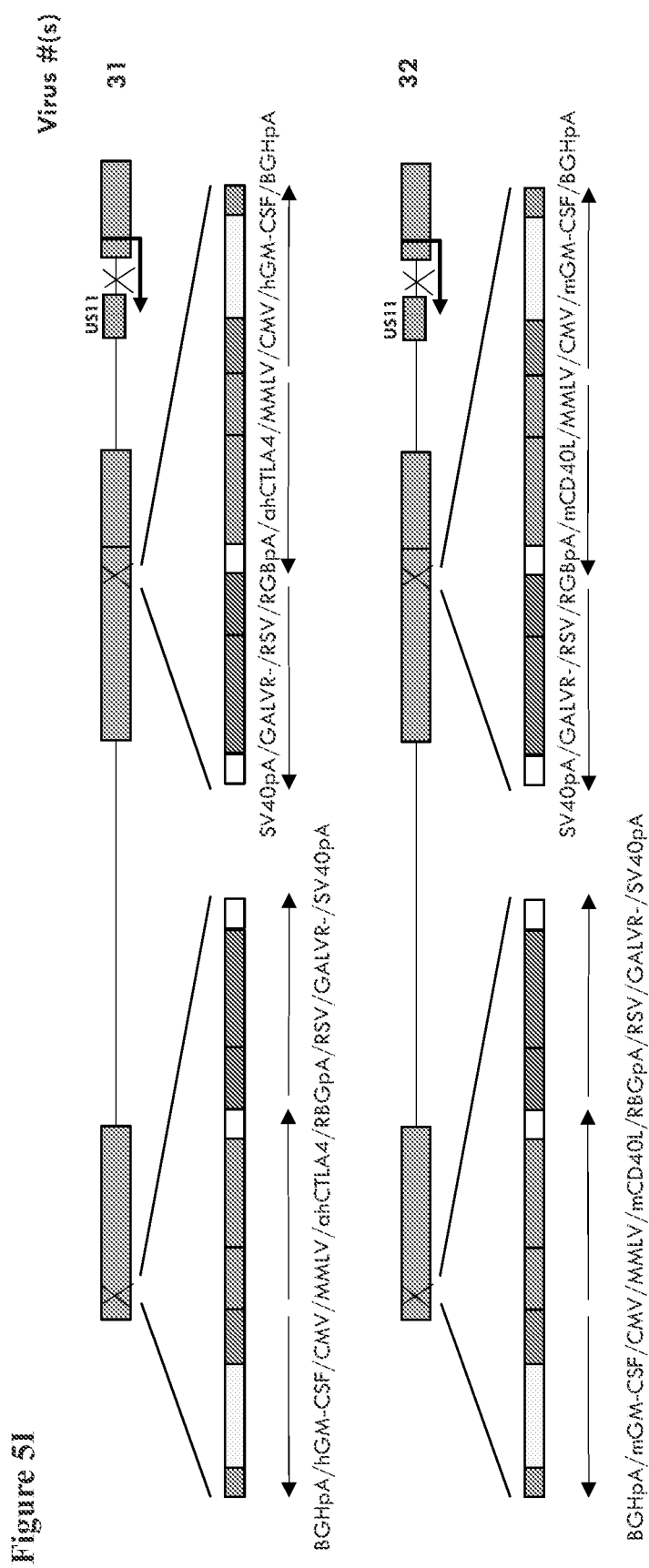
Figure 5J:
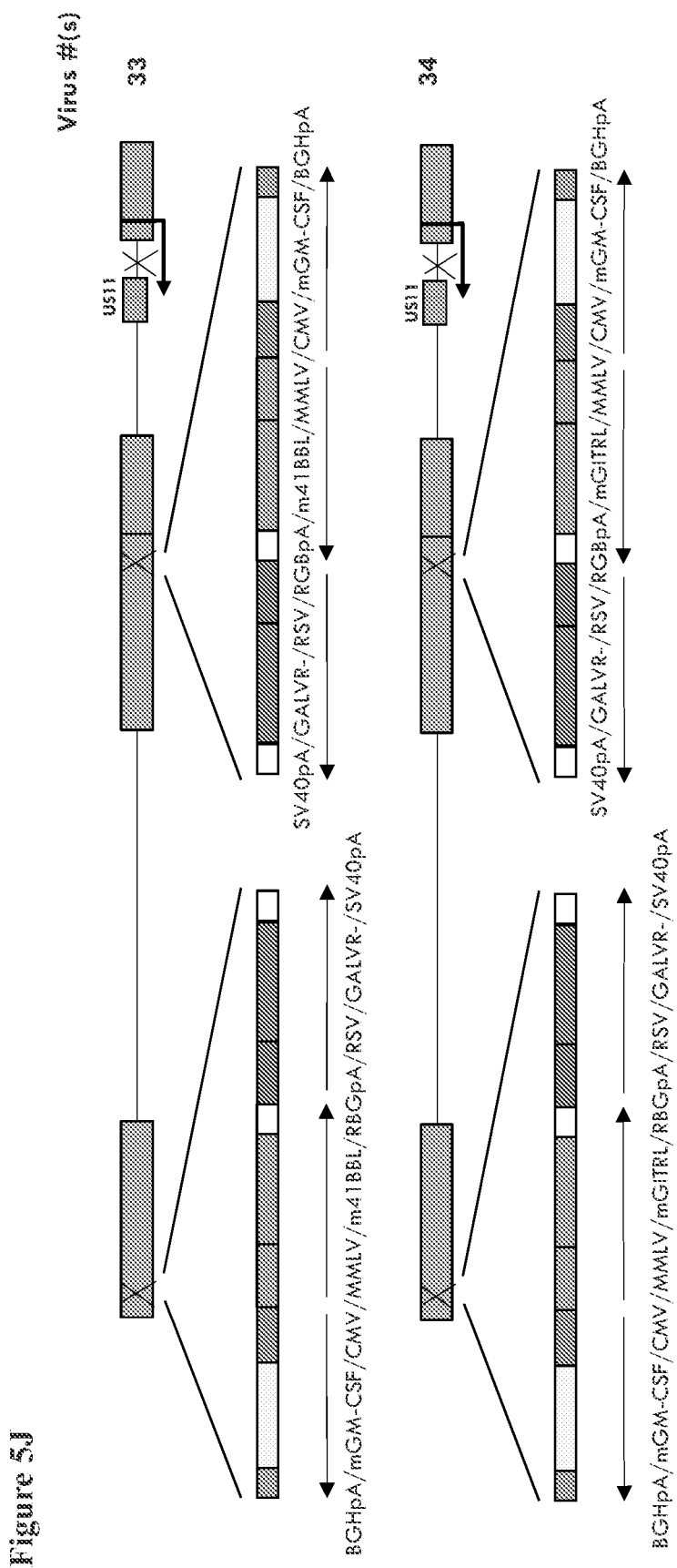
Figure 5K:
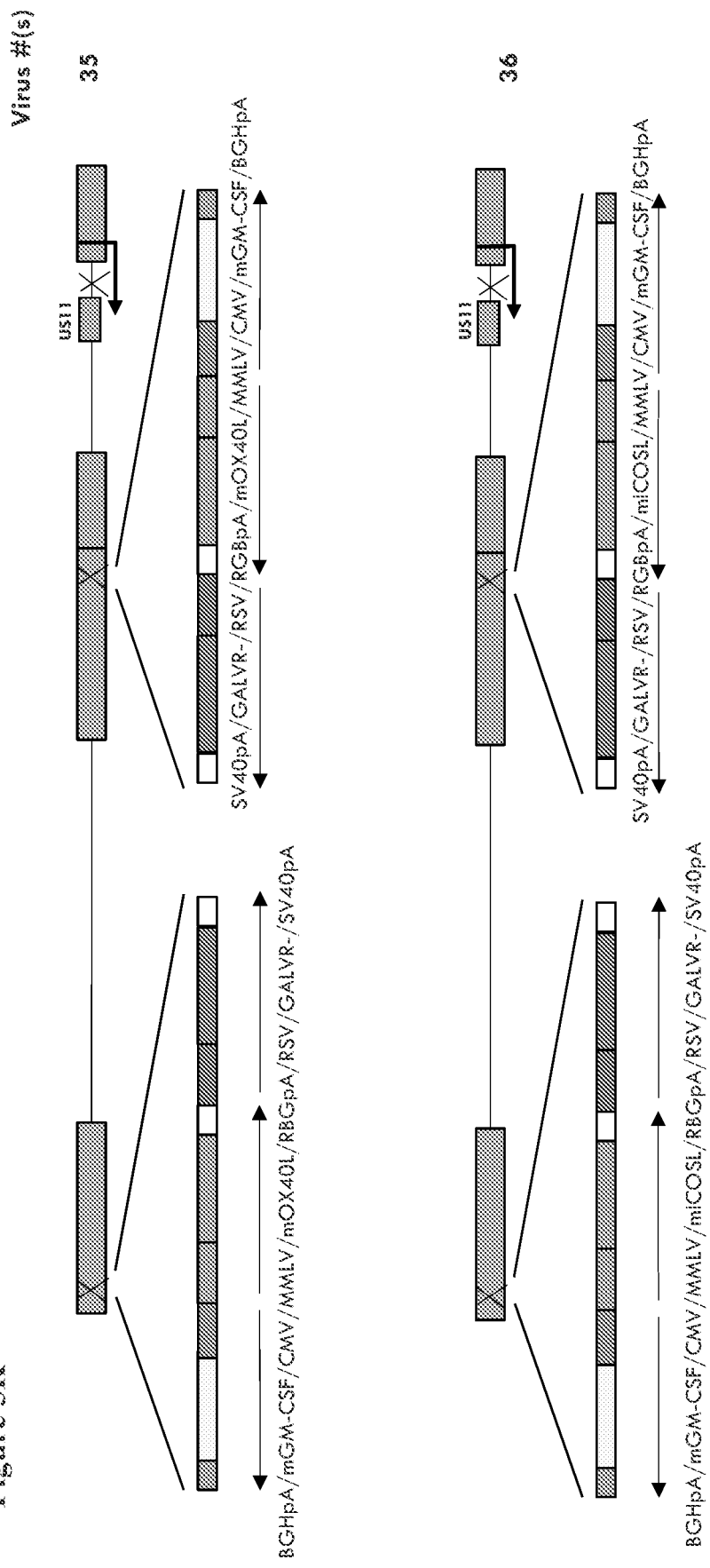

Strain RH018A, the strain ranked first of all the strains tested was compared to an 'average' strain from the screen (i.e. a strain which was not in the top 8, but was also not in the group of strains which were least effective and killing the panel of tumor cell lines). This comparison showed that Strain RH018A was approximately 10 fold more effective than this average strain (Strain RH065A) at killing the tumor cell lines (i.e. approximately 10 fold less of Strain RH018A was needed to kill an equal proportion of cells than was needed of Strain RH065A). This is shown in FIG. 4.

EXAMPLE 8

Modification of Clinical Isolates

In this Example the clinical isolates selected in Example 7 were modified by deletion of ICP34.5 from the viral genome using homologous recombination with a plasmid containing regions flanking the ICP34.5 encoding gene (nucleotides 143680-145300 and 145,582-147,083; HSV1 strain 17 sequence Genbank file NC_001806.2) between which are encoded GFP and the GALV-R-fusogenic glycoprotein. The structure of this virus, (Virus 10) is shown in FIG. 5.

Additional viruses based on Strain RH018A were also constructed in which both ICP34.5 and ICP47 (using flanking regions containing nucleotides 123464-124953 and 125727-126781; HSV1 strain 17 sequence Genbank file NC_001806.2) were deleted (resulting in placement of US11 under the control of the ICP47 promoter). To construct these viruses, GFP expressing virus plaques, with GFP expressed in place of IC47 were first selected. GFP was then removed by homologous recombination with the empty flanking regions, and plaques not expressing GFP were selected. This resulted in an ICP47 deleted virus in which US11 is expressed as an IE protein as it is now under the control of the ICP47 promoter. ICP34.5 was then deleted using homologous recombination with a plasmid containing regions flanking HSV1 nucleotides 143680-145300 and 145,582-147,083; HSV1 strain 17 sequence Genbank tile NC_001806.2) between which GFP is encoded. GFP expressing virus plaques were again selected, and GFP then removed by homologous recombination with the same flanking regions but between which are now an expression cassette comprising the genes to be inserted. The viruses that were constructed are shown in FIGS. 1 and 5. These included a codon optimized version of the mouse GM-CSF sequence and a codon optimized version of the GALV R- sequence driven by the CMV IE promoter and RSV promoter respectively, in a back to back orientation and again selecting virus plaques which do not express GFP. This virus construction was performed using methods which are standard in the art.

The mGM-CSF and GALV-R- sequences are shown in SEQ ID NOs 2 and 8 respectively. The structure of the resulting virus was confirmed by PCR, GM-CSF expression was confirmed by ELISA, and GALV-R- expression was confirmed by infection of human HT1080 tumor cells and the observation of syncitial plaques.

For human use, hGM-CSF is used, the sequence for a codon optimised version of which is shown in SEQ ID NO 4. The structure of this virus is shown in FIG. 5. Expression of mouse or human GM-CSF from viruses 16, 17 and 19 is shown in FIG. 6.

EXAMPLE 9

A Virus of the in Modified for Oncolytic Use and Expressing a Fusogenic Glycoprotein Shows Enhanced Tumor Cell Killing In Vitro as Compared to a Virus Which Does Not Express a Fusogenic Glycoprotein Virus 10 (see FIG. 5), based on clinical Strain RH018A in which ICP34.5 is deleted and which expresses GALVR- and GFP, was compared in vitro to a virus which expresses only GFP (Virus 12). Virus 10 showed enhanced killing on a panel of human tumor cell lines as compared to Virus 12, as shown in FIG. 7.

EXAMPLE 10

Figure 8A:
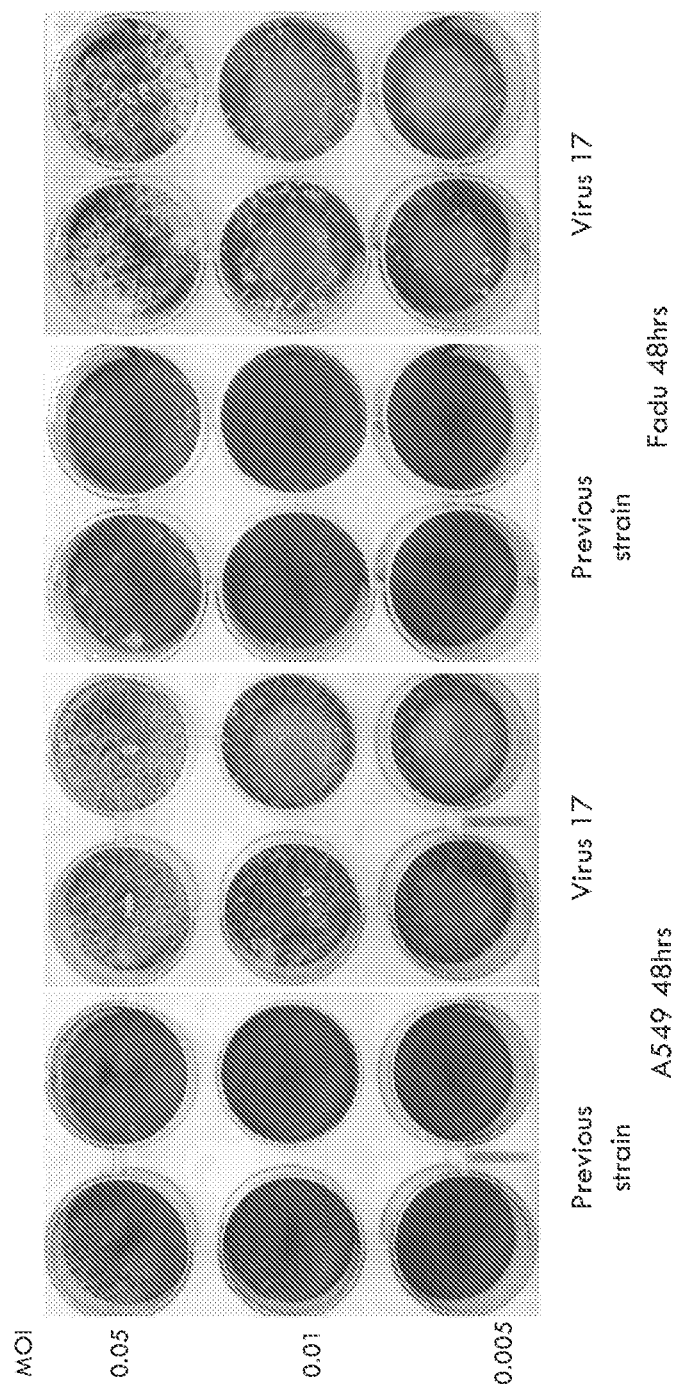
FIG. 8 is a comparison between the cell-killing abilities of strain RH018A in which ICP34.5 and ICP47 are deleted and which expresses GALVR- and GM-CSF (virus 17) with a prior art strain with the same modifications as determined by crystal violet staining in four cell lines.
Figure 8B:
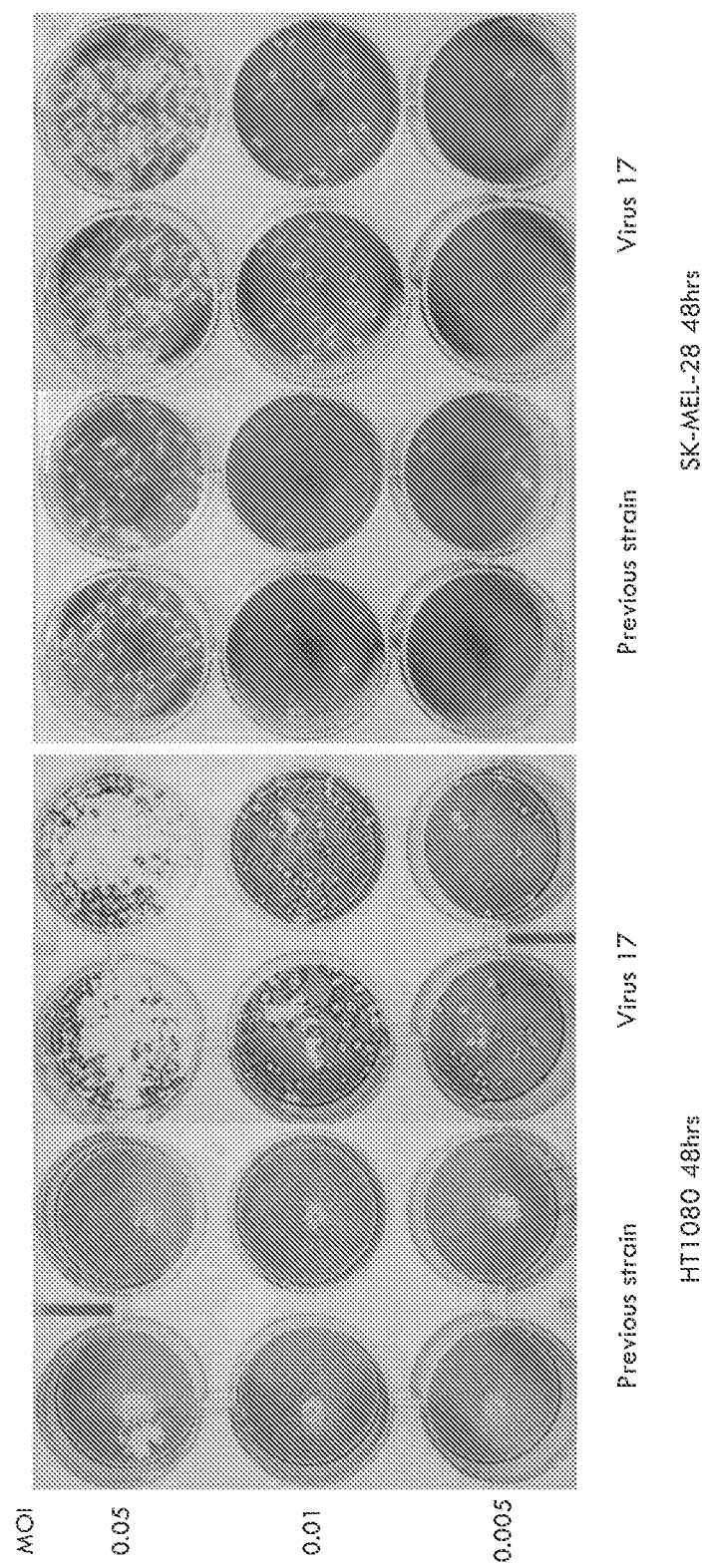

A Virus of the Invention Modified for Oncolytic Use Shows Enhanced Tumor Cell Killing as Compared to a Similarly Modified Virus Which is Not of the Invention Virus 17 (see FIG. 5), based on clinical Strain RH018A in which ICP34.5 and ICP47 are deleted and which expresses GALVR- and GM-CSF, was compared in vitro to a known virus which was also deleted for ICP34.5 and ICP47 but which was not derived from a strain of the invention and which expresses only GM-CSF. Virus 17 showed enhanced killing on a panel of human tumor cell lines as compared to the previous virus, as shown in FIG. 8.

EXAMPLE 11

Figure 9:
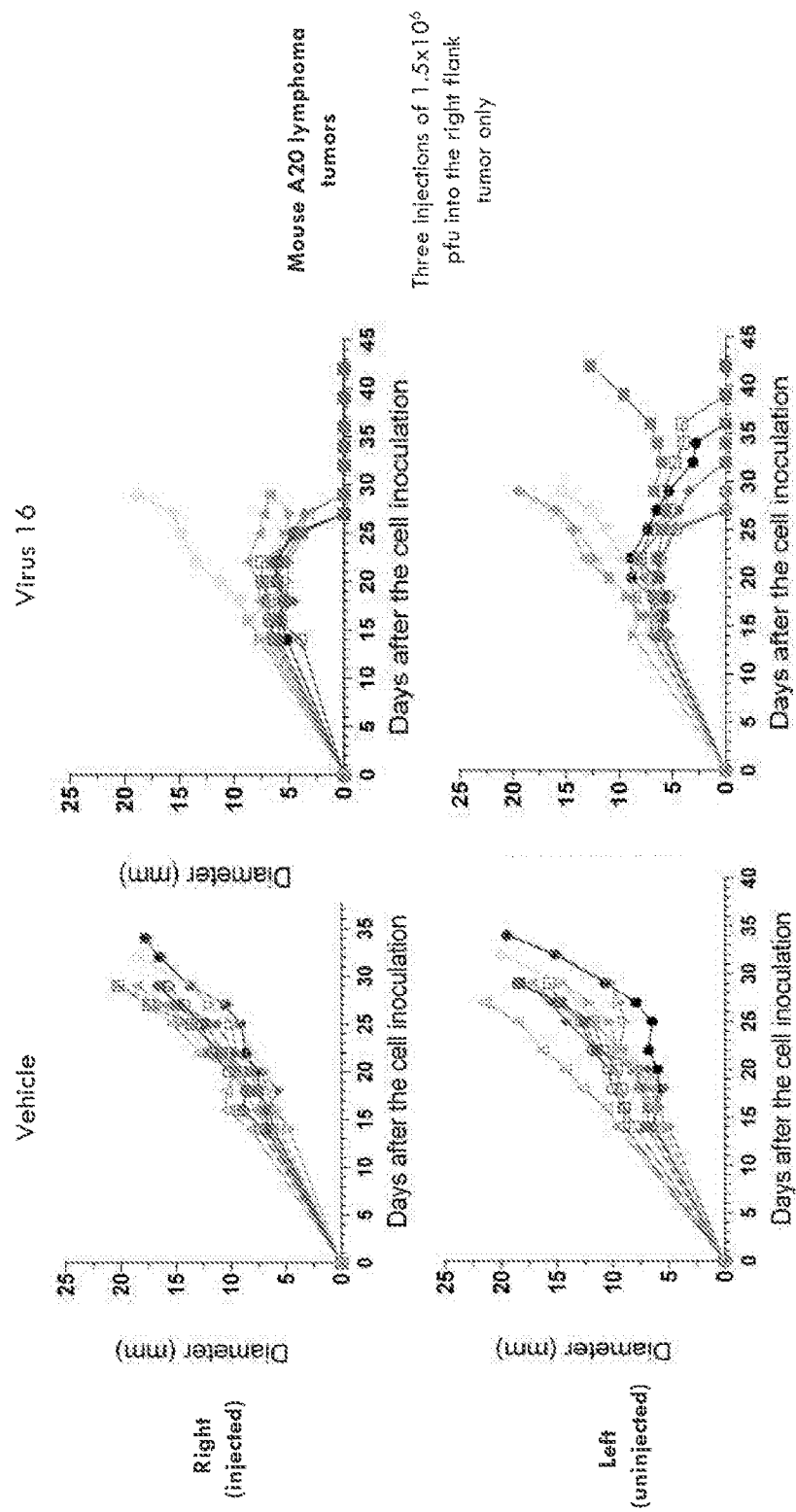
FIG. 9 shows the effectiveness of Virus 16 (ICP34.5 and ICP47 deleted expressing GALVR- and mGM-CSF) in treating mice harbouring A20 lymphoma tumors in both flanks. Tumors on the right flanks were injected with the virus or vehicle and the effects on tumor size was observed for 30 days. The virus was effective against both injected tumors and non-injected tumors.

A Virus of the Invention Modified for Oncolytic Use Effectively Treats Mouse Tumors In Vivo Virus 16 was tested in mice harboring A20 lymphoma tumors in the left and right flanks. One million tumor cells were first implanted in both flanks of Balb/c mice and tumors allowed to grow to 0.5-0.7 cm in diameter. Tumors on the right flank were then injected 3 times (every other day) with either vehicle (10 mice) or 5×10exp6 pfu of Virus 16 (10 mice), and effects on tumor size observed for a further 30 days. This demonstrated that both injected and uninjected tumors were effectively treated with Virus 16 (see FIG. 9).

EXAMPLE 12

The Effect of the Combined Expression of a Fusogenic Protein and an Immune Stimulatory Molecule from an Oneolytic Virus of the Invention in a Rat Tumor Model The GALV R- protein causes cell to cell fusion in human cells but not in mouse cells. However, GALV R- does cause fusion in rat cells.

The utility of the invention was further demonstrated by administering 9L cells into the flanks of Fischer 344 rats and allowing the 9L tumors to grow to approximately 0.5 cm in diameter.

The following treatments were then administered to groups of rats (ten per group), into one flank only of each rat three times per week for three weeks:
  50 µl of vehicle;
  50 µl of $10^7$ pfu/ml of Virus 19 (expresses mGM-CSF but not GALV R-);
  50 µl of $10^7$ pfu/ml of Virus 16 (expresses both mouse GM-CSF and GALV-R-).

Figure 10:
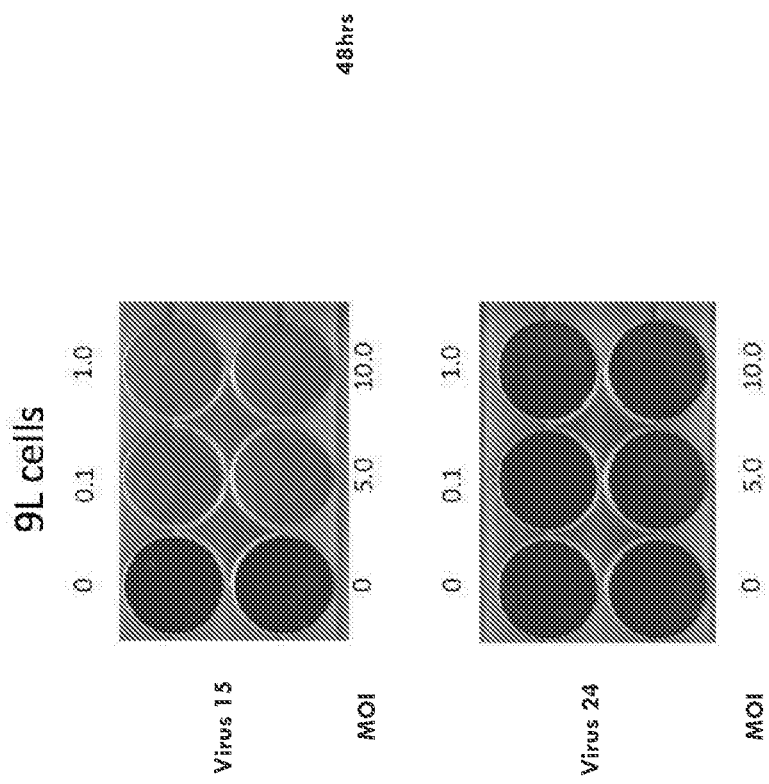
FIG. 10 demonstrates the effects of Virus 15 (ICP34.5 and ICP47 deleted expressing GALVR- and GFP) and Virus 24 (ICP34.5 and ICP47 deleted expressing GFP) on rat 9L cells in vitro as assessed by crystal violet staining. The virus expressing GALV (Virus 15) showed enhanced killing of rat 9L cells in vitro as compared to a virus which does not express GALV (Virus 24).
Figure 15:
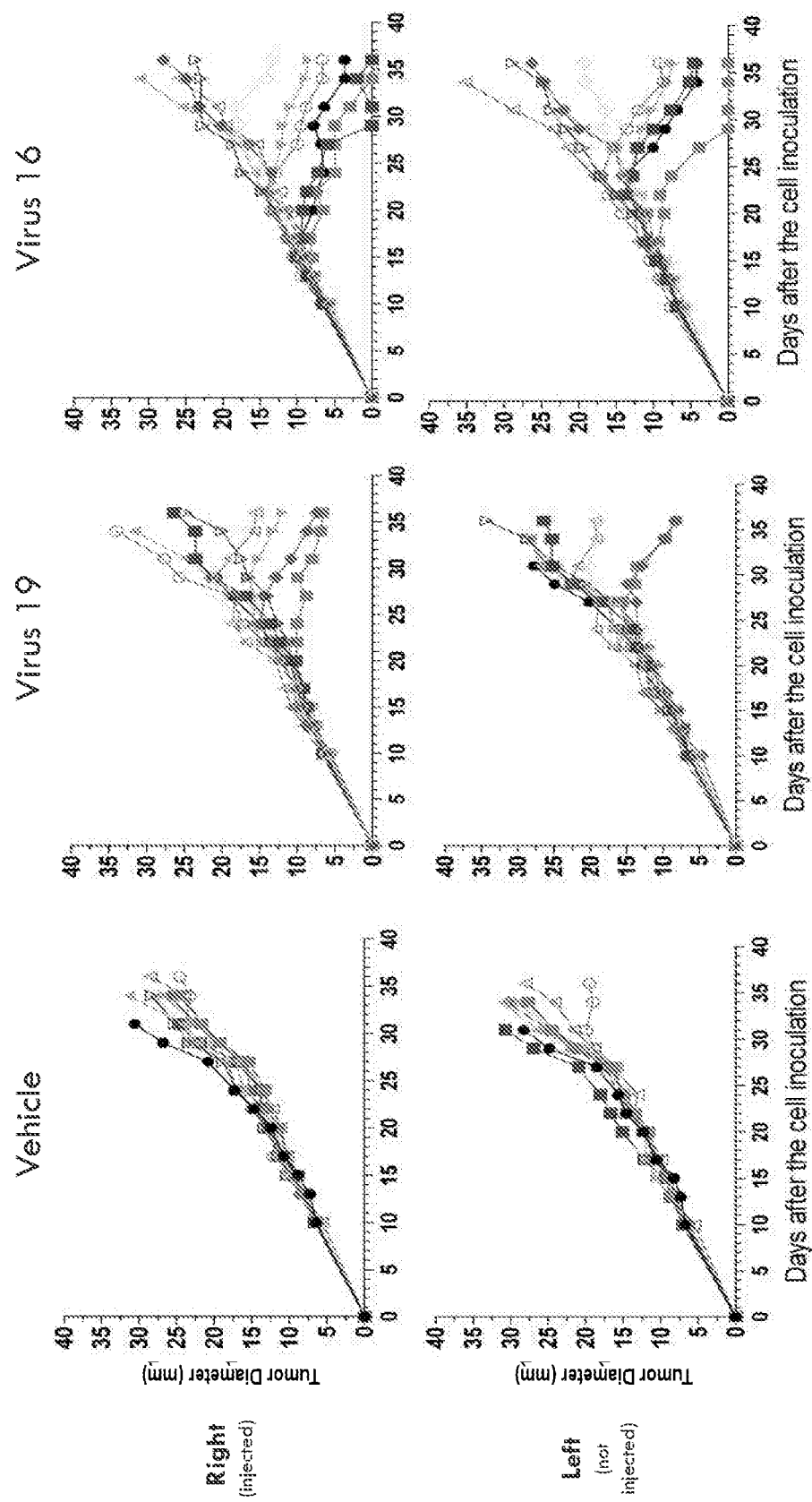
FIG. 15 demonstrates the effects of viruses of the invention expressing GALVR- on 9L cells in the flanks of Fischer 344 rats. The following treatments were administered to groups of rats (ten per group), into one flank of each rat only three times per week for three weeks: 50 μl of vehicle; 50μl of 10$^7$ pfu/ml of Virus 19 (expresses mGM-CSF but not GALV R-); or 50μl of 10$^7$ pfu/ml of Virus 16 (expresses both mouse GM-CSF and GALV-R-). Effects on tumor growth were then observed for a further 30 days. Superior tumor control and shrinkage was observed with the virus expressing GM-CSF and GALV-R- as compared to the virus expressing GM-CSF alone.

Effects on tumor growth were then observed for a further ≈30 days. This demonstrated superior tumor control and shrinkage with the virus expressing GALV-R in both injected and uninjected tumors, demonstrating improved systemic effects. This is shown in FIG. 15. FIG. 10 shows that a virus expressing GALV (Virus 15) also shows enhanced killing of rat 91 cells in vitro as compared to a virus which does not express GALV (Virus 24).

EXAMPLE 13

A Virus of the Invention Modified for Oncolytic Use is Synergistic with Immune Checkpoint Blockade in Mouse Tumor Models Virus 16 was tested in mice harboring CT26 tumors in the left and right flanks. One million tumor cells were first implanted in both flanks of Balb/c mice and tumors allowed to grow to 0.5-0.6 cm in diameter.

Groups of 10 mice were then treated with:
Vehicle (3 injections into right flank tumors every other day);
5×10exp6 pfu of Virus 16 injected in the right flank tumor every other day;
anti-mousePD1 alone (10 mg/kg i.p. every three days, BioXCell clone RMP1-14);
anti-mouseCTLA-4 (3 mg/Kg i.p every three days, BioX-Cell clone 9D9);
anti-mousePD1 together with Virus 16;
anti-mouseCLTA4 together with Virus 16;
1-methyl trypotophan (IDO inhibitor (5 mg/ml in drinking water));
anti-mouse P1)1 together with 1-methyl trypotophan;
anti-mouse PD1 together with 1-methyl trypotophan and Virus 16;

Effects on tumor size were observed for a further 30 days. A greater tumor reduction in animals treated with combinations of virus and checkpoint blockade was demonstrated than in animals treated with the single treatment groups (see FIG. 11). Enhanced tumor reduction with Virus 16 together with both anti-PD1 and IDO inhibition was also demonstrated as compared to Virus 16 together with only anti-PD1 (see FIG. 11).

Figure 12A:
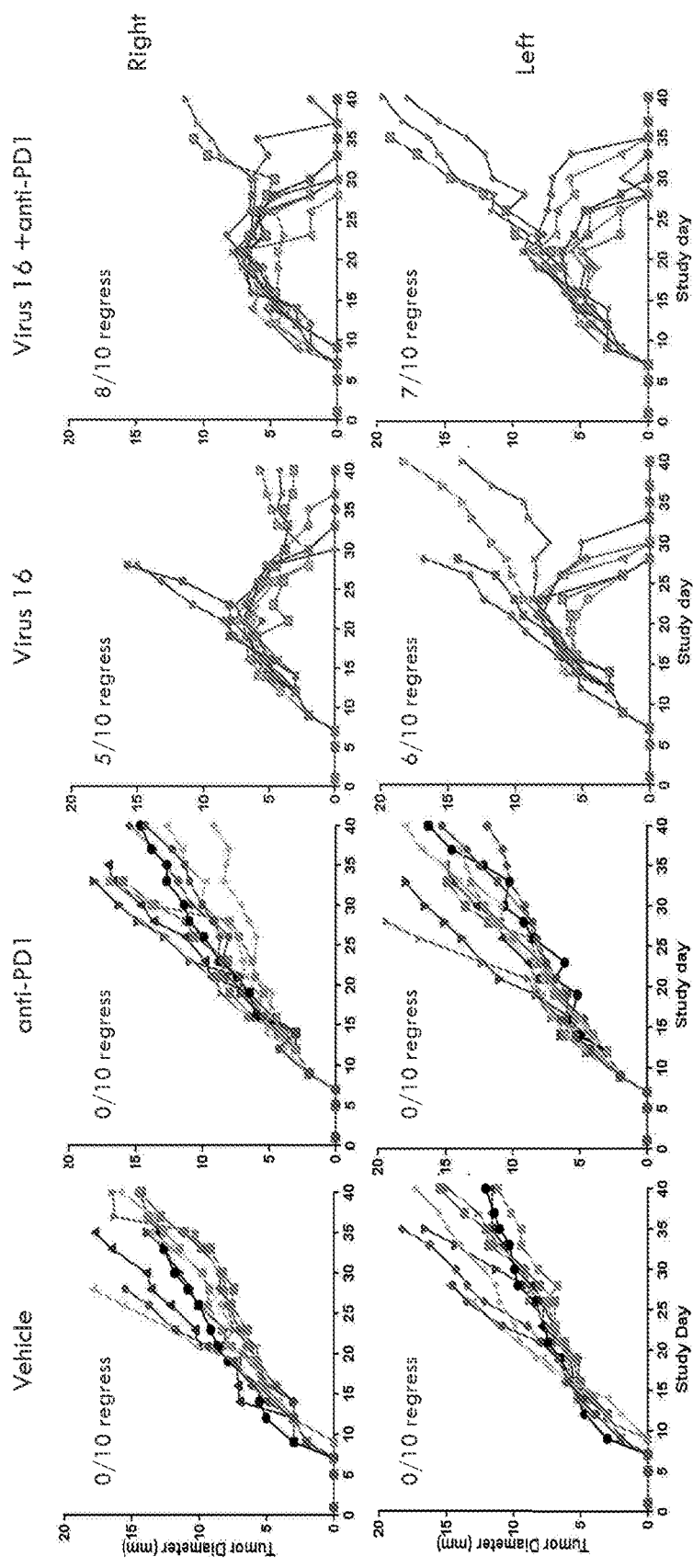
FIG. 12 shows the enhanced anti-tumor activity of Virus 16 in combination with immune checkpoint blockade in mouse A20 tumors in both flanks of Balb/c mice as compared to either virus alone or checkpoint blockade alone (anti-PD1).
Figure 12B:
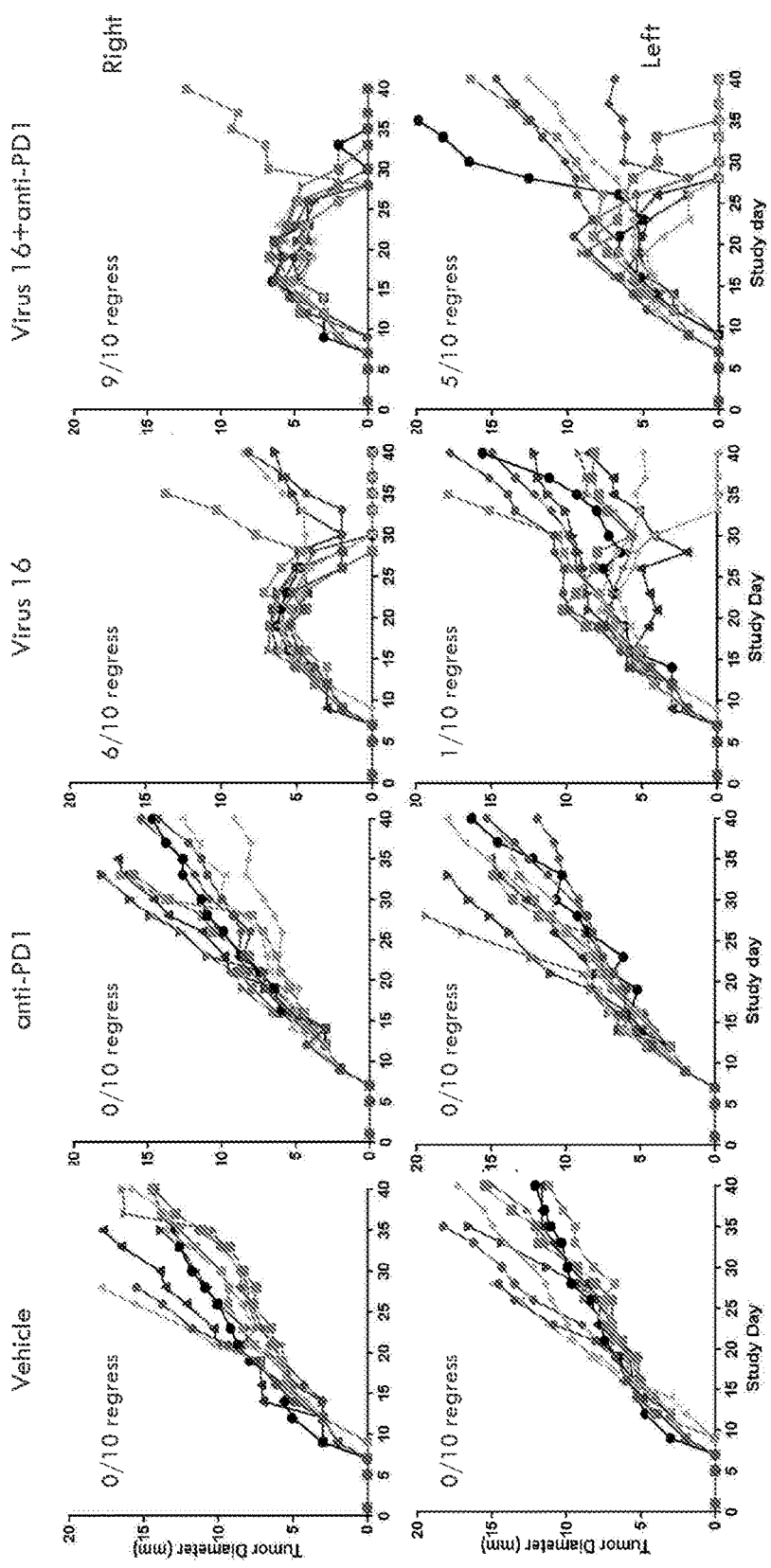
Figure 12C:
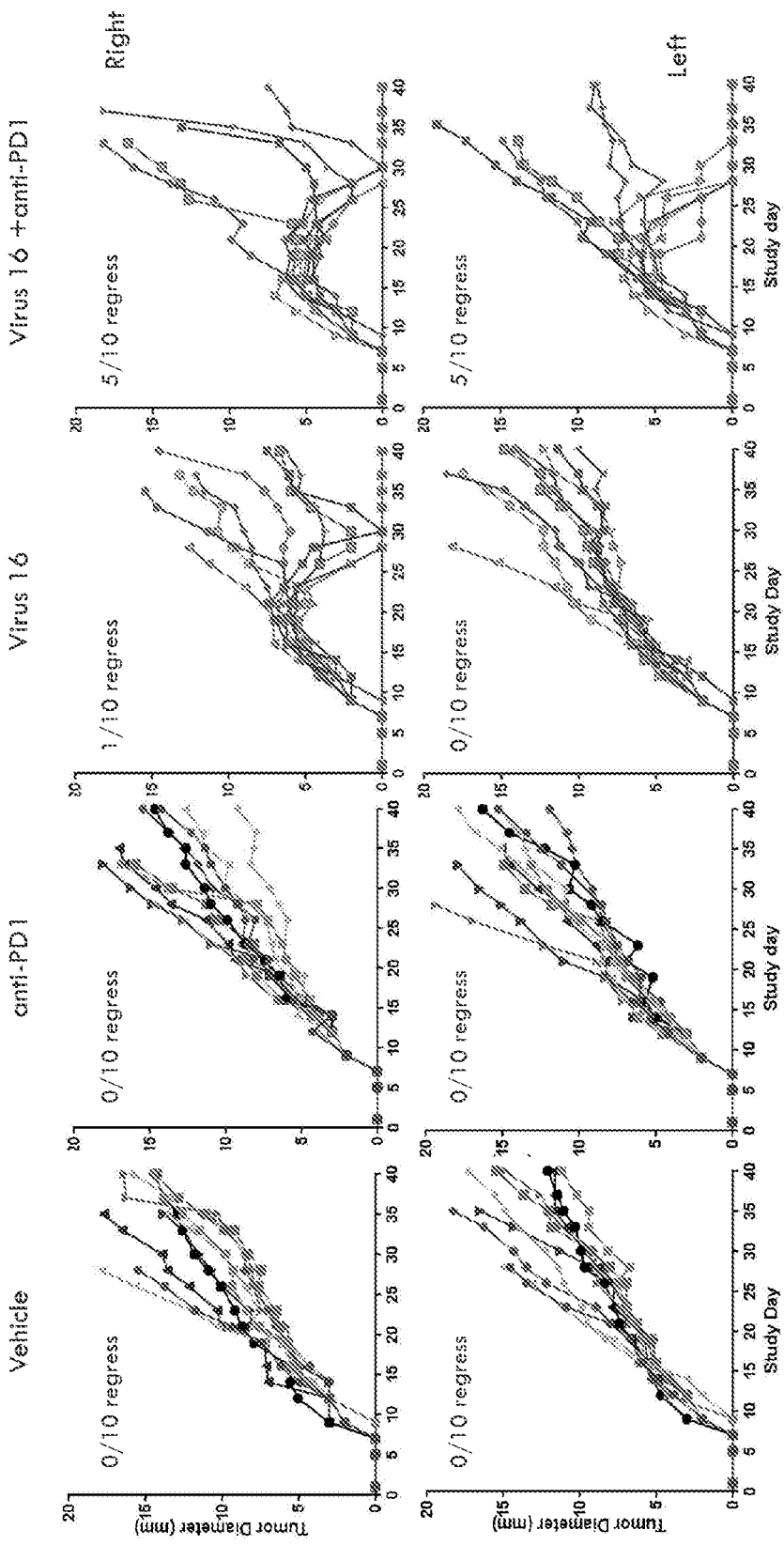

Enhanced activity of Virus 16 in combination with immune checkpoint blockade was also seen in A20 tumors (FIG. 12).

EXAMPLE 14

The Effect of the Expression of a Fusogenic Protein from an Oncolytic Virus of the Invention in Human Xenograft Models in Immune Deficient Mice The GALV R- protein causes cell to cell fusion in human cells but not in mouse cells. However, human xenograft tumors grown in immune deficient mice can be used to assess the effects of GALV expression on anti-tumor efficacy.

The utility of the invention was therefore further demonstrated by administering A549 human lung cancer cells into the flanks of nude mice and allowing the tumors to grow to approximately 0.5 cm in diameter.

The following treatments were then administered to groups of mice (ten per group), into tumor containing flank of each mouse three times over one week:
50 µl of vehicle;
50 µl of $10^7$ pfu/ml of Virus 16 (expresses both mouse GM-CSF and GALV-R-);
50 µl of $10^6$ pfu/ml of Virus 16;
50 µl of $10^5$ pfu/ml of Virus 16;
50 µl of $10^7$ pfu/ml of Virus 19 (expresses only mouse GM-CSF);
50 µl of $10^6$ pfu/ml of Virus 19;
50 µl of $10^5$ pfu/ml of Virus 19.

Figure 14:
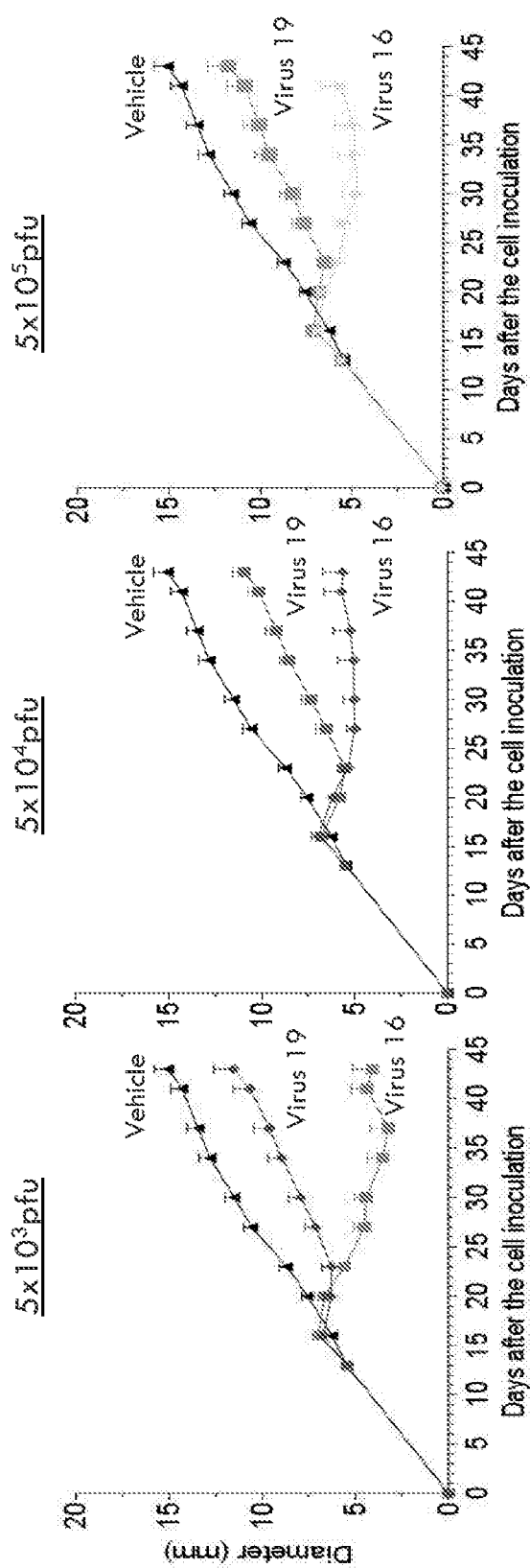
FIG. 14 shows anti-tumor effects of Virus 16 and Virus 19 in a human xenograft model (A549). There were three injections of Virus 16, Virus 19 or of vehicle over one week at three different dose levels (N=10/group). The doses of the viruses used is indicated. The anti-tumor effects of Virus 16 which expresses GALV were better than those of Virus 19 which does not express GALV.

Effects on tumor growth were then observed for a further ≈30 days. This experiment demonstrated superior tumor control and shrinkage with the virus expressing GALV-R- in both tumor models (see FIG. 14).

EXAMPLE 15

Figure 13:
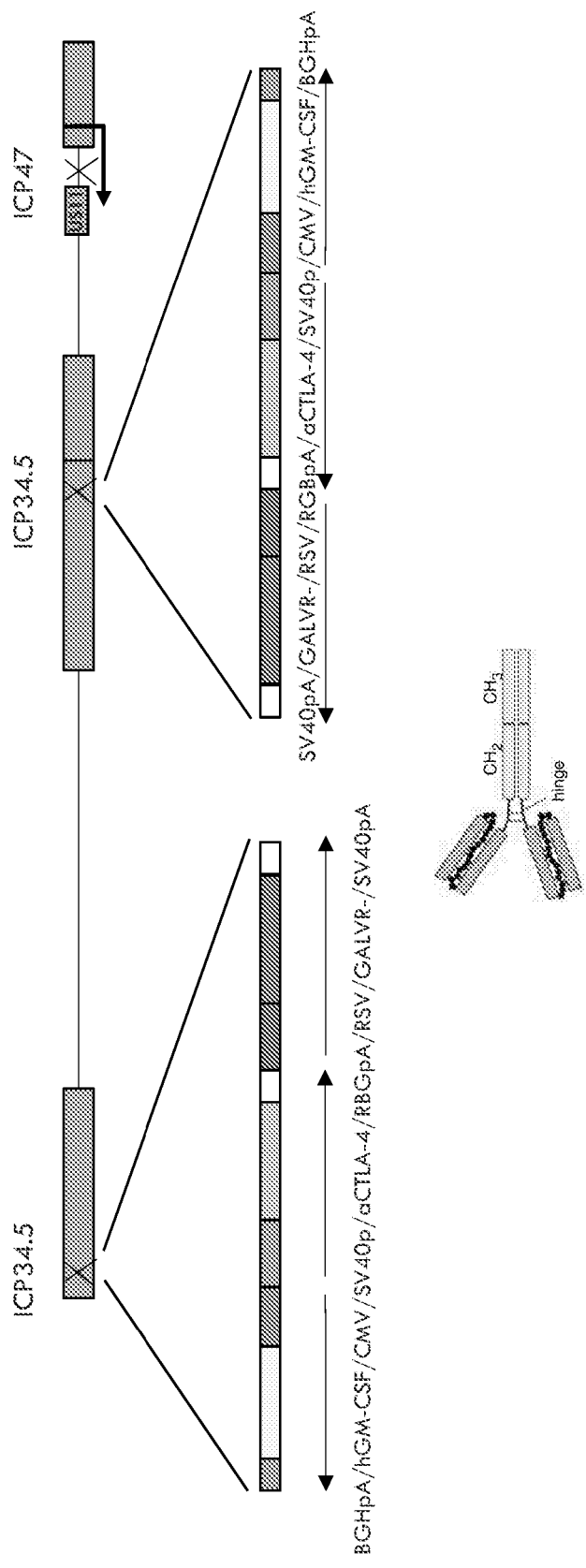
FIG. 13 shows the structure of ICP34.5 and ICP47 deleted viruses expressing GALVR-, GM-CSF and codon optimized anti-mouse or anti-human CTLA-4 antibody constructs (secreted scFv molecules linked to human or mouse IgG1 Fc regions). The scFvs contain the linked ([G$_4$S]$_3$) light and heavy variable chains from antibody 9D9 (US2011044953: mouse version) and from ipilimumab (US20150283234; human version). The resulting structure of the CTLA-4 inhibitor is also shown.
Figure 16:
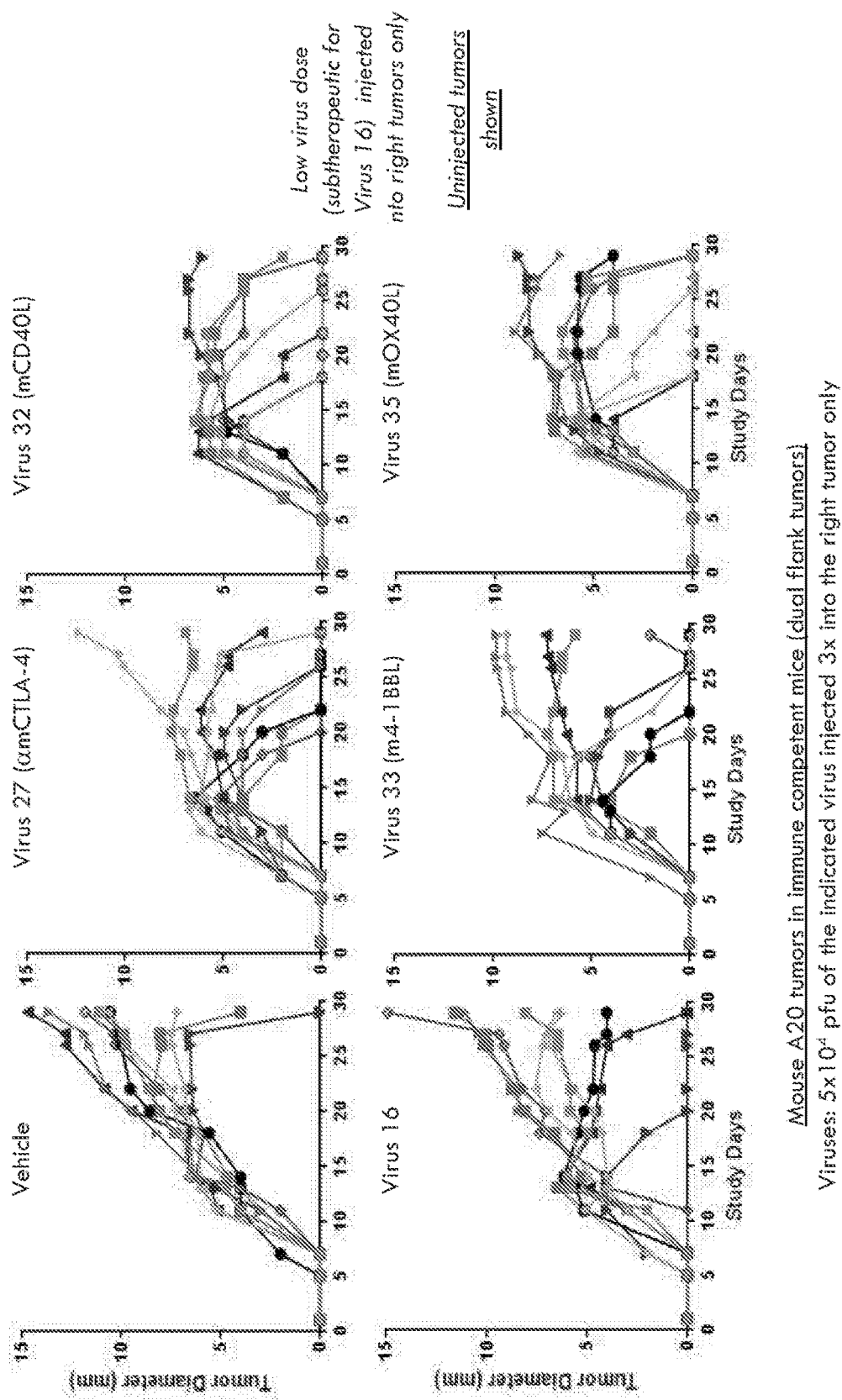
FIG. 16 shows the anti-tumor effects of viruses expressing anti-mCTLA-4 (virus 27), mCD40L (virus 32), mOX40L (virus 35), m4-2BBL (virus 33), each also with mGM-CSF and GALV-R- compared to virus 16 (expresses GALV and mGM-CSF).

Expression of Two Immune Stimulatory Molecules from a Virus Expressing a Fusogenic Protein Viruses similar to the GALV-R- and mGM-CSF expressing virus described above (Virus 16) were constructed, but additionally expressing mouse versions of CD40L (virus 32), ICOSL (virus 36), OX40L, (virus 35), 4-1BBL (virus 33) and GITRL (virus 34). Here, instead of using a plasmid containim ICP34.5 flanking regions and an expression cassette comprising GM-CSF and GALV-R- driven by a CMV and an RSV promoter, a plasmid containing ICP34.5 flanking regions and an expression cassette comprising GM-CSF, GALV and the additional proteins driven by a CMV an RSV and an MMLV promoter respectively were used for recombination with a virus containing GM-CSF, GALV and GFP inserted into ICP34.5. Non-GFP expressing plaques were again selected. Correct insertion was confirmed by PCR, and expression by western blotting and/or ELISA for the additional inserted gene. These viruses are shown in FIG. 5. Similarly, viruses expressing anti-mouse and anti-human CTLA-4 in addition to GALV and mGM-CSF were also constructed (Viruses 27 and 31 in FIG. 5 and see also FIG. 13). Effects of viruses expressing anti-mouse CTLA-4 (virus 27), mCD40L, (virus 32), m4-1BBL (virus 33) or mOX40L (virus 35) in addition to mGM-CSF and GALVR in vivo is shown in FIG. 16 which showed enhanced activity in A20 tumors as compared to virus 16 (expresses mGM-CSF and GALVR-). In these experiments tumors were induced in both flanks of mice, and virus or vehicle injected only into the right flank tumor. The dose of virus used was $5 \times 10^4$ pfu (50 ul of $1 \times 10^6$ pfu/ml in each case), given three times over one week. This dose level of virus is subtherapeutic for uninjected tumors for virus 16, which allows the benefits of the delivery of the additional molecules encoded by viruses 27, 32, 33 and 35 to clearly be seen.

Deposit Information

The following HSV1 strains were deposited at the ECACC, Culture Collections, Public Health England, Porton Down, Salisbury, SP4 0JG, United Kingdom on 19 Dec. 2016 by Replimune Limited and were allocated the indicated provisional accession numbers:

RH004A—Provisional Accession Number 16121902
RH015A—Provisional Accession Number 16121903
RH018A—Provisional Accession Number 16121904
RH021A—Provisional Accession Number 16121905
RH023A—Provisional Accession Number 16121906
RH031A—Provisional Accession Number 16121907
RH040A—Provisional Accession Number 16121908
RH047A—Provisional Accession Number 16121909.

The invention claimed is:

1. An oncolytic herpes simplex virus 1 (HSV1) which is strain RH018A having the accession number ECCAC 16121904;
strain RH004A having the accession number ECCAC 16121902;
strain RH031A having the accession number ECCAC 16121907;
strain RH040B having the accession number ECCAC 16121908;
strain RH015A having the accession number ECCAC 16121903;
strain RH021A having the accession number ECCAC 16121905;
strain RH023A having the accession number ECCAC 16121906; or
strain RH047A having the accession number ECCAC 16121909 wherein said virus is modified to:
(1) comprise one or more mutations in one or more viral genes, wherein the one or more mutations result in inhibited replication in normal tissue but still allow replication in tumors;
(2) to express a heterologous fusogenic protein; and/or
(3) to express an immune stimulatory protein in tumors.

2. The virus of claim 1 which is strain RH018A having the accession number EACC 16121904 modified to:
(1) comprise one or more mutations in one or more viral genes, wherein the one or more mutations result in inhibited replication in normal tissue but still allow replication in tumors;
(2) to express a heterologous fusogenic protein; and/or
(3) to express an immune stimulatory protein.

3. The virus of claim 1, wherein the virus:
(a) does not express functional ICP34.5;
(b) does not express functional ICP47; and/or
(c) expresses the US11 gene as an immediate early gene.

4. The virus of claim 1, which comprises:
(a) one or more immune stimulatory molecules or one or more immune stimulatory molecule encoding genes; and/or
(b) one or more fusogenic protein-encoding genes.

5. The virus of claim 4, wherein:
(a) the fusogenic protein is selected from the group consisting of vesicular stomatitis virus (VSV) G-protein, syncitin-1, syncitin-2, simian virus 5 (SV5) F-protein, measles virus (MV) H-protein, MV F-protein, respiratory syncytial virus (RSV) F-protein and a glycoprotein from gibbon ape leukemia virus (GALV), murine leukemia virus (MLV), Mason-Pfizer monkey virus (MPMV) or equine infectious anaemia virus (EIAV) from which the R peptide has been deleted; and/or
(b) the immune stimulatory molecule is GM-CSF, IL-2, IL-12, IL-15, IL-18, IL-21, IL, 24, a type I interferon, interferon gamma, a type III interferon, TNF alpha, an antagonist of TGF beta, an immune checkpoint antagonist or an agonist of an immune potentiating pathway including an agonist of CD40, ICOS, GITR 4-1-BB, OX40 or flt3, optionally CD40 ligand (CD40L), ICOS ligand, GITR ligand, 4-1-BB ligand, OX40 ligand or flt3 ligand.

6. The virus of claim 5, wherein:
(a) the fusogenic protein is the glycoprotein from gibbon ape leukemia virus (GALV) and has the R transmembrane peptide mutated or removed (GALV-R-): and/or (b) the immune stimulatory molecule is GM-CSF, or an agonist of GITR, ICOS, 4-1-BB, OX40 or CD40, such as GITRL GITRL, ICOSL, 4-1-BBL, OX40L or CD40, or the immune stimulatory molecules are GM-CSF and an agonist of GITR, ICOS, 4-1-BB, OX40 or CD40, such as GITRL, OX40L, 4-1-BBL, ICOSL or CD40L.

7. The virus of claim 4, wherein:
(a) the fusogenic protein-encoding gene and/or the immune stimulatory molecule-encoding gene are inserted into the ICP34.5 encoding locus, either by insertion, or partial or complete deletion, each under separate regulatory control, optionally in a back to back orientation in relation to each other; and/or
(b) the sequence of the gene encoding the fusogenic protein and/or the sequence of the gene encoding the immune stimulatory molecule is codon optimized so as to increase expression levels in target cells.

8. The virus of claim 1, which expresses three heterologous genes, wherein each of the three heterologous genes is driven by a different promoter selected from the CMV promoter, the RSV promoter, the SV40 promoter and a retroviral LTR promoter.

9. The virus of claim 8, which expresses four heterologous genes driven by each of the CMV promoter, the RSV promoter, the SV40 promoter and a retroviral LTR promoter, respectively.

10. The virus of claim 8, where the retroviral LTR promoter is from MMLV.

11. The virus of claim 1, which expresses three heterologous genes, wherein each of the three heterologous genes is terminated by a different poly adenylation sequence selected from the BGH, SV40, HGH and RBG poly adenylation sequences.

12. The virus of claim 11, which expresses four heterologous genes terminated by each of the BGH, SV40, HGH and RBG poly adenylation sequences, respectively.

13. A pharmaceutical composition comprising the virus of claim 1 and a pharmaceutically acceptable carrier or diluent.

14. A product of manufacture comprising a virus according to claim 1 in a sterile vial, ampoule or syringe.

15. A method of treating cancer, which comprises administering a therapeutically effective amount of the virus of claim 1 to a patient in need thereof.

16. The method of claim 15, which further comprises administering a therapeutically effective amount of a further anti-cancer agent to a patient in need thereof.

17. The method of claim 16, wherein the further anti-cancer agent is selected from an antagonist of an immune co-inhibitory pathway, an agonist of an immune co-stimulatory pathway, radiation and/or chemotherapy, an agent that targets a specific genetic mutation which occurs in tumors, an agent intended to induce an immune response to one or more tumor antigen(s) or neoantigen(s), a cellular product derived from T cells or NK cells, an agent intended to stimulate the STING, cGAS, TLR or other innate immune response and/or inflammatory pathway, a second virus optionally an oncolytic virus, an inhibitor of the indoleamine 2,3-dioxygenase (IDO) pathway, and combinations thereof.

18. The method of claim 17, wherein the antagonist of an immune co-inhibitory pathway is a CTLA-4 inhibitor, a PD-1 inhibitor, a PD-L1 inhibitor, a LAG-3 inhibitor, a TIM-3 inhibitor, a VISTA inhibitor, aCSF1R inhibitor, an IDO inhibitor, a CEACAM1 inhibitor, a KIR inhibitor, a SLAMF7 inhibitor or a CD47 inhibitor, and/or the agonist of an immune co-stimulatory pathway is a GITR agonist, a 4-1-BB agonist, an OX40agonist, a CD40 agonist or an ICOS agonist.

19. The method of claim 17, wherein the further anti-cancer agent comprises an antibody.

20. The method of claim 16, wherein the virus and the further anti-cancer agent(s) are administered separately.

21. The method of claim 16, wherein the virus and the further anti-cancer agent(s) are administered concurrently.

22. The method of claim 16, wherein the cancer is a solid tumor.

* * * * *